US009289167B2

(12) United States Patent
Diab et al.

(10) Patent No.: US 9,289,167 B2
(45) Date of Patent: Mar. 22, 2016

(54) SIGNAL PROCESSING APPARATUS AND METHOD

(71) Applicant: Masimo Corporation, Irvine, CA (US)

(72) Inventors: Mohamed K. Diab, Mission Viejo, CA (US); Rex J. McCarthy, Mission Viejo, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 13/706,298

(22) Filed: Dec. 5, 2012

(65) Prior Publication Data
US 2013/0197328 A1 Aug. 1, 2013

Related U.S. Application Data

(60) Continuation of application No. 13/471,340, filed on May 14, 2012, which is a continuation of application No. 11/842,128, filed on Aug. 20, 2007, now Pat. No. 8,180,420, which is a continuation of application No.
(Continued)

(51) Int. Cl.
A61B 5/1455 (2006.01)
A61B 5/024 (2006.01)
(Continued)

(52) U.S. Cl.
CPC ............ A61B 5/14552 (2013.01); A61B 5/0205 (2013.01); A61B 5/02416 (2013.01);
(Continued)

(58) Field of Classification Search
CPC ............. A61B 5/0205; A61B 5/02416; A61B 5/02433; A61B 5/1455; A61B 5/14551; A61B 5/14552; A61B 5/7203; A61B 5/7214; A61B 5/7257; A61B 5/726
USPC ......... 600/310, 322, 323, 330, 336, 481, 500; 702/191–197
See application file for complete search history.

(56) References Cited

U.S. PATENT DOCUMENTS 3,638,640 A 2/1972 Shaw
3,647,299 A 3/1972 Lavallee
(Continued)

FOREIGN PATENT DOCUMENTS

DE 3135802 3/1983
DE 3328862 A1 2/1985
(Continued)

OTHER PUBLICATIONS

147 Fed.Appx. 158,2005 WL 2139867 (CAFed.), *Mallinckrodt, Inc. and Nellcor Puritan Bennett, Inc. v. Masimo Corporation*, DX 2857, *Masimo Corporation v. Philips Electronics & Philips Electronics North America Corporation, et al.*, Case 1: 09-cv-00080-LPS (District of Delaware).
(Continued)

*Primary Examiner* — Eric Winakur
(74) *Attorney, Agent, or Firm* — Knobbe, Martens, Olson & Bear, LLP

(57) ABSTRACT

A method and an apparatus to analyze two measured signals that are modeled as containing desired and undesired portions such as noise, FM and AM modulation. Coefficients relate the two signals according to a model defined in accordance with the present invention. In one embodiment, a transformation is used to evaluate a ratio of the two measured signals in order to find appropriate coefficients. The measured signals are then fed into a signal scrubber which uses the coefficients to remove the unwanted portions. The signal scrubbing is performed in either the time domain or in the frequency domain. The method and apparatus are particularly advantageous to blood oximetry and pulserate measurements. In another embodiment, an estimate of the pulserate is obtained by applying a set of rules to a spectral transform of the scrubbed signal. In another embodiment, an estimate of the pulserate is obtained by transforming the scrubbed signal from a first spectral domain into a second spectral domain. The pulserate is found by identifying the largest spectral peak in the second spectral domain.

26 Claims, 19 Drawing Sheets

Related U.S. Application Data

10/791,683, filed on Mar. 2, 2004, now Pat. No. 7,471,971, which is a continuation of application No. 09/547,588, filed on Apr. 11, 2000, now Pat. No. 6,699,194, which is a continuation of application No. 09/081,539, filed on May 19, 1998, now Pat. No. 6,067,462, which is a division of application No. 08/834,194, filed on Apr. 14, 1997, now Pat. No. 6,002,952.

(51) Int. Cl.
    *A61B 5/00*         (2006.01)
    *G06K 9/00*         (2006.01)
    *A61B 5/0205*     (2006.01)

(52) U.S. Cl.
    CPC ............ *A61B5/14551* (2013.01); *A61B 5/7203* (2013.01); *A61B 5/7214* (2013.01); *G06K 9/0051* (2013.01); *A61B 5/02433* (2013.01); *A61B 5/1455* (2013.01); *A61B 5/726* (2013.01); *A61B 5/7257* (2013.01)

(56) References Cited

U.S. PATENT DOCUMENTS

| | | | |
|---|---|---|---|
| 3,659,591 | A | 5/1972 | Doll et al. |
| 3,704,706 | A | 12/1972 | Herczfeld et al. |
| 3,747,001 | A | 7/1973 | Fasching |
| 3,811,428 | A | 5/1974 | VanHorn |
| 3,991,277 | A | 11/1976 | Hirata |
| 3,998,550 | A | 12/1976 | Konishi et al. |
| 4,051,522 | A | 9/1977 | Healy |
| 4,063,551 | A | 12/1977 | Sweeney |
| 4,085,378 | A | 4/1978 | Ryan |
| 4,086,915 | A | 5/1978 | Kofsky et al. |
| 4,086,917 | A | 5/1978 | Burks |
| 4,095,117 | A | 6/1978 | Nagy |
| 4,129,124 | A | 12/1978 | Thalmann |
| 4,167,331 | A | 9/1979 | Nielsen |
| 4,197,836 | A | 4/1980 | Wagner et al. |
| 4,238,746 | A | 12/1980 | McCool et al. |
| 4,243,935 | A | 1/1981 | McCool et al. |
| 4,266,554 | A | 5/1981 | Hamaguri |
| 4,301,808 | A | 11/1981 | Taus |
| 4,305,398 | A | 12/1981 | Sawa |
| 4,308,456 | A | 12/1981 | Van Der Gaag et al. |
| 4,357,944 | A | 11/1982 | Mauser |
| 4,407,290 | A | 10/1983 | Wilber |
| 4,446,871 | A | 5/1984 | Imura |
| 4,519,396 | A | 5/1985 | Epstein et al. |
| 4,537,200 | A | 8/1985 | Widrow |
| 4,573,479 | A | 3/1986 | Tucciloo |
| 4,586,513 | A | 5/1986 | Hamaguri |
| 4,617,589 | A | 10/1986 | Weckenbrock |
| 4,623,248 | A | 11/1986 | Sperinde |
| 4,649,505 | A | 3/1987 | Zinser, Jr. et al. |
| 4,653,498 | A | 3/1987 | New |
| 4,660,151 | A | 4/1987 | Chipman et al. |
| 4,680,708 | A | 7/1987 | Ambos |
| 4,694,833 | A | 9/1987 | Hamaguri |
| 4,714,341 | A | 12/1987 | Hamaguri et al. |
| 4,719,920 | A | 1/1988 | Alt |
| 4,723,294 | A | 2/1988 | Taguchi |
| 4,745,398 | A | 5/1988 | Abel |
| 4,751,931 | A | 6/1988 | Briller et al. |
| 4,765,340 | A | 8/1988 | Sakai |
| 4,773,422 | A | 9/1988 | Isaacson et al. |
| 4,777,960 | A | 10/1988 | Berger |
| 4,781,200 | A | 11/1988 | Baker |
| 4,781,201 | A | 11/1988 | Wright |
| 4,793,361 | A | 12/1988 | DuFault |
| 4,796,620 | A | 1/1989 | Imran |
| 4,799,493 | A | 1/1989 | DuFault |
| 4,800,495 | A | 1/1989 | Smith |
| 4,802,486 | A | 2/1989 | Goodman |
| 4,807,631 | A | 2/1989 | Hersh et al. |
| 4,819,646 | A | 4/1989 | Cheung et al. |
| 4,819,752 | A | 4/1989 | Zelin |
| 4,824,242 | A | 4/1989 | Frick et al. |
| 4,846,183 | A | 7/1989 | Martin |
| 4,848,901 | A | 7/1989 | Hood, Jr. |
| 4,854,699 | A | 8/1989 | Edgar, Jr. |
| 4,858,199 | A | 8/1989 | Griffith |
| 4,859,056 | A | 8/1989 | Prosser et al. |
| 4,859,057 | A | 8/1989 | Taylor et al. |
| 4,860,759 | A | 8/1989 | Kahn et al. |
| 4,863,265 | A | 9/1989 | Flower et al. |
| 4,867,161 | A | 9/1989 | Schaldach |
| 4,867,165 | A | 9/1989 | Noller et al. |
| 4,867,571 | A | 9/1989 | Frick et al. |
| 4,869,253 | A | 9/1989 | Craig, Jr. et al. |
| 4,869,254 | A | 9/1989 | Stone et al. |
| 4,870,558 | A | 9/1989 | Luce |
| 4,870,588 | A | 9/1989 | Merhav |
| 4,883,353 | A | 11/1989 | Hausman et al. |
| 4,883,356 | A | 11/1989 | deMey, II |
| 4,884,576 | A | 12/1989 | Alt |
| 4,890,624 | A | 1/1990 | Ganguly |
| 4,892,101 | A | 1/1990 | Cheung et al. |
| 4,897,162 | A | 1/1990 | Lewandowski et al. |
| 4,907,594 | A | 3/1990 | Muz |
| 4,911,167 | A | 3/1990 | Corenman et al. |
| 4,913,150 | A | 4/1990 | Cheung et al. |
| 4,926,863 | A | 5/1990 | Alt |
| 4,927,264 | A | 5/1990 | Shiga et al. |
| 4,928,692 | A | 5/1990 | Goodman et al. |
| 4,934,372 | A | 6/1990 | Corenman et al. |
| 4,942,877 | A | 7/1990 | Sakai |
| 4,948,248 | A | 8/1990 | Lehman |
| 4,949,710 | A | 8/1990 | Dorsett et al. |
| 4,955,379 | A | 9/1990 | Hall |
| 4,956,867 | A | 9/1990 | Zurek et al. |
| 4,958,638 | A | 9/1990 | Sharpe |
| 4,960,126 | A | 10/1990 | Conlon et al. |
| 4,960,128 | A | 10/1990 | Gordon et al. |
| 4,964,408 | A | 10/1990 | Hink et al. |
| 4,965,840 | A | 10/1990 | Subbarao |
| 4,967,571 | A | 11/1990 | Sporri |
| 4,974,598 | A | 12/1990 | John |
| 5,003,252 | A | 3/1991 | Nystrom |
| 5,003,977 | A | 4/1991 | Suzuki et al. |
| RE33,643 | E | 7/1991 | Isaacson |
| 5,029,082 | A | 7/1991 | Shen |
| 5,041,187 | A | 8/1991 | Hink et al. |
| 5,042,499 | A | 8/1991 | Frank et al. |
| 5,054,495 | A | 10/1991 | Uemura et al. |
| 5,057,695 | A | 10/1991 | Hirao et al. |
| 5,069,213 | A | 12/1991 | Polczynski |
| 5,078,136 | A | 1/1992 | Stone et al. |
| 5,105,354 | A | 4/1992 | Nishimura |
| 5,109,862 | A | 5/1992 | Kelen |
| 5,144,951 | A | 9/1992 | Uematsu et al. |
| 5,163,438 | A | 11/1992 | Gordon et al. |
| 5,170,791 | A | 12/1992 | Boos et al. |
| 5,188,108 | A | 2/1993 | Secker |
| 5,190,038 | A | 3/1993 | Polson |
| 5,190,047 | A | 3/1993 | Odagiri et al. |
| 5,193,124 | A | 3/1993 | Subbarao |
| 5,209,237 | A | 5/1993 | Rosenthal |
| 5,217,013 | A | 6/1993 | Lewis et al. |
| 5,218,962 | A | 6/1993 | Mannheimer |
| 5,226,417 | A | 7/1993 | Swedlow |
| 5,237,994 | A | 8/1993 | Goldberger |
| 5,246,002 | A | 9/1993 | Prosser |
| 5,246,003 | A | 9/1993 | DeLonzor |
| 5,247,931 | A | 9/1993 | Norwood |
| 5,259,381 | A | 11/1993 | Cheung |
| 5,270,942 | A | 12/1993 | Reed |
| 5,273,036 | A | 12/1993 | Kronberg et al. |
| 5,285,783 | A | 2/1994 | Secker |
| 5,285,784 | A | 2/1994 | Seeker |
| 5,297,548 | A | 3/1994 | Pologe |
| 5,299,120 | A | 3/1994 | Kaestle |
| 5,307,284 | A | 4/1994 | Brunfeldt |

(56) References Cited

U.S. PATENT DOCUMENTS

| | | |
|---|---|---|
| 5,308,919 A | 5/1994 | Minnich |
| 5,309,917 A | 5/1994 | Wang |
| 5,319,355 A | 6/1994 | Russek |
| 5,331,394 A | 7/1994 | Shalon et al. |
| 5,337,744 A | 8/1994 | Branigan |
| 5,341,805 A | 8/1994 | Stavridi et al. |
| 5,345,510 A | 9/1994 | Singhi |
| 5,349,952 A | 9/1994 | McCarthy et al. |
| 5,353,356 A | 10/1994 | Waugh et al. |
| 5,355,880 A | 10/1994 | Thomas et al. |
| 5,355,882 A | 10/1994 | Ukawa |
| 5,357,965 A | 10/1994 | Hall et al. |
| 5,368,224 A | 11/1994 | Richardson |
| D353,195 S | 12/1994 | Savage et al. |
| D353,196 S | 12/1994 | Savage et al. |
| 5,377,676 A | 1/1995 | Vari et al. |
| 5,384,451 A | 1/1995 | Smith et al. |
| 5,398,003 A | 3/1995 | Heyl et al. |
| 5,398,680 A | 3/1995 | Polson et al. |
| 5,404,003 A | 4/1995 | Smith |
| 5,405,364 A | 4/1995 | Noren |
| 5,406,952 A | 4/1995 | Barnes |
| 5,406,955 A | 4/1995 | Bledsoe |
| 5,411,031 A | 5/1995 | Yomtov |
| D359,546 S | 6/1995 | Savage et al. |
| 5,421,329 A | 6/1995 | Casciani |
| 5,431,170 A | 7/1995 | Mathews |
| D361,840 S | 8/1995 | Savage et al. |
| 5,438,983 A | 8/1995 | Falcone |
| 5,442,940 A | 8/1995 | Secker |
| D362,063 S | 9/1995 | Savage et al. |
| 5,448,991 A | 9/1995 | Polson |
| 5,452,717 A | 9/1995 | Branigan et al. |
| D363,120 S | 10/1995 | Savage et al. |
| 5,456,252 A | 10/1995 | Vari et al. |
| 5,458,128 A | 10/1995 | Pulanyi et al. |
| 5,469,856 A | 11/1995 | Lundstrom |
| RE35,122 E | 12/1995 | Corenman et al. |
| 5,479,934 A | 1/1996 | Imran |
| 5,481,620 A | 1/1996 | Vaidyanathan |
| 5,482,036 A | 1/1996 | Diab et al. |
| 5,490,505 A | 2/1996 | Diab et al. |
| 5,494,032 A | 2/1996 | Robinson et al. |
| 5,494,043 A | 2/1996 | O'Sullivan et al. |
| 5,503,148 A | 4/1996 | Pologe |
| 5,515,169 A | 5/1996 | Cargill et al. |
| 5,515,847 A | 5/1996 | Braig |
| 5,533,511 A | 7/1996 | Kaspari et al. |
| 5,534,851 A | 7/1996 | Russek |
| 5,542,421 A | 8/1996 | Erdman |
| 5,549,111 A | 8/1996 | Wright et al. |
| 5,557,284 A | 9/1996 | Hartman |
| 5,561,275 A | 10/1996 | Savage et al. |
| 5,562,002 A | 10/1996 | Lalin |
| 5,575,284 A | 11/1996 | Athan |
| 5,588,427 A | 12/1996 | Tien |
| 5,588,435 A | 12/1996 | Weng et al. |
| 5,590,649 A | 1/1997 | Caro et al. |
| 5,602,924 A | 2/1997 | Durand et al. |
| 5,609,156 A | 3/1997 | Keith |
| 5,610,996 A | 3/1997 | Eller |
| 5,622,180 A | 4/1997 | Tammi |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,652,566 A | 7/1997 | Lambert |
| 5,662,105 A | 9/1997 | Tien |
| 5,685,299 A | 11/1997 | Diab et al. |
| 5,685,316 A | 11/1997 | Schookin |
| 5,704,365 A | 1/1998 | Albrecht et al. |
| 5,720,293 A | 2/1998 | Quinn |
| 5,724,032 A | 3/1998 | Klein |
| D393,830 S | 4/1998 | Tobler et al. |
| 5,738,104 A | 4/1998 | Lo et al. |
| 5,743,262 A | 4/1998 | Lepper |
| 5,749,900 A | 5/1998 | Schroeppel |
| 5,758,644 A | 6/1998 | Diab et al. |
| 5,760,910 A | 6/1998 | Lepper, Jr. et al. |
| 5,769,785 A | 6/1998 | Diab et al. |
| 5,782,237 A | 7/1998 | Casciani |
| 5,782,757 A | 7/1998 | Diab et al. |
| 5,785,659 A | 7/1998 | Caro et al. |
| 5,791,347 A | 8/1998 | Flaherty et al. |
| 5,795,300 A | 8/1998 | Bryars |
| 5,797,840 A | 8/1998 | Akselrod |
| 5,800,348 A | 9/1998 | Kaestle |
| 5,807,267 A | 9/1998 | Bryars et al. |
| 5,810,724 A | 9/1998 | Gronvall |
| 5,810,734 A | 9/1998 | Caro et al. |
| 5,823,950 A | 10/1998 | Diab et al. |
| 5,830,131 A | 11/1998 | Caro et al. |
| 5,830,137 A | 11/1998 | Scharf |
| 5,833,618 A | 11/1998 | Caro et al. |
| RE36,000 E | 12/1998 | Swedlow et al. |
| 5,842,979 A | 12/1998 | Jarman |
| 5,842,981 A | 12/1998 | Larsen et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,890,929 A | 4/1999 | Mills et al. |
| 5,891,023 A | 4/1999 | Lynn |
| 5,904,654 A | 5/1999 | Wohltmann et al. |
| 5,919,134 A | 7/1999 | Diab |
| 5,921,921 A | 7/1999 | Potratz et al. |
| 5,934,277 A | 8/1999 | Mortz |
| 5,934,925 A | 8/1999 | Tobler et al. |
| 5,940,182 A | 8/1999 | Lepper, Jr. et al. |
| 5,950,139 A | 9/1999 | Korycan |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,018,673 A | 1/2000 | Chin |
| 6,022,321 A | 2/2000 | Amano |
| 6,027,452 A | 2/2000 | Flaherty et al. |
| 6,036,642 A | 3/2000 | Diab et al. |
| 6,045,509 A | 4/2000 | Caro et al. |
| 6,047,203 A | 4/2000 | Sackner et al. |
| 6,064,910 A | 5/2000 | Andersson et al. |
| 6,067,462 A | 5/2000 | Diab et al. |
| 6,081,735 A | 6/2000 | Diab et al. |
| 6,081,742 A | 6/2000 | Amano |
| 6,083,172 A | 7/2000 | Baker, Jr. et al. |
| 6,088,607 A | 7/2000 | Diab et al. |
| 6,110,522 A | 8/2000 | Lepper, Jr. et al. |
| 6,119,026 A | 9/2000 | McNulty et al. |
| 6,122,535 A | 9/2000 | Kaestle et al. |
| 6,124,597 A | 9/2000 | Shehada |
| 6,126,595 A | 10/2000 | Amano |
| 6,128,521 A | 10/2000 | Marro et al. |
| 6,129,675 A | 10/2000 | Jay |
| 6,135,952 A | 10/2000 | Coetzee |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,188,407 B1 | 2/2001 | Smith et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,241,684 B1 | 6/2001 | Amano |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |

(56) References Cited

U.S. PATENT DOCUMENTS

| | | | |
|---|---|---|---|
| 6,317,627 B1 | 11/2001 | Ennen et al. |
| 6,321,100 B1 | 11/2001 | Parker |
| 6,325,761 B1 | 12/2001 | Jay |
| 6,330,468 B1 | 12/2001 | Scharf |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,833 B1 | 6/2002 | Baker, Jr. et al. |
| 6,430,437 B1 | 8/2002 | Marro |
| 6,430,525 B1 | 8/2002 | Weber et al. |
| 6,438,399 B1 | 8/2002 | Kurth |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Al Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,631,281 B1 | 10/2003 | Kastle |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,623 B1 | 11/2003 | Kastle |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab |
| 6,721,582 B2 | 4/2004 | Trepagnier et al. |
| 6,721,584 B2 | 4/2004 | Baker et al. |
| 6,721,585 B1 | 4/2004 | Parker |
| 6,725,074 B1 | 4/2004 | Kastle |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab et al. |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |

(56) References Cited

U.S. PATENT DOCUMENTS

| | | |
|---|---|---|
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al-Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,888,708 B2 | 11/2014 | Diab et al. |
| 2002/0077536 A1 | 6/2002 | Diab et al. |
| 2002/0082488 A1 | 6/2002 | Al-Ali |
| 2002/0128544 A1 | 9/2002 | Kiani-Azarbayjany et al. |
| 2002/0161291 A1 | 10/2002 | Kiani |
| 2003/0000522 A1 | 1/2003 | Lynn |
| 2003/0018241 A1 | 1/2003 | Mannheimer |
| 2003/0073890 A1 | 4/2003 | Hanna |
| 2003/0120164 A1 | 6/2003 | Nielsen |
| 2004/0068164 A1 | 4/2004 | Diab et al. |
| 2004/0204637 A1 | 10/2004 | Diab et al. |
| 2005/0096517 A1 | 5/2005 | Diab et al. |
| 2005/0209517 A1 | 9/2005 | Diab et al. |
| 2006/0200016 A1 | 9/2006 | Diab et al. |
| 2006/0211930 A1* | 9/2006 | Scharf et al. .................. 600/336 |
| 2006/0217609 A1 | 9/2006 | Diab et al. |
| 2007/0225581 A1 | 9/2007 | Diab et al. |
| 2007/0249918 A1 | 10/2007 | Diab et al. |
| 2007/0291832 A1 | 12/2007 | Diab et al. |
| 2008/0004514 A1 | 1/2008 | Diab et al. |
| 2008/036752 A1 | 2/2008 | Diab et al. |

FOREIGN PATENT DOCUMENTS

| | | |
|---|---|---|
| DE | 3629447 | 4/1987 |
| DE | 3609912 | 10/1987 |
| DE | 3609913 | 10/1987 |
| DE | 3715823 | 12/1987 |
| DE | 8713037 U1 | 4/1988 |
| DE | 4007393 | 9/1990 |
| DE | 3932428 | 4/1991 |
| DE | 4001574 | 7/1991 |
| DE | 4009970 | 10/1991 |
| DE | 4011065 | 10/1991 |
| DE | 4111505 | 10/1992 |
| DE | 4223045 | 1/1994 |
| DE | 4303047 | 8/1994 |
| DE | 29501672 | 8/1995 |
| DE | 19602460 | 8/1996 |
| DE | 19524092 | 1/1997 |
| EP | 102 816 | 3/1984 |
| EP | 0104771 B1 | 4/1984 |
| EP | 0155670 | 9/1985 |
| EP | 0215730 A2 | 3/1987 |
| EP | 0335357 | 3/1989 |
| EP | 0329196 | 8/1989 |
| EP | 0341327 | 11/1989 |
| EP | 0352923 | 1/1990 |
| EP | 0600298 A1 | 6/1994 |
| EP | 0645117 | 3/1995 |
| EP | 0659384 | 6/1995 |
| EP | 0760223 | 8/1995 |
| EP | 0729726 A2 | 9/1996 |
| EP | 0743042 | 11/1996 |
| EP | 0744154 | 11/1996 |
| EP | 0 760 223 | 5/1997 |
| EP | 0 761 159 | 9/1999 |
| EP | 0729726 B1 | 4/2004 |
| GB | 2 075 668 | 11/1981 |
| GB | 2101335 | 1/1983 |
| GB | 2 156 997 | 10/1985 |
| GB | 2 166 326 | 4/1986 |
| GB | 2 235 288 | 2/1991 |
| JP | 50-143380 | 11/1975 |
| JP | 55-120858 | 9/1980 |
| JP | 58-065137 | 4/1983 |
| JP | 63-84519 | 4/1988 |
| JP | 63-277034 | 11/1988 |
| JP | 02-136125 | 5/1990 |
| JP | 04-371166 | 12/1992 |
| JP | 06-054813 | 3/1994 |

(56) References Cited

FOREIGN PATENT DOCUMENTS

| JP | 07-088092 | 4/1995 |
|---|---|---|
| JP | 07-148126 | 6/1995 |
| JP | 07-148253 | 6/1995 |
| JP | 07-227383 | 8/1995 |
| JP | 08-173390 | 7/1996 |
| JP | 09-84776 | 3/1997 |
| WO | WO 84/01705 | 5/1984 |
| WO | WO 84/03032 | 8/1984 |
| WO | WO 86/02250 | 4/1986 |
| WO | WO 86/07248 | 12/1986 |
| WO | WO 92/11803 | 7/1992 |
| WO | WO 92/15955 | 9/1992 |
| WO | WO 92/20273 | 11/1992 |
| WO | WO 93/19665 | 10/1993 |
| WO | WO 94/09698 | 5/1994 |
| WO | WO 95/21567 | 8/1995 |
| WO | WO 96/23442 A1 | 8/1996 |
| WO | WO 98/43071 | 10/1998 |

OTHER PUBLICATIONS

Sep. 9, 2014 Baura Supplemental Expert Report re Validity of Masimo's Patent, *Masimo Corporation v. Philips Electronics North America Corporation et al*, Case 1:09-cv-00080-LPS (District of Delaware).

Aug. 1, 2014 Stone Third Supplemental Expert Report—Invalidity of 222 & 984, *Masimo Corporation v. Philips Electronics North America Corporation et al*, Case 1:09-cv-00080-LPS (District of Delaware).

Jul. 7, 2014 Redacted Baura Report, *Masimo Corporation v. Philips Electronics North America Corporation et al*, Case 1:09-cv-00080-LPS (District of Delaware).

Sep. 30, 2014 Final Jury Instructions, *Masimo Corporation v. Philips Electronics North America Corporation et al*, Case 1:09-cv-00080-LPS (District of Delaware).

Sep. 15, 2014 *Masimo v Philips, et al*, 09cv80-LPS vol. A (Condensed)—day 1, *Masimo Corporation v. Philips Electronics North America Corporation et al*, Case 1:09-cv-00080-LPS (District of Delaware).

Sep. 16, 2014 *Masimo v Philips, et al*, 09cv80-LPS vol. B (condensed)—day 2, *Masimo Corporation v. Philips Electronics North America Corporation et al*, Case 1:09-cv-00080-LPS (District of Delaware).

Sep. 17, 2014 Trial Day 3 vol. C [Kiani, Goldstein, Diab] (Condensed) pp. 502-800, *Masimo Corporation v. Philips Electronics North America Corporation et al*, Case 1:09-cv-00080-LPS (District of Delaware).

Sep. 18, 2014 Trial Day 4 vol. D [Wallen, Ecock, Haas, DiSanzo, Quill, Noller, Blank, Neumann, Bindszus, et al] (Condensed) pp. 801-1062, *Masimo Corporation v. Philips Electronics North America Corporation et al*, Case 1:09-cv-00080-LPS (District of Delaware).

Sep. 19, 2014 Trial Day 5 vol. E [Fishel, Baura, Wagner, Mancuso, Haas] (Condensed) pp. 1063-1297, *Masimo Corporation v. Philips Electronics North America Corporation et al*, Case 1:09-cv-00080-LPS (District of Delaware).

Sep. 22, 2014 Trial Day 6 vol. F [Haas, Kaestle, Eichhorn] (Condensed) pp. 1298-1615, *Masimo Corporation v. Philips Electronics North America Corporation et al*, Case 1:09-cv-00080-LPS (District of Delaware).

Sep. 23, 2014 Trial Day 7 vol. G [Eichhorn, Weber, Poison, Stone] (Condensed) pp. 1616-1785, *Masimo Corporation v. Philips Electronics North America Corporation et al*, Case 1:09-cv-00080-LPS (District of Delaware).

Sep. 24, 2014 Trial Day 8 vol. H [Stone, DiSanzo, Ochroch, Willis, Heckendorn, Keeley] (Condensed) pp. 1786-2015, *Masimo Corporation v. Philips Electronics North America Corporation et al*, Case 1:09-cv-00080-LPS (District of Delaware).

Sep. 16, 2014 [Corrected] Trial Day 2 vol. B [Opening, Kiani] (Condensed) pp. 227-501, *Masimo Corporation v. Philips Electronics North America Corporation et al*, Case 1:09-cv-00080-LPS (District of Delaware).

Sep. 29, 2014 Trial Day 9 vol. I [Keeley, Turner, Wagner, Melek, Baura, Kiani] (Condensed) pp. 2016-2319, *Masimo Corporation v. Philips Electronics North America Corporation et al*, Case 1:09-cv-00080-LPS (District of Delaware).

Sep. 30, 2014 Trial Day 10 vol. J [Jury Instructions, Closing Arguments] (Condensed) pp. 2320-2522, *Masimo Corporation v. Philips Electronics North America Corporation et al*, Case 1:09-cv-00080-LPS (District of Delaware).

Oct. 1, 2014 Trial Day 11 vol. K [Jury Deliberations, Verdict] (Condensed) pp. 2523-2540, *Masimo Corporation v. Philips Electronics North America Corporation et al*, Case 1:09-cv-00080-LPS (District of Delaware).

Sep. 28, 2014 Stone Demonstratives DDX151-DDX235,*Masimo Corporation v. Philips Electronics North America Corporation et al*, Case 1:09-cv-00080-LPS (District of Delaware).

Oct. 1, 2014 [913] Corrected [Redacted] Jury Verdict, *Masimo Corporation v. Philips Electronics North America Corporation et al*, Case 1:09-cv-00080-LPS (District of Delaware).

Aug. 15, 2014 [282] Defendants' Notice Pursuant to 35 U.S.C. § 282, *Masimo Corporation v. Philips Electronics North America Corporation et al*, Case 1:09-cv-00080-LPS (District of Delaware).

Aug. 18, 2014 [834] Proposed Final Pretrial Order, *Masimo Corporation v. Philips Electronics North America Corporation et al*, Case 1:09-cv-00080-LPS (District of Delaware).

Oct. 30, 2014 Combined Final Trial Transcripts, *Masimo Corporation v. Philips Electronics North America Corporation et al*, Case 1:09-cv-00080-LPS (District of Delaware).

Feb. 17, 2015 [965] Letter from Julia Heaney to the Honorable Leonard P. Stark Enclosing "Supplemental Expert Report of Professor Gail D. Baura, Ph.D. Concerning the Validity of U.S. Pat. Nos. 6,263,222 and 7,215,984", *Masimo Corporation v. Philips Electronics & Philips Electronics North America Corporation, et al.*, Case 1:09-cv-00080-LPS (District of Delaware).

Feb. 17, 2015 [966] Letter from Julia Heaney to the Honorable Leonard P. Stark and Exhibits Regarding Inequitable Conduct and Patent Misuse, *Masimo Corporation v. Philips Electronics & Philips Electronics North America Corporation, et al.*, Case 1:09-cv-00080-LPS (District of Delaware).

Feb. 17, 2015 [967] Letter from David E. Moore to the Honorable Leonard P. Stark Regarding Patent Misuse, *Masimo Corporation v. Philips Electronics & Philips Electronics North America Corporation, et al.*, Case 1:09-cv-00080-LPS (District of Delaware).

Feb. 21, 2015 [972] Masimo Corporation's Motion for Judgment on the Pleadings Pursuant to Fed. R. Civ. P. 12(c), *Masimo Corporation v. Philips Electronics & Philips Electronics North America Corporation, et al.*, Case 1:09-cv-00080-LPS (District of Delaware).

Feb. 21, 2015 [973] Opening Brief in Support of Masimo Corporation's Motion for Judgment on the Pleadings Pursuant to Fed. R. Civ. P. 12(c), *Masimo Corporation v. Philips Electronics & Philips Electronics North America Corporation, et al.*, Case 1:09-cv-00080-LPS (District of Delaware).

Feb. 25, 2015 [974] Philips' Opening Brief in Support of Finding the '984 Patent Unenforceable Due to Inequitable Conduct, *Masimo Corporation v. Philips Electronics & Philips Electronics North America Corporation, et al.*, Case 1:09-cv-00080-LPS (District of Delaware).

Feb. 25, 2015 [975] Defendant Philips' Proposed Findings of Facts and Conclusions of Law, *Masimo Corporation v. Philips Electronics & Philips Electronics North America Corporation, et al.*, Case 1:09-cv-00080-LPS (District of Delaware).

Feb. 25, 2015 [976] Masimo's Opening Post-Trial Brief on Inequitable Conduct, *Masimo Corporation v. Philips Electronics & Philips Electronics North America Corporation, et al.*, Case 1:09-cv-00080-LPS (District of Delaware).

Feb. 25, 2015 [977] Masimo Corporation's Proposed Findings of Fact and Conclusions of Law on Inequitable Conduct, *Masimo Corporation v. Philips Electronics & Philips Electronics North America Corporation, et al.*, Case 1:09-cv-00080-LPS (District of Delaware).

(56) References Cited

OTHER PUBLICATIONS

Mar. 2, 2015 [978] Defendant's Answering Brief in Opposition to Masimo Corporation's Motion to Dismiss Pursuant to Fed. R. Civ. P. 12(c), *Masimo Corporation v. Philips Electronics & Philips Electronics North America Corporation, et al.*, Case 1:09-cv-00080-LPS (District of Delaware).
Mar. 4, 2015 [980] Masimo's Responsive Post-Trial Brief on Inequitable Conduct, *Masimo Corporation v. Philips Electronics & Philips Electronics North America Corporation, et al.*, Case 1:09-cv-00080-LPS (District of Delaware).
Mar. 4, 2015 [981] Masimo Corporation's Reply Brief in Support of Motion for Judgment on the Pleadings Pursuant to Fed. R. Civ. P. 12(c), *Masimo Corporation v. Philips Electronics & Philips Electronics North America Corporation, et al.*, Case 1:09-cv-00080-LPS (District of Delaware).
Mar. 4, 2015 [982] Philips' Response Brief in Support of Finding the '984 Patent Unenforceable Due to Inequitable Conduct, *Masimo Corporation v. Philips Electronics & Philips Electronics North America Corporation, et al.*, Case 1:09-cv-00080-LPS (District of Delaware).
Mar. 11, 2015 [986-1] Defendants' Sur-Reply Brief in Opposition to Masimo Corporation's Motion for Judgment on the Pleadings Pursuant to FRCP 12(c), *Masimo Corporation v. Philips Electronics & Philips Electronics North America Corporation, et al.*, Case 1:09-cv-00080-LPS (District of Delaware).
Mar. 13, 2015 [987] Masimo's Opposition to Defendant's Motion for Leave to File Sur-Reply Brief in Opposition to Masimo's Motion for Judgment on the Pleadings Pursuant to FRCP 12(c), *Masimo Corporation v. Philips Electronics & Philips Electronics North America Corporation, et al.*, Case 1:09-cv-00080-LPS (District of Delaware).
Mar. 13, 2015 [987-1] Exhibit 1 to Masimo's Opposition to Defendant's Motion for Leave to File Sur-Reply Brief in Opposition to Masimo's Motion for Judgment on the Pleadings Pursuant to FRCP 12(c), *Masimo Corporation v. Philips Electronics & Philips Electronics North America Corporation, et al.*, Case 1:09-cv-00080-LPS (District of Delaware).
Feb. 26, 2015 [Document 22] Masimo Corporation's Answer and Affirmative Defenses to Counterclaims; Masimo Corporation's Counter-Counterclaims, *Masimo Corporation v. Mindray DS USA, Inc., et al.*, Case 2:15-cv-00457-SDW-SCM (District of New Jersey).
Mar. 19, 2014 [Document 31] Masimo Corporation's Answer and Affirmative Defenses to Counterclaims; Masimo Corporation's First Amended Counter-Counterclaims, *Masimo Corporation v. Mindray DS USA, Inc., et al.*, Case 2:15-cv-00457-SDW-SCM (District of New Jersey).
Feb. 9, 2015 Pretrial Conference—Rule 9 Slides.
Feb. 10, 2015 Grover Kesler Demonstratives, pp. PDX-400-PDX-405.
Feb. 10, 2015 Philips Opening Demonstratives, pp. DDX 0402-0498, *Masimo Corporation v. Philips Electronics & Philips Electronics North America Corporation, et al.*, Case 1:09-cv-00080-LPS (District of Delaware).
Feb. 11, 2015 Jensen Demonstrative, pp. PDX-445, *Masimo Corporation v. Philips Electronics & Philips Electronics North America Corp-oration, et al.*, Case 1:09-cv-00080-LPS (District of Delaware).
Feb. 11, 2015 Masimo Opening Demonstratives, pp. PDX-406-444, *Masimo Corporation v. Philips Electronics & Philips Electronics North America Corporation, et al.*, Case 1:09-cv-00080-LPS (District of Delaware).
Feb. 12, 2015 Masimo Closing Demonstratives, pp. PDX-446-PDX-487, *Masimo Corporation v. Philips Electronics & Philips Electronics North America Corporation, et al.*, Case 1:09-cv-00080-LPS (District of Delaware).
Apr. 15, 2014 Email, DX 2774, *Masimo Corporation v. Philips Electronics & Philips Electronics North America Corporation, et al.*, Case 1:09-cv-00080-LPS (District of Delaware).
Apr. 15, 2014 Email from Steve Jensen to Perry Oldham, DX 2775, *Masimo Corporation v. Philips Electronics & Philips Electronics North America Corporation, et al.*, Case 1:09-cv-00080-LPS (District of Delaware).
May 7, 2014 Email, DX 2776, *Masimo Corporation v. Philips Electronics & Philips Electronics North America Corporation, et al.*, Case 1:09-cv-00080-LPS (District of Delaware).
May 7, 2014 Email, DX 2777, *Masimo Corporation v. Philips Electronics & Philips Electronics North America Corp-oration, et al.* Case 1:09-cv-00080-LPS (District of Delaware).
May 7, 2014 Email, DX 2778, *Masimo Corporation v. Philips Electronics & Philips Electronics North America Corporation, et al.*, Case 1:09-cv-00080-LPS (District of Delaware).
May 7, 2014 Email, DX 2779, *Masimo Corporation v. Philips Electronics & Philips Electronics North America Corporation, et al.*, Case 1:09-cv-00080-LPS (District of Delaware).
May 7, 2014 Email, DX 2780, *Masimo Corporation v. Philips Electronics & Philips Electronics North America Cor~oration, et al.*, Case 1:09-cv-00080-LPS (District of Delaware).
May 7, 2014 Email, DX 2781, *Masimo Corporation v. Philips Electronics & Philips Electronics North America Corporation, et al.*, Case 1:09-cv-00080-LPS (District of Delaware).
May 7, 2014 Email, DX 2785, *Masimo Corporation v. Philips Electronics & Philips Electronics North America Corporation, et al.*, Case 1:09-cv-00080-LPS (District of Delaware).
May 7, 2014 Email, DX 2787, *Masimo Corporation v. Philips Electronics & Philips Electronics North America Corporation, et al.*, Case 1:09-cv-00080-LPS (District of Delaware).
Apr. 15, 2014 Email, DX 2788, *Masimo Corporation v. Philips Electronics & Philips Electronics North America Corporation, et al.*, Case 1:09-cv-00080-LPS (District of Delaware).
Apr. 15, 2014 Email, DX 2789, *Masimo Corporation v. Philips Electronics & Philips Electronics North America Corporation, et al.*, Case 1:09-cv-00080-LPS (District of Delaware).
Apr. 15, 2014 Email, DX 2790, *Masimo Corporation v. Philips Electronics & Philips Electronics North America Corporation, et al.*, Case 1:09-cv-00080-LPS (District of Delaware).
Apr. 15, 2014 Email, DX 2791, *Masimo Corporation v. Philips Electronics & Philips Electronics North America Corporation, et al.*, Case 1:09-cv-00080-LPS (District of Delaware).
Apr. 15, 2014 Email, DX 2792, *Masimo Corporation v. Philips Electronics & Philips Electronics North America Cor~oration, et al.* Case 1:09-cv-00080-LPS (District of Delaware).
Apr. 15, 2014 Email, DX 2793, *Masimo Corporation v. Philips Electronics & Philips Electronics North America Corporation, et al.*, Case 1:09-cv-00080-LPS (District of Delaware).
Apr. 15, 2014 Email, DX 2795, *Masimo Corporation v. Philips Electronics & Philips Electronics North America Corporation, et al.*, Case 1:09-cv-00080-LPS (District of Delaware).
May 7, 2014 Email, DX 2853, *Masimo Corporation v. Philips Electronics & Philips Electronics North America Corporation, et al.*, Case 1:09-cv-00080-LPS (District of Delaware).
Apr. 15, 2014 Email, DX 2854, *Masimo Corporation v. Philips Electronics & Philips Electronics North America Corporation, et al.*, Case 1:09-cv-00080-LPS (District of Delaware).
Apr. 15, 2014 Email, DX 2856, *Masimo Corporation v. Philips Electronics & Philips Electronics North America Corporation, et al.*, Case 1:09-cv-00080-LPS (District of Delaware).
Apr. 2, 2013 Report and Recommendation, DX 2784, *Masimo Corporation v. Philips Electronics & Philips Electronics North America Corporation, et al.*, Case 1:09-cv-00080-LPS (District of Delaware).
Apr. 7, 2014 Memorandum Opinion, DX 2786, *Masimo Corporation v. Philips Electronics & Philips Electronics North America Corporation, et al.*, Case 1:09-cv-00080-LPS (District of Delaware).
Apr. 14, 2014 Letter from David E. Moore to the Honorable Leonard P. Stark, DX 2794, *Masimo Corporation v. Philips Electronics & Philips Electronics North America Corporation, et al.*, Case 1:09-cv-00080-LPS (District of Delaware).
"Fourier Artifact Suppression Technology provides reliable Sp02," DX 2187, *Masimo Corporation v. Philips Electronics & Philips Electronics North America Corporation, et al.*, Case 1:09-cv-00080-LPS (District of Delaware).

(56) References Cited

OTHER PUBLICATIONS

Sep. 7, 2005 Court Decision, *Mallinckrodt, Inc. and Nellcor Puritan Bennett, Inc.*, v. *Masimo Corporation*, DX 2522, *Masimo Corporation* v. *Philips Electronics & Philips Electronics North America Corporation, et al.*, Case 1: 09-cv-00080-LPS (District of Delaware).
Jul. 12, 2004 Memorandum of Decision and Order Re: Post-Trial Motions, *Mallinckrodt, Inc. and Nellcor Puritan Bennett, Inc.* v. *Masimo Corp. and Ivy Biomedical Systems, Inc.*, DX 2712,*Masimo Corporation* v. *Philips Electronics & Philips Electronics North America Corporation, et al.*, Case 1: 09-cv-00080-LPS (District of Delaware).
Dec. 9, 2014 File History for U.S. Appl. No. 90/012,463, DX 2733, *Masimo Corporation* v. *Philips Electronics & Philips Electronics North America Corporation, et al.*, Case 1:09-cv-00080-LPS (District of Delaware).
Dec. 5, 2014 Correspondence Address for U.S. Appl. No. 90/012,463, DX 2734, *Masimo Corporation* v. *Philips Electronics & Philips Electronics North America Corporation, et al.*, Case 1: 09-cv-00080-LPS I(District of Delaware).
Apr. 11, 2014 Masimo Corporation's Statement of Recent Decision by the United States Patent and Trademark Office Confirming the Patentability of Claims 1-5, 15, 16, 19,20,22, and 52-54 of U.S. Pat. No. 7,215,984, *Masimo Corporation* v. *Philips Electronics North America Corporation, et al.*, DX 2851, *Masimo Corporation* v. *Philips Electronics & Philips Electronics North America Corporation, et al.*, Case 1 :09-cv-00080-LPS (District of Delaware).
Mar. 31, 2014 Order, *Masimo Corporation* v. *Philips Electronic North America Corporation, et al.*, DX 2852, *Masimo Corporation* v. *Philips Electronics & Philips Electronics North America Corporation, et al.*, Case 1 :09-cv-00080-LPS (District of Delaware).
Aug. 1, 2014 Third Supplemental Expert Report of Dr. Robert Stone Regarding Invalidity of Masimo Patents-in-Suit (U.S. Pat. No. 6,263,222 and U.S. Pat. No. 7,215,984), DX 3066 (Redacted),*Masimo Corporation* v. *Philips Electronics & Philips Electronics North America Corporation, et al.*, Case 1 :09-cv-00080-LPS (District of Delaware).
Apr. 15, 2014 Email, PTX 9105, *Masimo Corporation* v. *Philips Electronics & Philips Electronics North America Corporation, et al.*, Case 1:09-cv-00080-LPS (District of Delaware).
Apr. 15, 2014 Email, PTX 9106, *Masimo Corporation* v. *Philips Electronics & Philips Electronics North America Corporation, et al.*, Case 1:09-cv-00080-LPS (District of Delaware).
Apr. 15, 2014 Email, PTX 9107, *Masimo Corporation* v. *Philips Electronics & Philips Electronics North America Corporation, et al.*, Case 1:09-cv-00080-LPS (District of Delaware).
Apr. 15, 2014 Email, PTX 9108, *Masimo Corporation* v. *Philips Electronics & Philips Electronics North America Cor~oration, et al.* Case 1 :09-cv-00080-LPS (District of Delaware).
Apr. 15, 2014 Email, PTX 9109, *Masimo Corporation* v. *Philips Electronics & Philips Electronics North America Corporation, et al.*, Case 1:09-cv-00080-LPS (District of Delaware).
Apr. 15, 2014 Email, PTX 9110, *Masimo Corporation* v. *Philips Electronics & Philips Electronics North America Cor~oration, et al.* Case 1 :09-cv-00080-LPS (District of Delaware).
Apr. 15, 2014 Email, PTX 9111, *Masimo Corporation* v. *Philips Electronics & Philips Electronics North America Corporation, et al.*, Case 1:09-cv-00080-LPS (District of Delaware).
May 7, 2014 Email, PTX 9112, *Masimo Corporation* v. *Philips Electronics & Philips Electronics North America Corporation, et al.*, Case 1:09-cv-00080-LPS (District of Delaware).
Apr. 7, 2014 Memorandum Opinion Public Version Released Apr. 7, 2014,*Masimo Corporation* v.*Philips Electronic North America Corporation*, PTX 9113, *Masimo Corporation* v. *Philips Electronics & Philips Electronics North America Corporation, et al.*, Case 1:09-cv-00080-LPS (District of Delaware).
May 7, 2014 Email, PTX 9114, *Masimo Corporation* v. *Philips Electronics & Philips Electronics North America Corporation, et al.*, Case 1:09-cv-00080-LPS (District of Delaware).
May 7, 2014 Email, PTX 9115, *Masimo Corporation* v. *Philips Electronics & Philips Electronics North America Corporation, et al.*, Case 1:09-cv-00080-LPS (District of Delaware).
May 7, 2014 Email, PTX 9116, *Masimo Corporation* v. *Philips Electronics & Philips Electronics North America Corporation, et al.*, Case 1:09-cv-00080-LPS (District of Delaware).
May 7, 2014 Email, PTX 9117, *Masimo Corporation* v. *Philips Electronics & Philips Electronics North America Corporation, et al.*, Case 1:09-cv-00080-LPS (District of Delaware).
May 7, 2014 Email, PTX 9118, *Masimo Corporation* v. *Philips Electronics & Philips Electronics North America Corporation, et al.*, Case 1:09-cv-00080-LPS (District of Delaware).
May 7, 2014 Email, PTX 9119,*Masimo Corporation* v. *Philips Electronics & Philips Electronics North America Corporation, et al.*, Case 1:09-cv-00080-LPS (District of Delaware).
May 7, 2014 Email, PTX 9120, *Masimo Corporation* v. *Philips Electronics & Philips Electronics North America Cor~oration, et al.* Case 1 :09-cv-00080-LPS (District of Delaware).
Apr. 15, 2014 Email, PTX 9121, *Masimo Corporation* v. *Philips Electronics & Philips Electronics North America Corporation, et al.*, Case 1:09-cv-00080-LPS (District of Delaware).
Apr. 15, 2014 Email, PTX 9122, *Masimo Corporation* v. *Philips Electronics & Philips Electronics North America Corporation, et al.*, Case 1:09-cv-00080-LPS (District of Delaware).
U.S. Pat. No. 7,215,984, PTX 0127, *Masimo Corporation* v. *Philips Electronics & Philips Electronics North America Corporation, et al.*, Case 1:09-cv-00080-LPS (District of Delaware).
Feb. 24, 2004 Jury Trial—Day 5, *Maliinckrodt, Inc. et al.* v. *Masimo Corporation*, PTX 9074, *Masimo* v. *Philips Electronics & Philips Electronics North America Corporation, et al.*, Case 1: 09-cv-00080-LPS I(District of Delaware).
May 25, 2010 Proposed Protective Order, *Masimo Corporation* v. *Philips Electronics North America Corporation, et al.*, PTX 9123, *Masimo* v. *Philips Electronics & Philips Electronics North America Corporation, et al.*, Case 1:09-cv-00080-LPS (District of Delaware).
Aug. 28, 2014 Pretrial Conference, *Masimo Corporation* v. *Philips Electronics North America, et al.*, PTX 9142, *Masimo* v. *Philips Electronics & Philips Electronics North America Corporation, et al.*, Case 1:09-cv-00080-LPS (District of Delaware).
Apr. 7, 2014 Letter from Julia Heaney to the Honorable Leonard P. Stark, PTX 9152, *Masimo* v. *Philips Electronics & Philips Electronics North America Corporation, et al.*, Case 1:09-cv-00080-LPS (District of Delaware).
Jul. 7, 2014 Supplemental Expert Report of Professor Gail D. Baura, Ph.D. Concerning the Validity of U.S. Pat. Nos. 6,263,222 and 7,215,984, PTX 9168 Redacted, *Masimo* v. *Philips Electronics & Philips Electronics North America Corporation, et al.*, Case 1:09-cv-00080-LPS (District of Delaware).
Feb. 9, 2015 Transcript of Pretrial Conference (Bench Trial), pp. 1-29, *Masimo* v. *Philips Electronics & Philips Electronics North America Corporation, et al.*, Case 1:09-cv-00080-LPS (District of Delaware).
Feb. 11, 2015 Trial Day 1, vol. A [Opening, Kesler] (Full), *Masimo* v. *Philips Electronics & Philips Electronics North America Corporation, et al.*, Case 1:09-cv-00080-LPS (District of Delaware).
Feb. 12, 2015 Trial Day 2, vol. B [Kesler, Grover, Jensen, Closing] (Full), *Masimo* v. *Philips Electronics & Philips Electronics North America Corporation, et al.*, Case 1:09-cv-00080-LPS (District of Delaware).
Feb. 12, 2015 Philips Closing Inequitable Conduct, pp. DDX 0402-0501, *Masimo* v. *Philips Electronics & Philips Electronics North America Corporation, et al.*, Case 1:09-cv-00080-LPS (District of Delaware).
Feb. 11, 2015 Masimo Opening Demonstratives, pp. PDX-406-PDX-444, *Masimo* v. *Philips Electronics & Philip-s Electronics North America Corp-oration, et al.* Case 1 :09-cv-00080-LPS (District of Delaware).
Sep. 15, 2014 [884] Defendant's Second Amended Answer and Philips Electronics North America Corporation's Third Amended Counterclaims to Masimo's First Amended Complaint, *Masimo* v. *Philips Electronics & Philips Electronics North America Corporation, et al.*, Case 1:09-cv-00080-LPS (District of Delaware).

(56) References Cited

OTHER PUBLICATIONS

Feb. 2, 2015 [953] Proposed Final Pretrial Order (Laches and Inequitable Conduct), *Masimo v. Philips Electronics & Philips Electronics North America Corporation, et al.*, Case 1:09-cv-00080-LPS (District of Delaware).

Nov. 21, 2014 [928] Defendants' Motion for Judgment as a Matter of Law and/or Motion for a New Trial, pp. 1-38, *Masimo v. Philips Electronics & Philips Electronics North America Corporation, et al.*, Case 1:09-cv-00080-LPS (District of Delaware).

Dec. 23, 2014 [939] Masimo Corporation's Opposition to Defendant's Motion for Judgment as a Matter of Law and/or Motion for a New Trial, pp. 1-37, *Masimo Corporation v. Philips Electronics & Philips Electronics North America Corporation, et al.*, Case 1 :09-cv-00080-LPS (District of Delaware).

Jan. 16, 2015 [949] Defendant's Reply Brief in Support of Its Motion for Judgment as a Matter of Law and/or Motion for a New Trial, pp. 1-27, *Masimo Corporation v. Philips Electronics & Philips Electronics North America Corporation, et al.*, Case 1:09-cv-00080-LPS (District of Delaware).

Feb. 18, 2015 Oral Argument Hearing Regarding Post Trial Motion, *Masimo v. Philips Electronics & Philip-s Electronics North America Corp-oration, et al.* Case 1 :09-cv-00080-LPS (District of Delaware).

Feb. 10, 2015 [959] Letter to the Honorable Leonard P. Stark from Julia Heaney Regarding Redacted Expert Reports, *Masimo v. Philips Electronics & Philips Electronics North America Corporation, et al.*, Case 1 :09-cv-00080-LPS (District of Delaware).

Feb. 17, 2015 [965] Redacted [960] Baura Exhibit to [959] Letter to the Honorable Leonard P. Stark from Julia Heaney Regarding Redacted Expert Reports, *Masimo v. Philips Electronics & Philips Electronics North America Corporation, et al.*, Case 1: 09-cv-00080-LPS (District of Delaware).

Feb. 17, 2015 [966] Letter to the Honorable Leonard P. Stark from Julia Heaney Regarding Proposed Post-Trial Briefing, *Masimo v. Philips Electronics & Philips Electronics North America Corporation, et al.*, Case 1:09-cv-00080-LPS (District of Delaware).

Feb. 17, 2015 [967] Letter to the Honorable Leonard P. Stark from David E. Moore Regarding Patent Misuse Defense and Post Trial Briefing, *Masimo v. Philips Electronics & Philips Electronics North America Corporation, et al.*, Case 1:09-cv-00080-LPS (District of Delaware).

Feb. 19, 2015 [Redacted] Shenzhen Mindray's Supplemental Objections and Responses to Masimo Corporation's Second Set of Interrogatories Nos. 6-21, *Masimo Corporation, et al. v. Shenzhen Mindra't Bio-Medical Electronics Co., Ltd.*, Case SACV12-02206 CJC (JPRx) (District of California).

Nov. 13, 2014 [253-1] Joint Stipulation Accompanying Shenzhen Mindray Bio-Medical Electronics Co., Ltd.'s Motion to Compel Production of Documents, *Masimo Corporation, et al. v. Shenzhen Mindray Bio-Medical Electronics Co., Ltd.*, Case SACV12-02206 CJC (JPRx) (District of California).

Nov. 13, 2014 [253-2, 253-3] Declaration of Justin E. Gray in Support of Shenzhen Mindray Bio-Medical Electronics Co., Ltd.'s Motion to Compel Production of Documents Part 1, *Masimo Corporation, et al. v. Shenzhen Mindray Bio-Medical Electronics Co., Ltd.*, Case SACV12-02206 CJC (JPRx) (District of California).

Nov. 13, 2014 [253-2, 253-3] Declaration of Justin E. Gray in Support of Shenzhen Mindray Bio-Medical Electronics Co., Ltd.'s Motion to Compel Production of Documents Part 2, *Masimo Corporation, et al. v. Shenzhen Mindray Bio-Medical Electronics Co., Ltd.*, Case SACV12-02206 CJC (JPRx) (District of California).

Nov. 13, 2014 [253-4] Declaration of Nicholas A. Belair in Opposition to Shenzhen Mindray's Motion to Compel Production of Documents, *Masimo Corporation, et al. v. Shenzhen Mindray Bio-Medical Electronics Co., Ltd.*, Case SACV12-02206 CJC (JPRx) (District of California).

Nov. 20, 2014 [257] Plaintiff Masimo Corporation's Supplemental Memorandum in Opposition to Shenzhen Mindray's Motion to Compel, *Masimo Corporation, et al. v. Shenzhen Mindray Bio-Medical Electronics Co., Ltd.*, Case SACV12-02206 CJC (JPRx) (District of California).

Nov. 20, 2014 [258] Supplemental Memorandum in Support of Shenzhen Mindray Bio-Medical Electronics Co., Ltd.'s Motion to Compel Production of Documents, *Masimo Corporation, et al. v. Shenzhen Mindray Bio-Medical Electronics Co., Ltd.*, Case SACV12-02206 CJC (JPRx) (District of California).

Dec. 4, 2014 [262] Minutes Regarding Hearing on [252] [253] Parties Motions to Compel Production of Documents, *Masimo Corporation, et al. v. Shenzhen Mindray Bio-Medical Electronics Co., Ltd.*, Case SACV12-02206 CJC (JPRx) (District of California).

Dec. 15, 2014 [270] Supplemental Memorandum in Support of Shenzhen Mindray Bio-Medical Electronics Co., Ltd.'s Motion to Compel Production of Documents, *Masimo Corporation, et al. v. Shenzhen Mindray Bio-Medical Electronics Co., Ltd.*, Case SACV12-02206 CJC (JPRx) (District of California).

Dec. 15, 2014 [270-1] Declaration of Justin E. Gray in Support of Shenzhen Mindray's Supplemental Memorandum in Support of Its Motion to Compel Production of Documents, *Masimo Corporation, et al. v. Shenzhen Mindray Bio-Medical Electronics Co., Ltd.*, Case SACV12-02206 CJC (JPRx) (District of California).

Dec. 22, 2014 [273] Masimo Corporation's Supplemental Brief in Opposition to Shenzhen Mindray's Motion to Compel Production of Documents and Things, *Masimo Corporation, et al. v. Shenzhen Mindra'L Bio-Medical Electronics Co., Ltd.*, Case SACV12-02206 CJC (JPRx) (District of California).

Jan. 26, 2015 [301] Minutes Order Denying Mindray Motion to Compel Supplemental Responses to RFPs Nos. 278 and 430, *Masimo Corporation, et al. v. Shenzhen Mindray Bio-Medical Electronics Co., Ltd.*, Case SACV12-02206 CJC (JPRx) (District of California).

Feb. 9, 2015 [310] Shenzhen Mindray Bio-Medical Electronics Co., Ltd.'s Notice of Motion and Motion for Review of the Magistrate Judge's Jan. 26, 2015 Order [Dkt. No. 301], *Masimo Corporation, et al. v. Shenzhen Mindray Bio-Medical Electronics Co., Ltd.*, Case SACV12-02206 CJC (JPRx) (District of California).

Feb. 9, 2015 [310-1] Public Version—Redacted, Memorandum in Support of Shenzhen Mindray's Motion for Review of the Magistrate Judge's Jan. 26, 2015 Order [301],*Masimo Corporation, et al. v. Shenzhen Mindray Bio-Medical Electronics Co., Ltd.*, Case SACV12-02206 CJC (JPRx) (District of California).

Feb. 9, 2015 [310-2] Declaration of Nicola A. Pisano in Support of Shenzhen Mindray's Motion for Review of the Magistrate Judge's Jan. 26, 2015 Order [301], *Masimo Corporation, et al. v. Shenzhen Mindray Bio-Medical Electronics Co., Ltd.*, Case SACV12-02206 CJC (JPRx) (District of California).

Feb. 17, 2015 [326] Masimo Corporation and Masimo International SARL's Opposition to Shenzhen Mindray's Motion for Review of Magistrate Judge's Jan. 26, 2015 Order [301], *Masimo Corporation, et al. v. Shenzhen Mindray Bio-Medical Electronics Co., Ltd.*, Case SACV12-02206 CJC (JPRx) (District of California).

Dec. 10, 2013 Complaint, Demand for Trial by Jury, Designation of Trial Counsel, and Certification Pursuant to Rule 4:5-1, *Masimo Corporation v. Mindray OS USA, Inc., et al.*, (District of New Jersey).

Jan. 22, 2015 Answer and Counterclaims of Mindray DS USA, Inc., *Masimo Corporation v. Mindray DS USA, Inc., et al.*, Case L-9601-13 (District of New Jersey).

A. Cohen et al., "A Light Emitting Diode Skin Reflectance Oximeter," Medical & Biological Engineering. Journal of the International Federation for Medical and Biological Engineering, vol. 10, pp. 385-391, cover page, acknowledgement page, Total pp. 12, 1972.

Answer and Counterclaims of Shenzhen Mindray Bio-Medical Electronics Co., Ltd., D.I. 53, dated May 31, 2013, *Masimo Corp. v. Mindray DS USA, Inc. and Shenzhen Mindray Bio-Medical Elecs. Co., Ltd.* (C.D. Cal. filed Dec. 21, 2012).

Answer and Counterclaims of Shenzhen Mindray Bio-Medical Electronics, Co., Ltd. to Second Amended Complaint, Doc. 241, *Masimo Corporation v. Shenzhen Mindray Bio-Medical Electronics Co., Ltd.*, Case No. SACV12-02206 CJC (JPRx) dated Jul. 24, 2014.

Appendixes for Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated May 7, 2012.

(56) References Cited

OTHER PUBLICATIONS

Blitt, Casey D., *Monitoring in Anesthesia and Critical Care Medicine*, (2d ed. 1990).
Boualem Boashash, *Estimating and Interpreting the Instantaneous Frequency of a Singal—Part I: Fundamentals*, Proceedings of the IEEE, vol. 80, No. 4 (Apr. 1992).
Boualem Boashash, *Note on the Use of the Wigner Distribution for Time-Frequency Signal Analysis*, IEEE Transactions on Acoustics, Speech, and Signal Processing, vol. 36, No. 9 (Sep. 1988).
Business Wire, "Mallinckrodt Announces the Nellcor N-395 Pulse Oximeter With Oxismart XL and SatSeconds," Oct. 7, 1999.
Edward Bedrosian, *The Analytic Signal Representation of Modulating Waveforms* (1962).
Braun, S., et al., "*Mechanical Signature Analysis Theory and Applications*," pp. 142-145, 202-203 (1986).
Brown, David, P. "Evaluation of Pulse Oximeters using Theoretical Models and Experimental Studies" Masters Thesis, University of Washington, 1987.
Bruce H. McCormick et al., "Computer Eye Looks at Human Eye", p. 687-697.
C. Zamarron et al., "Oximetry spectral analysis in the diagnosis of obstructive sleep apnoea," The Biochemical Society and the Medical Research Society, 1999, pp. 467-473.
Chen, J., et al., "Adaptive System for Processing of Electrogastric Signals," *Images of the Twenty-First Centry*, vol. 11, pp. 698-699, Seattle, WA, Nov. 9-12, 1989.
Cohen, Arnon Ph.D., "vol. I: Time and Frequency Domains Analysis", Biomedical Signal Processing, CRC Press, Inc., pp. 152-159.
Complaint for Patent Infringement, *Masimo Corporation v. Philips Electronics North America Corporation and Philips Medizin Systeme Boblingen GmbH*, (District of Delaware, Case No. 09-000080(JJF)), dated Feb. 3, 2009.
Complaint, D.I. 1, dated Dec. 21, 2012, *Masimo Corp. v. Mindray DS USA, Inc. and Shenzhen Mindray Bio-Medical Elecs. Co., Ltd.* (C.D. Cal. filed Dec. 21, 2012).
Copending U.S. Appl. No. 10/006,427, published on Jun. 20, 2002, as U.S. Pub No. US2002/0077536 A1.
Copending U.S. Appl. No. 10/005,631, filed Dec. 4, 2001, and pending claims.
Copending U.S. Appl. No. 10/062,859, published on Sep. 12, 2002, as U.S. Pub. No. US2002/128544-A1.
Copending U.S. Appl. No. 09/195,791, filed Nov. 17, 1998, and pending claims.
Deborah S. Bland, RN, "Pulse Oximetry, Monitoring Arterial Hemoglobin Oxygen Saturation," Aorn Journal, Apr. 1987, vol. 45, No. 4, pp. 964-967, cover page, gen info page, Total pp. 5.
Declaration of Clark R. Baker, dated Aug. 15, 2000, Trial Exhibit JTX-1133,*Masimo Corp. v. Mallinckrodt, Inc.*, SA-CV-99-1245-AHS-ANX (C.D. Cal.).
Declaration of Gail Baura, Ph.D. in Support of Masimo's Opposition to Defendant's Motion for Summary Judgment of Invalidity of U.S. Pat. No. 5,632,272, Doc. 554, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Gail Baura, Ph.D. in Support of Masimo's Opposition to Defendant's Motion for Summary Judgment of Invalidity of U.S. Pat. No. 6,263,222, Doc. 551, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Gail Baura, Ph.D. in Support of Masimo's Opposition to Defendant's Motion for Summary Judgment of Invalidity of U.S. Pat. No. 6,699,194, Doc. 508, *Masimo Corporation v. Philips Electronics North America Corporation and Philips Medizin Systeme Böblingen GMBH*, (District of Delaware, Case No. 1:09-cv-00080 (LPS/MPT) dated Sep. 21, 2012.
Declaration of Gail Baura, Ph.D. in Support of Masimo's Opposition to Defendant's Motion for Summary Judgment of Invalidity of U.S. Pat. No. 7,215,984, Doc. 561, *Masimo Corporation v. Philips Electronics North America Corporation and Philips Medizin Systeme Böblingen GMBH*, (District of Delaware, Case No. 1:09-cv-00080 (LPS/MPT,) dated Sep. 28, 2012. (Redacted).
Declaration of Mohammed K. Diab in Support of Masimo's Oppositions to Defendants' Motions for Summary Judgment of Invalidity and Noninfringement of U.S. Pat. Nos. 5,632,272 and 7,215,984, Doc. 563, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012 (Redacted).
Declaration of Nicola A. Pisano in Support of Shenzhen Mindray's Opposition to Masimo's Motion for Partial Judgment on the Pleadings, Doc. 109-1, *Masimo Corporation v. Shenzhen Mindray Bio-Medical Electronics Co., Ltd.*, Civil Action No. SACV12-02206 CJC (JPRx) dated Feb. 3, 2014.
Declaration of Perry D. Oldham in Support of Masimo Opposition to Defendant's Motion for Summary Judgment of Invalidity of U.S. Pat. No. 5,632,272, Doc. 553, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Perry D. Oldham in Support of Masimo's Opposition to Defendant's Motion for Summary Judgment of Invalidity of U.S. Pat. No. 6,263,222, Doc. 550, *Masimo Corporation v. Philips Electronics North America Corporation and Philips Medizin Systeme Böblingen GMBH*, (District of DelawareCase No. 1:09-cv-00080 (LPS/MPT) dated Sep. 28, 2012 (Redacted).
Declaration of Perry D. Oldham in Support of Masimo Opposition to Defendant's Motion for Summary Judgment of Invalidity of U.S. Pat. No. 6,699,194, Doc. 548, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Perry D. Oldham in Support of Masimo Opposition to Defendant's Motion for Summary Judgment of Invalidity and Noninfringement of U.S. Pat. No. 7,215,984, vol. 1, Doc. 556, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Perry D. Oldham in Support of Masimo's Opposition to Defendant's Motion for Summary Judgment of Invalidity and Noninfringement of U.S. Pat. No. 7,215,984, vol. 2, Doc. 558, *Masimo Corporation v. Philips Electronics North America Corporation and Philips Medizin Systeme Böblingen GMBH*, (District of Delaware, Case No. 1:09-cv-00080 (LPS/MPT) dated Sep. 28, 2012. (Redacted).
Declaration of Stephen W. Larson in Support of Masimo Corporation's Motion for Judgment on the Pleadings, Doc. 107-2, *Masimo Corporation v. Shenzhen Mindray Bio-Medical Electronics Co., Ltd.*, Civil Action No. SACV12-02206 CJC (JPRx) dated Jan. 27, 2014.
Declaration of Thomas J. Yorkey, dated Aug. 20, 2000, Trial Exhibit JTX-1134, *Masimo Corp. v. Mallinckrodt, Inc.*, SA-CV-99-1245-AHS-ANX (C.D. Cal.).
Defendants' Answer and Philips Electronics North America Corp.'s Counterclaims to Masimo's First Amended Complaint, Doc. 11, *Masimo Corporation v. Philips Electronics North America Corporation and Philips Medizin Systeme Böblingen GMBH*, (District of Delaware, Case No. 1:11-cv-00742 (LPS/MPT) dated Nov. 7, 2011.
Defendants' Answer and Philips Electronics North America Corp.'s Counterclaims to Masimo's Second Amended Complaint, Doc. 43, *Masimo Corporation v. Philips Electronics North America Corporation and Philips Medizin Systeme Böblingen GMBH*, (District of Delaware, Case No. 1:11-cv-00742 (LPS/MPT) dated May 11, 2012.
Defendant/Counterclaim-Plaintiff Philips Electronics North America Corporation Answer to Masimo's Counterclaims, *Masimo Corporation v. Philips Electronics North America Corporation and Philips Medizin Systeme Boblingen GmbH*, (District of Delaware, Case No. 09-00080(JJF)) dated Aug. 3, 2009, pp. 1-23.
Defendants' Answer and Philips Electronics North America Corporation's Counterclaims to Masimo's First Amended Complaint, *Masimo Corporation v. Philips Electronics North America Corpo-

(56) References Cited

OTHER PUBLICATIONS ration and Philips Medizin Systeme Boblingen GmbH, (District of Delaware, Case No. 09-00080(JJF)) dated Jun. 5, 2009.
Defendants' Answer and Philips Electronics North America Corporation's Amended Counterclaims to Masimo' s First Amended Complaint, *Masimo Corporation v. Philips Electronics North America Corporation and Philips Medizin Systeme Boblingen GmbH*, (District of Delaware, Case No. 09-00080(JJF)) dated Apr. 21, 2010.
Defendants' First Amended Answer and Philips Electronics North America Corporation's Second Amended Counterclaims to Masimo's First Amended Complaint, Doc. 855, *Masimo Corporation v. Philips Electronics North America Corporation and Philips Medizin Systeme Böblingen GMBH*, (District of Delaware, Case No. 1:09-cv-00080 (LPS/MPT,) dated Sep. 3, 2014.
Defendants' Motion for Reargument Regarding the Order Overruling Philips' Objection that Claims 15, 16, 19, 20, 53, and 54 of U.S. Pat. No. 7,215,984 Are Not Infringed, Doc. 792, *Masimo Corporation v. Philips Electronics North America Corporation and Philips Medizin Systeme Böblingen GMBH*, (District of Delaware, Case No. 1:09-cv-00080 (LPS/MPT) dated Apr. 25, 2014. (Redacted).
Defendants' Motion for Summary Judgment of Invalidity and Noninfringement of U.S. Patent No. 5, 632, 272, Doc. 402, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Defendants' Motion for Summary Judgment of Invalidity of U.S. Pat. No. 6,263,222, Doc. 410, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Defendants' Motion for Summary Judgment of Invalidity of U.S. Pat. No. 6,699,194, Doc. 406, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Defendants' Objections to Magistrate Judge Thynge's Report and Recommendation Regarding Claim Construction, Doc. 218, *Masimo Corporation v. Philips Electronics North America Corporation and Philips Medizin Systeme Böblingen GMBH*, (District of Delaware, Case No. 1:09-cv-00080 (LPS/MPT) dated Mar. 7, 2011.
Defendants' Objections to Magistrate Judge Thynge's Apr. 2, 2013 Report and Recommendation Regarding Philips'Motions for Summary Judgment, *Masimo Corporation v. Philips Electronics North America Corporation and Philips Medizin Systeme Böblingen GMBH*, (District of Delaware, Case No. 109-cv-00080(LPS/MPT) dated Apr. 26, 2013. (Redacted).
Defendants' Opposition to Masimo's Motion for Reconsideration of the Court's Order and Memorandum Opinion Regarding U.S. Pat. No. 5,632,272, Doc. 798, *Masimo Corporation v. Philips Electronics North America Corporation and Philips Medizin Systeme Böblingen GMBH*, (District of Delaware, Case No. 1:09-cv-00080 (LPS/MPT) dated May 5, 2014. (Redacted).
Defendants' Reply Brief in Support of Its Motion for Leave to Amend Its Answer, Doc. 811, *Masimo Corporation v. Philips Electronics North America Corporation and Philips Medizin Systeme Böblingen GMBH*, (District of Delaware, Case No. 1:09-cv-00080 (LPS/MPT) dated Jun. 19, 2014.
Defendants' Response to Masimo Corporation's Objections to Magistrate Judge Thynge's Apr. 2, 2013 Report and Recommendation Regarding Summary Judgment, Doc. 696, *Masimo Corporation v. Philips Electronics North America Corporation and Philips Medizin Systeme Böblingen GMBH*, (District of Delaware, Case No. 1:09-cv-00080 (LPS/MPT) dated May 13, 2013. (Redacted).
Defendant Shenzhen Mindray's First Set of Requests for Admission (Nos. 1-32), *Masimo Corporation v. Shenzhen Mindray Bio-Medical Electronics Co., Ltd.*, Civil Action No. SACV12-02206 CJC (JPRx) dated Jun. 25, 2014.

Defendant Shenzhen Mindray's Second Set of Interrogatories to Plaintiff (Nos. 22-25), *Masimo Corporation v. Shenzhen Mindray Bio-Medical Electronics Co., Ltd.*, Civil Action No. SACV12-02206 CJC (JPRx) dated Jun. 25, 2014.
Deposition of Ibrahim Elfadel taken Nov. 23, 2010, *Masimo Corporation v. Philips Electronics North America Corporation and Philips Medizin Systeme Boblingen GmbH*, (District of Delaware, Case No. I :09-cv-00080 (LPS/MPT). (Redacted).
Deposition of Joe Kiani taken Apr. 6, 2011, *Masimo Corporation v. Philips Electronics North America Corporation and Philips Medizin Systeme Boblingen GmbH*, (District of Delaware, Case No. 1:09-cv00080 (LPSIMPT) (Redacted).
Deposition of Joe Kiani taken Apr. 7, 2011, *Masimo Corporation v. Philips Electronics North America Corporation and Philips Medizin Systeme Boblingen GmbH*, (District of Delaware, Case No. 1:09-cv00080 (LPS/MPT) (Redacted).
Deposition of Joe Kiani taken Sep. 27, 2011, *Masimo Corporation v. Philips Electronics North America Corporation and Philips Medizin Systeme Boblingen GmbH*, (District of Delaware, Case No. I :09-cv-00080 (LPS/MPT) (Redacted).
Deposition of Mohammed Diab taken Feb. 3, 2011, *Masimo Corporation v. Philips Electronics North America Corporation and Philips Medizin Systeme Boblingen GmbH*, (District of Delaware, Case No. 1:09-cv-00080 (LPS/MPT). (Redacted).
Deposition of Rex McCarthy taken Nov. 3, 2010, *Masimo Corporation v. Philips Electronics North America Corporation and Philips Medizin Systeme Boblingen GmbH*, (District of Delaware, Case No. 1:09-cv-00080 (LPS/MPT). (Redacted).
Deposition of Robert Smith taken Dec. 7, 2010, *Masimo Corporation v. Philips Electronics North America Corporation and Philips Medizin Systeme Boblingen GmbH*, (District of Delaware, Case No. 1:09-cv-00080 (LPS/MPT). (Redacted).
Deposition of Walter Weber taken Dec. 8, 2010, *Masimo Corporation v. Philips Electronics North America Corporation and Philips Medizin Systeme Boblingen GmbH*, (District of Delaware, Case No. I :09-cv-00080 (LPS/MPT) (Redacted).
Deposition of Walter Weber taken Dec. 9, 2010, *Masimo Corporation v. Philips Electronics North America Corporation and Philips Medizin Systeme Boblingen GmbH*, (District of Delaware, Case No. I :09-cv-00080 (LPS/MPT) (Redacted).
Doblar, D.O. et al., "Dynamic Characteristics of Cerebral Blood Flow Response to Sinusoidal Hypoxia," American Physiological Society, 1979, pp. 721-729.
E. M. Sevick et al., "Quantitation of Time- and Frequency-Resolved Optical Spectra for the Determination of Tissue Oxygenation," Analytical Biochemistry 195, pp. 330-351.
Excerpts from the Transcript of Record, testimony of Dr. Robert Stone, pp. 1696-1699, 1780-1795, *Mallickrodt, Inc. v Masimo Corp.*, No. cv-00-6506-MRP (C.D. Cal.).
Excerpts from the Transcript of Record, testimony of Dr. Robert Stone, pp. 1796-1799, 1812-1884, *Mallickrodt, Inc. v Masimo Corp.*, No. cv-00-6506-MRP (C.D. Cal.).
Exhibit 2035 Stone, *Masimo Corporation v. Philips Electronics North America Corporation et al*, Case 1:09-cv-00080-LPS (District of Delaware).
Exhibits A-G for Masimo Corporation's Objections to the Report and Recommendation Regarding Summary Judgment, *Masimo Corporation v. Philips Electronics North America Corporation and Philips Medizin Systeme Böblingen GMBH*, (District of Delaware, Case No. 1:09-cv-00080 (LPS/MPT) dated Apr. 26, 2013. (Redacted).
Expert Report of Dr. Robert Stone Regarding the invalidity of Masimo's Patents-in-Suit (U.S. Pat. No. 5, 632, 272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated May 7, 2012.
F.F. Jobsis, "Noninvasive, Infrared Monitoring of Cerebral and Myocardial Oxygen Sufficiency and Circulatory Parameters," Science, vol. 198, No. 4323, Dec. 23, 1977, pp. 1264-1267, table of contents pp. 2, Total pp, 6.
Farid U. Dowlaet al., "Neural Networks and Wavelet Analysis in the Computer Interpretation of Pulse Oximetry Data," pp. 527-536, 1996, Oct. 29, 1990.

(56) References Cited

OTHER PUBLICATIONS

"FAST-Sp02 Motion-tolerant pulse oximetry with maximum sensor flexibility," Phillips Medical Systems, pp. 1-2, 2003.
Fast-Sp02 Pulse oximetry, printed from http://www.medical.philips.corn/main/products/patient_monitoringlproducts/fast_sp02/in on Oct. 30, 2006, pp. 1-3.
Felix W. Leung, MD. et al., "Gastroduodenal mucosal hemodynamics by endoscopic reflectance spectrophotometry," Gastrointestinal Endoscopy, 1987, vol. 33, No. 4, Aug. 1987, pp. 284-288, table of contents page, Total pp. 6.
Ferrara, E.R., "Fetal Electrocardiogram Enhancement by Time-Sequenced Adaptive Filtering," *IEEE Transactions on Biomedical Engineering*, vol. BME-29, No. 6, Jun. 1982.
Findings of Fact and Conclusion of Law Regarding Masimo's Motion for Preliminary Injunction, *Masimo v. Mallinckrodt Inc., et al.*, U. S. Distrcit Court, Central District of California (Southern Division), Civil Action No. SA-CV-99/1245 AHS (Anx), filed Nov. 2, 2000 (Redacted).
First Amended Complaint for Patent Infringement, *Masimo Corporation v. Philips Electronics North America Corporation and Philips Medizin Systeme Boblingen GmbH*, (District of Delaware, Case No. 09-00080(JJF)) dated May 12, 2009.
Glover, Jr., J.R., "Adaptive Noise Canceling of Sinussoidal interferences," A Dissertation Submitted to the Department of Electrical Engineering and the Committee on Graduate Studies of Stanford University in Partial Fulfillment of the Requirements for the Degree of Doctor of Philosophy, pp. iii-82 (1975).
H.S. Lim et al., "The Study of Signal Processing Method in Frequency Domain for Measuring Oxygen Saturation in Biological Tissue," pp. 527-530, 2000.
Hanson, P.G. et al., "Influence of Breathing Pattern on Oxygen Exchange During Hypoxia and Exercise," Journal of Applied Physiology, Jun. 1975, vol. 38, No. 6.
Hanzo et al., *A Portable Multimedia Communicator Scheme*, Multimedia Technologies and Future Applications: Proceedings of the IEEE International Symposium (1994).
Harris, et al., "*Digital Signal Processing with Efficient Polyphase Recursive All-Pass Filter*," International Conference, Florence, Italy, (Sep. 26, 1991).
Haykin, Simon, Adaptive Filter Theory, Prentice Hall, Englewood Cliffs, NJ, 1985.
Haykin, Simon, Adaptive Filter Theory, Prentice Hall, Englewood Cliffs, NJ, 1985, Chapter 9, "Recursive Least-Squares Lattice Filters," pp. 451-493, 1985.
Hendry, S.D., "Computation of Harmonic Comb Filter Weights," *IEEE Transactions on Signal Processing*, vol. 41, No. 4, Apr. 1993.
Hiramoto, J. et al., "Tissue Spectrum Analyzer for Medical Use," Review of Laser Engineering, 1985, vol. 13, No. 2, pp. 165-170.
History of Blood Gas Analysis, VII. Pulse Oximetry, Severinghaus, et al., Journal of Clinical Monitoring, vol. 3, No. 2. Apr. 1987.
J.C. Dories et al., "Pulse Oximetry-principles and first experiences during anesthesia," Acta Anaesthesiolgica Belgica, 1987,38, No. 2. pp. 133-138,Cover page, table of contents pp. 1-4, Total pp 10.
J.M. Kim, et al., "Signal Processing Using Fourier & Wavelet Transform for Pulse Oximery," pp. 310-311.
Jingzheng, O., et al., "Digital Processing of High-Resolution Electrocardiograms—Detection of His Purkinje Activity From the Body Surface," *Biomedizinische Technik*, vol. 33, No. 10, pp. 224-230, Berlin, Germany, Oct. 1, 1988.
Joachim S. Gravestein, MD., "Sampling Intervals for Clinical Monitoring of Variables During Anesthesia," Journal of Clinical Monitoring, vol. 5. No. 1. Jan. 1989, pp. 17-21, cover page, Total pp. 6.
Joseph M. Schmitt et al., "An Integrated Circuit-Based Optical Sensor for In Vivo Measurement of Blood Oxygenation," IEEE Transactions on Biomedical Engineering, vol. BME-33, No. 2, Feb. 1986, pp. 98-107.
Kamata, T. et al., "In Vivo Analysis of Hepatic Hemodynamics by Reflectance Spectrophotometry," Kan, Tan, Sui, 1986, vol. 12, No. 5, pp. 725-730.
Karen Riedel, RN, "Pulse oximetry: A new thechnology to assess patient oxygen needs in the neonatal intensive care unit", The Journal of Perinatal and Neonatal Nursing, Jul. 1987, pp. 49-57, cover pages, Total pp. 11.
Kent K. Gillingham et al., "Transfer Functions for Arterial Oxygen Saturation During +Gz Stress," Aviation Space and Environmental Medicine, vol. 46, No. 11. Nov. 1975, pp. 1329-1335.
Klimasauskas, Casey, "Neural Nets and Noise Filtering" Article, Dr. Dobb's Journal, Jan. 1989, pp. 32-34, 36-38, 42, 47, 49, 96, 98, 100.
Leon Bennett, Mae, "Spectrum Analysis of Large Toe Plethysmographic Waveshape," Arch Phys Med. Rehabil. vol. 66, May 1985, pp. 280-285.
Li, G., "A Stable and Efficient Adaptive Notch Filter for Direct Frequency Estimation," *IEEE Transactions on Signal Processing*, vol. 45, No. 8, Aug. 1987.
Lisbet Jansson et al., "Noise Reduction of ECG by Averaging—An Experimental Study of the Procedure and a Validated Method," pp. 781-787,1975.
Lloyd A. Marks, "Digital Enhancement of the Peripheral Admittance Plethysmogram," IEEE Transactions on Biomedical Engineering, vol. BME-34, No. 3, Mar. 1987, p. 192-198.
M. Brunner et al., "Some Aspects of Signal Analysis Applied to Intracapillary Hemoglobin Spectra," pp. 803-810.
M. Brunner, "Measurements and Processing of Intra capillary Hemoglobin Spectra by Using a Micro-Lightguide Spectrophotometer in Connection with a Microcomputer," pp. 909-916.
M.B. Taylor et al., "The current status of pulse oximetry-Clinical value of continuous noninvasive oxygen saturation monitoring," Anesthesia, 1986, vol. 41, pp. 943-949, Contents page, Total pp. 8.
Maciej Niedzwiecki et al. "Smoothing of Discontinuous Signals: The Competitive Approach," *IEEE Transactions on Signal Processing*, vol. 43, No. 1, Jan. 1995, pp. 1-13.
Makino, M. et al., "Spectrophotometric Detennination of Oxygen Saturation in Blood," The Japanese Journal of Clinical Pathology, 1986, vol. 16, No. 8, pp. 647-650.
*Mallinckrodt, Inc. v. Masimo Corp.*, 147 F. App'x 158 (Fed. Cir. Sep. 7, 2005).
*Mallinckrodt inc. v. Masimo Corp.*, 2004 U.S. Dist. Lexis 28518 (C.D. Cal. Jul. 12, 2004).
*Masimo Corp v. Mallinckrodt, Inc.*, 18 F. App'x 852 (Fed. Cir. Aug. 8, 2001).
Masimos Answer to Philips' Amended Counterclaims, *Masimo Corporation v. Philips Electronics North America Corpora/ion and Philips Medizin Systeme Boblingen GmbH*, (District of Delaware, Case No. 09-00080(JJF) dated May 10, 2010.
Masimo's Answer to Phil ips' Counterclai ms, *Masimo Corporation v. Philips Electronics North America Corporation and Philips Medizin Systeme Boblingen GmbH*, (District of Delaware, Case No. 09-00080(JJF)) dated Jul. 9, 2009.
Masimo's Answer to Philips' Counterclaims, Doc. 28, *Masimo Corporation v. Philips Electronics North America Corporation and Philips Medizin Systeme Böblingen GMBH*, (District of Delaware, Case No. 1:11-cv-00742 (LPS/MPT) dated Dec. 30, 2011.
Masimo's Answer to Philips' Counterclaims to Masimo's Second Amended Complaint, Doc. 358, *Masimo Corporation v. Philips Electronics North America Corporation and Philips Medizin Systeme Böblingen GMBH*, (District of Delaware, Case No. 1:11-cv-00742 (LPS/MPT) dated Jun. 4, 2012.
Masimo Corporation's and Masimo International SARL's Reply to Shenzhen Mindray Bio-Medical Electronics Co., Ltd.'s Answer and Counterclaims; Masimo Corporation's Counter-claims, Doc. 244, *Masimo Corporation v. Shenzhen Mindray Bio-Medical Electronics Co., Ltd.*, CV SACV12-02206 CJC (JPRx) dated Aug. 7, 2014.
Masimo Corporation's Answering Brief in Opposition to Defendant's Motion for Summary Judgment of Invalidity and Noninfringement of U.S. Pat. No. 5,632,272, Doc. 552, *Masimo Corporation v. Philips Electronics North America Corporation and Philips Medizin Systeme Böblingen GMBH*, (District of Delaware Case No. 1:09-cv-00080 (LPS/MPT) dated Sep. 28, 2012. (Redacted).
Masimo Corporation's Answering Brief in Opposition to Defendants' Motion for Summary Judgment of Invalidity of U.S. Pat. No. 6,263,222, Doc. 549, *Masimo Corporation v. Philips Electronics*

(56) References Cited

OTHER PUBLICATIONS

*North America Corporation and Philips Medizin Systeme Böblingen GMBH*, (District of Delaware, Case No. 1:09-cv-00080 (LPS/MPT) dated Sep. 28, 2012 (Redacted).

Masimo Corporation's Answering Brief in Opposition to Defendant's Motion for Summary Judgment of Invalidity and Noninfringement of U.S. Pat. No. 7,215,984, Doc. 555, *Masimo Corporation v. Philips Electronics North America Corporation and Philips Medizin Systeme Böblingen GMBH*, (District of Delaware, Case No. 1:09-cv-00080 (LPS/MPT,) dated Sep. 28, 2012. (Redacted).

Masimo Corporation's Memorandum of Points and Authorities in Support of Motion for Judgment on the Pleadings, Doc. 107-1, *Masimo Corporation v. Shenzhen Mindray Bio-Medical Electronics Co., Ltd.*, Civil Action No. SACV12-02206 CJC (JPRx) dated Jan. 27, 2014.

Masimo Corporation's Notice of Motion and Motion for Judgment on the Pleadings, Doc. 107, *Masimo Corporation v. Shenzhen Mindray Bio-Medical Electronics Co., Ltd.*, Civil Action No. SACV12-02206 CJC (JPRx) dated Jan. 27, 2014.

Masimo Corporation's Objections to the Report and Recommendation Regarding Claim Construction, Doc. 219, *Masimo Corporation v. Philips Electronics North America Corporation and Philips Medizin Systeme Böblingen GMBH*, (District of Delaware, Case No. 1:09-cv-00080 (LPS/MPT) dated Mar. 8, 2011.

Masimo Corporation's Objections to the Report and Recommendation Regarding Philips' Motions for *Masimo Corporation v. Philips Electronics North America Corporation and Philips Medizin Systeme Böblingen GMBH*, (District of Delaware, Case No. 1:09-cv-00080 (LPS/MPT) dated Apr. 26, 2013. (Redacted).

Masimo Corporation's Opposition to Defendants' Motion for Reargument Regarding the Order Overruling Philips' Objection that Claims 15, 16, 19, 20, 53, and 54 of U.S. Pat. No. 7,215,984 Are Not Infringed, Doc. 797, *Masimo Corporation v. Philips Electronics North America Corporation and Philips Medizin Systeme Böblingen GMBH*, (District of Delaware, Case No. 1:09-cv-00080 (LPS/MPT) dated May 5, 2014. (Redacted).

Masmio Corporation's Opposition to Philipls' Motion for Leave to File First Amended Answer and Second Amended Counterclaims, Doc. 807, *Masimo Corporation v. Philips Electronics North America Corporation and Philips Medizin Systeme Böblingen GMBH*, (District of Delaware, Case No. 1:09-cv-00080 (LPS/MPT) dated Jun. 9, 2014.

Masimo Corporation's Response to Defendants' Objections to the Report and Recommendation Regarding Claim Construction, Doc. 232, *Masimo Corporation v. Philips Electronics North America Corporation and Philips Medizin Systeme Böblingen GMBH*, (District of Delaware, Case No. 1:09-cv-00080 (LPS/MPT) dated Mar. 24, 2011.

Masimo Corporation's Responses to Shenzhen Mindray's First Set of Requests for Admission to Plaintiff (Nos. 1-32), *Masimo Corporation v. Shenzhen Mindray Bio-Medical Electronics Co., Ltd.*, Case No. SACV12-02206 CJC (JPRx) dated Jul. 25, 2014.

Masimo Corporation's Response to Philips' Objections to the Apr. 2, 2013 Report and Recommendation Regarding Summary Judgment, Doc. 697, *Masimo Corporation v. Philips Electronics North America Corporation and Philips Medizin Systeme Böblingen GMBH*, (District of Delaware, Case No. 1:09-cv-00080 (LPS/MPT) dated May 13, 2013. (Redacted).

Masimo Corporation's Second Set of Interrogatories to Shenzhen Mindray Biomedical Electronics Co., Ltd (Nos. 6-21), *Masimo Corporation v. Shenzhen Mindray Bio-Medical Electronics Co., Ltd*, Civil Action No. SACV12-02206 CJC (JPRx) dated Apr. 17, 2014.

Masimo Corporation's Statement of Recent Decision by the United States Patent and Trademark Office Confirming the Patentability of Claims 1-5, 15, 16, 19, 20, 22, and 52-54 of U.S. Pat. No. 7,215,984, Doc. 783, *Masimo Corporation v. Philips Electronics North America Corporation and Philips Medizin Systeme Böblingen GMBH*, (District of Delaware, Case No. 1:09-cv-00080 (LPS/MPT) dated Apr. 11, 2014.

Masimo's Letter to the Court Including Slides from Dr. Rosenthal Regarding U.S. Pat. No. 7,215,984, Doc. 850, *Masimo Corporation v. Philips Electronics North America Corporation and Philips Medizin Systeme Böblingen GMBH*, (District of Delaware, Case No. 1:09-cv-00080 (LPS/MPT) dated Aug. 28, 2014.

Masimo's Letter to the Court Including a Timeline Regarding U.S. Pat. No. 7,215,984, Doc. 851, *Masimo Corporation v. Philips Electronics North America Corporation and Philips Medizin Systeme Böblingen GMBH*, (District of Delaware, Case No. 1:09-cv-00080 (LPS/MPT) dated Aug. 28, 2014.

Masimo's Letter to the Court Regarding Philips' Motion for Leave to Amend Its Answer, Doc. 852, *Masimo Corporation v. Philips Electronics North America Corporation and Philips Medizin Systeme Böblingen GMBH*, (District of Delaware, Case No. 1:09-cv-00080 (LPS/MPT) dated Aug. 29, 2014.

Masimo's Reply in Support of its Motion for Judgment on the Pleadings, Doc. 110, *Masimo Corporation v. Shenzhen Mindray Bio-Medical Electronics Co., Ltd.*, Civil Action No. SACV12-02206 CJC (JPRx) dated Feb. 10, 2014.

Matthew James Hayes et al., "A New Method for Pulse Oximetry Possessing Inherent Insensitivity to Artifact," IEEE Transactions on Biomedical Engineering, vol. 48, No. 4., Apr. 2001, pp. 452-461.

Melnikof, Steve, "Neural Networks for Signal Processing: A Case Study" Article, Dr. Dobb's Journal, Jan. 1989, pp. 36-37.

Memorandum of Decision and Order Re: Claim Construction; Motion to Strike Masimo's Declarations dated Feb. 27, 2003.

Memorandum Order Adopting Report and Recommendation Regarding Claim Construction, Doc. 319, *Masimo Corporation v. Philips Electronics North America Corporation and Philips Medizin Systeme Böblingen GMBH*, (District of Delaware, Case No. 1:09-cv-00080 (LPS/MPT) dated Jan. 17, 2011.

Memorandum Order, Doc. 787, *Masimo Corporation v. Philips Electronics North America Corporation and Philips Medizin Systeme Böblingen GMBH*, (District of Delaware, Case No. 1:09-cv-00080 (LPS/MPT) dated Apr. 14, 2014.

Memorandum Order, Doc. 815, *Masimo Corporation v. Philips Electronics North America Corporation and Philips Medizin Systeme Böblingen GMBH*, (District of Delaware, Case No. 1:09-cv-00080 (LPS/MPT) dated Jul. 2, 2014.

Memorandum Order, Doc. 854, *Masimo Corporation v. Philips Electronics North America Corporation and Philips Medizin Systeme Böblingen GMBH*, (District of Delaware, Case No. 1:09-cv-00080 (LPS/MPT) dated Sep. 2, 2014.

Michael W. Wukitsch et al., "Knowing Your Monitoring Equipment," Journal of Clinical Monitoring, vol. 4. No. 4, Oct. 1988, pp. 290-301, cover page, Total pp. 13.

Min, B.G., et al., "*Frequency-Domain Analysis of Oxygen Stores During Hypoxia in the Goal*," Annals of Biomedical Engineering, vol. 6 No. 4.

Mook, G.A., et al., "Spectrophotometric determination of oxygen saturation of blood independent of the presence of indocyanin green", Cardiovascular Research, vol. 13, 1979, pp. 233-237.

Mook, G.A., et al., "Wavelength dependency of spectrophotometric determination of blood oxygen saturation", Clinical Chemistry Acta, vol. 26, 1969, pp. 170-173.

Nehorai, A., "A Minimal Parameter Adaptive Notch Filter With Constrained Poles and Zeros," *IEE Transactions on Acoustics, Speech, and Signal Processing*, vol. ASSP-33, No. 4, Aug. 1985.

Nehorai, A., "Adaptive Comb Filtering for Harmonic Signal Enhancement," *IEEE Transactions on Acoustics, Speech, and Signal Processing*, vol. ASSP-34, No. 5, Oct. 1986.

Nellcor's and Mallinckrodt's Amended and Supplemental Answer and Counterclaims to Masimo Corporation's First Amended Complaint in Case No. CV-01-7293-MRP (AJWx).

Nellcor's and Mallinckrodt's Amended Complaint for Patent Infringement.

Nellcor's and Mallinckrodt's First Amended and Supplemental Reply and Counterclaims to Counterclaims of Masimo Corporation.

Nellcor's and Mallinckrodt's Opening Claim Construction Brief on the Patents-In-Suit dated Sep. 16, 2002.

Nelleor's and Mallinckrodt's Reply Claim Construction Brief on the Patents-In-Suit dated Oct. 18, 2002.

Nellcor's Third Amended Complaint for Patent Infringement. Neuman, Michael R., "Pulse Oximetry: Physical Principles, Technical

(56) References Cited

OTHER PUBLICATIONS

Realization and Present Limitations", Continuous Transcutaneous Monitoring, Plenum Press, New York, 1987, pp. 135-144.
Non-Confidential Brief of Defendants-Cross Appellants Mallinckrodt Inc. and Nellcor Puritan Bennett, Inc. dated Jan. 22, 2001.
Non-Confidential Brief of Plaintiff-Appellant Masimo Corporation dated Dec. 8, 2000.
Non-Confidential Reply Brief of Defendants-Cross Appellants Mallinckrodt Inc. and Nellcor Puritan Bennett, Inc. dated Feb. 22, 2001.
Non-Confidential Reply Brief of Plaintiff-Appellant Masimo Corporation dated Feb. 6, 2001.
Notice of Intent to Issue Ex Parte Reexamination Certificate issued in Reexamination Application No. 90/012542 on Oct. 23, 2013.
Opening Brief in Support of Defendants' Motion for Summary Judgment of Invalidity and Noninfringement of U.S. Pat. No. 5,632,272, Doc. 444, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).
Opening Brief in Support of Defendants' Motion for Summary Judgment of Invalidity of U.S. Pat. No. 6,699,194, Doc. 445, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).
Opening Brief in Support of Masimo's Motion for Reconsideration of the Court's Order and Memorandum Opinion, Doc. 790, *Masimo Corporation v. Philips Electronics North America Corporation and Philips Medizin Systeme Böblingen GMBH*, (District of Delaware, Case No. 1:09-cv-00080 (LPS/MPT) dated Apr. 15, 2014. (Redacted).
Order, Doc. 777, *Masimo Corporation v. Philips Electronics North America Corporation and Philips Medizin Systeme Böblingen GMBH*, (District of Delaware, Case No. 1:09-cv-00080 (LPS/MPT) dated Mar. 31, 2014.
Order of District Court Regarding Defendant's Motion for Summary Judgment of Non-Infringement of '642 Patent, among others, dated Oct. 4, 2000, *Masimo v. Mallicnkrodt Inc.*, cv-99-1245-AHS (C.D. Cal.).
Order Granting Plaintiff/Counter-Defendant's Motion for Judgment on the Pleadings, Doc. 117, *Masimo Corporation v. Shenzhen Mindray Bio-Medical Electronics Co., Ltd.*, Civil Action No. SACV12-02206 CJC (JPRx) dated Mar. 4, 2014.
Parties' Letter to the Court Regarding Written Description and Enablement of U.S. Pat. No. 7,215,984, Doc. 862, *Masimo Corporation v. Philips Electronics North America Corporation and Philips Medizin Systeme Böblingen GMBH*, (District of Delaware, Case No. 1:09-cv-00080 (LPS/MPT) dated Sep. 2, 2014.
Pau, L.F., "Acoustic and Vibration Monitoring," *Failure Diagnosis and Performance Monitoring*, Chapter 13, pp. 295-299.
Philip Defendant's Motion for Summary Judgment of Invalidity and Noninfringement of U.S. Pat. No. 7,215,984, Doc. 394, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Philips Electronics North America Corporation's Answer to Masimos Amended Counterclaims, *Masimo Corporation v. Philips Electronics North America Corporation and Philips Medizin Systeme Böblingen GmbH*, (District of Delaware, Case No. 09-00080(JJF)) dated May 27, 2010.
Philips' Letter to the Court, Doc. 789, *Masimo Corporation v. Philips Electronics North America Corporation and Philips Medizin Systeme Böblingen GMBH*, (District of Delaware, Case No. 1:09-cv-00080 (LPS/MPT) dated Apr. 14, 2014.
Philips' Motion for Leave to Amend Answer, Doc. 805, *Masimo Corporation v. Philips Electronics North America Corporation and Philips Medizin Systeme Böblingen GMBH*, (District of Delaware, Case No. 1:09-cv-00080 (LPS/MPT) dated May 23, 2014.
Philips North America Corporation and Philips Medizin Systeme Boblingen GmbH's Seventh Supplemental Objections and Responses to Masimo Corporation's First Set of Interrogatories (Nos. 1-8), *Masimo Corporation v. Philips Electronics North America Corporation and Philips Medizin Systeme Boblingen Gmbll*, (District of Delaware, Case No. 09-00080(JJF)) dated Jun. 30, 2010 (Redacted).
Philips' Opening Brief in Support of Defendants' Motion for Summary Judgment of Invalidity of U.S. Pat. No. 6,263,222, Doc. 413, *Masimo Corporation v. Philips Electronics North America Corporation and Philips Medizin Systeme Böblingen GMBH*, (District of Delaware, Case No. 1:09-cv-00080 (LPS/MPT) dated Aug. 14, 2012.
Philip's Opening Brief in Support of Defendant's Motion for Summary Judgment of Invalidity and Nonnigrogement of U.S. Pat. No. 7,215,984, Doc. 442, *Masimo Corporation v. Philips Electronics North America Corporation and Philips Medizin Systeme Böblingen GMBH*, (District of Delaware, Case No. 1:09-cv-00080 (LPS/MPT) dated Aug. 21, 2012. (Redacted).
Philips' Opening Brief in Support of Their Motion for Leave to Amend Its Answer, Doc. 806, *Masimo Corporation v. Philips Electronics North America Corporation and Philips Medizin Systeme Böblingen GMBH*, (District of Delaware, Case No. 1:09-cv-00080 (LPS/MPT) dated May 23, 2014. (2 Parts).
Philips' Response to Masimo Corporation's Objections to the Report and Recommendation Regarding Claim Construction, Doc. 230, *Masimo Corporation v. Philips Electronics North America Corporation and Philips Medizin Systeme Böblingen GMBH*, (District of Delaware, Case No. 1:09-cv-00080 (LPS/MPT) dated Mar. 24, 2011.
Plaintiff Masimo Corporation's Responses to Defendant Shenzhen Mindray's Second Set of Interrogatories to Plaintiff (Nos. 22-25), *Masimo Corporation v. Shenzhen Mindray Bio-Medical Electronics Co., Ltd.*, Case No. SACV12-02206 CJC (JPRx) dated Jul. 25, 2014.
"Product Information FAST-Sp02 Measurement," Agilent Technologies, printed from htt:?/www.healthcare.agilent.com/cms_update/product_information/sp02.html on Feb. 15, 2001, pp. 1-2.
Proposed Final Pretrial Order and Associated Exhibits, Doc. 834, *Masimo Corporation v. Philips Electronics North America Corporation and Philips Medizin Systeme Böblingen GMBH*, (District of Delaware, Case No. 1:09-cv-00080 (LPS/MPT) dated Aug. 18, 2014.
[Proposed] Order Granting Masimo Corporation's Motion for Judgment on the Pleadings, Doc. 107-8, *Masimo Corporation v. Shenzhen Mindray Bio-Medical Electronics Co., Ltd.*, Civil Action No. SACV12-02206 CJC (JPRx) dated Jan. 27, 2014.
Public Version of Memorandum Opinion, Doc. 781, *Masimo Corporation v. Philips Electronics North America Corporation and Philips Medizin Systeme Böblingen GMBH*, (District of Delaware, Case No. 1:09-cv-00080 (LPS/MPT) dated Apr. 7, 2014.
R. Pahl et al., "Reflectance Spectrometry in Whole Blood Using a CCD Array Camera Part I: Haematocrit Independent Measurement of Oxygen Saturation with the Aid of a New Evaluating Method," Biomed. Technik 33 (1988), pp. 240-246.
Rabiner, L.R. et al., "The Chirp z-Transform Algorithm and Its Application," Bell System Technical Journal, May-Jun. 1969, vol. 48, No. 5, pp. 1249-1292.
Rabiner, Lawrence R. et al., "Theory and Approximation of Infinite Impulse Response Digital Filters", Prentice Hall Inc., Englewood Cliffs, NJ, 1975, p. 260.
Radda, G.K. et ai, "Recent Studies on Cellular Metabolism by Nuclear Magnetic Resonance," Annual Review of Physiology, 1979, vol. 41, pp. 749-769.
Razieh Semnani et al., "Quantitative evaluation of arterial pulsatile flow and pressure, applying impedance plethysmography to a human arterial model incorporating anatomical branching and scale," Computer Methods and Programs in Biomedicine 25 (1987), pp. 13-20.
Redacted version of Plaintiff Masimo Corporation's Responses to Defendant Shenzhen Mindray's First Set of Interrogatories to Plaintiff (Nos. 1-21) *Masimo Corporation v. Shenzhen Mindray Bio-Medical Electronics Co., Ltd.*, Case No. SACV12-02206 CJC (JPRx) dated May 22, 2014.
Redacted version of Shenzhen Mindray's Objections and Responses to Masimo Corporation's Second Set of Interrogatories Nos. 6-21,

(56) References Cited

OTHER PUBLICATIONS

*Masimo Corporation v. Shenzhen Mindray Bio-Medical Electronics Co. Ltd.* Civil Action No. SACV12-02206 CJC (JPRx) dated May 22, 2014.
Reply Brief in Support of Defendants' Motion for Summary Judgment of Invalidity and Noninfringement of U.S. Pat. No. 5,632,272, Doc. 614, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012 (Redacted).
Reply Brief in Support of Defendants' Motion for Summary Judgment of Invalidity of U.S. Pat. No. 6,263,222, Doc. 613, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012 (Redacted).
Reply Brief in Support of Defendants' Motion for Summary Judgment of Invalidity of U.S. Pat. No. 6,699,194, Doc. 610, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012. (Redacted).
Reply Brief in Support of Defendants' Motion for Summary Judgment of invalidity and Noninfringement of U.S. Pat. No. 7,216,984, Doc. 609, *Masimo Corporation v. Philips Electronics North America Corporation and Philips Medizin Systeme Böblingen GMBH*, (District of Delaware, Case No. 1:09-cv-00080 (LPS/MPT) dated Oct. 26, 2012. (Redacted).
Report and Recommendation Regarding Claim Construction, Doc. 210, *Masimo Corporation v. Philips Electronics North America Corporation and Philips Medizin Systeme Böblingen GMBH*, (District of Delaware, Case No. 1:09-cv-00080 (LPS/MPT) dated Feb. 18, 2011.
Report and Recommendation Regarding Motions for Summary Judgment and Motions to Exclude, Doc. 662, *Masimo Corporation v. Philips Electronics North America Corporation and Philips Medizin Systeme Böblingen GMBH*, (District of Delaware, Case No. 1:09-cv-00080 (LPS/MPT) dated Apr. 2, 2013.
Revised Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated May 7, 2012.
Richard G. Aseltine, Jr., et al., "New Motion Resistant Sp02-Algorithm by Frequency Domain Signal Analysis," Agilent Technologies, pp. 1-10, undated.
Rusch, "Master's Thesis," Graduate School University of South Florida, Tampa, Florida (Dec. 1994).
S. Kojima et al., "Tissue Oxygen Saturation by Reflectance Spectrum Oxymetry in Myocardial Ischemia", Circulation, vol. 72, No. 4, Part II, Total pp. 3 Oct. 1985.
Sakata, M. et al., "Rapid Determination of Carboxyhemoglobin by Absorbance Difference Between Double Wavelength," The Journal of Toxicological Science, 1980, vol. 5, pp. 113-121.
Scharf, "Optimization of Portable Pulse Oximetry Through Fourier Analysis".
Scharf, "Pulse Oximetry Through Spectral Analysis".
Second Amended Complaint for Patent Infringement, Doc. 42, *Masimo Corporation v. Philips Electronics North America Corporation and Philips Medizin Systeme Böblingen GMBH*, (District of Delaware, Case No. 1:11-cv-00742 (LPS/MPT) dated Apr. 25, 2012.
Second Amended Complaint for Patent Infringement of U.S. Pat. Nos. 6,002,952; 6,263,222; 6,580,086; 6,699,194; 6,745,060; 7,215,986; 7,489,958, 7,509,154 and 8,229,533; Breach of Contract; Breach of the Covenant of Good Faith and Fair Dealing; Accounting; Tortious Interference with Prospective Economic Advantage; Declaratory Relief; and Statutory Unfair Competition, Doc. 233, *Masimo Corporation v. Shenzhen Mindray Bio-Medical Electronics Co., Ltd.*, CV SACV12-02206 CJC (JPRx) dated Jul. 7, 2014.
Second Supplemental Expert Report of Dr. Robert Stone Regarding the Invalidity of Masimo's Patents-In-Suit (U.S. Pat. No. 6,263,222 and U.S. Pat. No. 7,215,984), *Masimo Corporation v. Philips Electronics North America Corporation and Philips Medizin Systeme Böblingen GMBH*, (District of Delaware, Case No. 1:09-cv-00080 (LPS/MPT) dated Jun. 17, 2014.
Setsuo Takatani et al., "A Miniature Hybrid Reflection Type Optical Sensor for Measurement of Hemoglobin Content and Oxygen Saturation of Whole Blood," IEEE Transactions on Biomedical Engineering, vol. 35. No. 3, Mar. 1988, pp. 187-198.
Severinghaus, John W. M.D., "Pulse Oximetry Uses and Limitations", ASA Convention.
Shenzhen Mindray's Opposition to Masimo Corporation's Motion for Partial Judgment on the Pleadings, Doc. 109, *Masimo Corporation v. Shenzhen Mindray Bio-Medical Electronics Co., Ltd.*, Civil Action No. SACV12-02206 CJC (JPRx) dated Feb. 3, 2014.
Steven W. Smith, The Scientist and Engineer's Guide to Digital Signal Processing, § 8 (1st ed. 1997).
Supplemental Expert Report of Dr. Robert Stone Regarding the invalidity of Masimo's Patents-in-Suit (U.S. Pat. No. 5,632,272, U.S. Pat. No. 6,263,222, U.S. Pat. No. 7,215,984, and U.S. Pat. No. 6,699,194, *Masimo Corporation v. Philips Electronics North America Corporation and Philips Medizin Systeme Böblingen GMBH*, (District of Delaware, Case No. 1:09-cv-00080 (LPS/MPT) dated Mar. 18, 2012.
Takashi Hanioka, "Evaluation of Hemoglobin Concentration and Oxygen Saturation in Inflamed Gingiva by Tissue Reflectance Spectrophotometry," J. Osaka Univ. Dent. Soc., vol. 33, pp. 437-455, 1988.
Tremper, Kevin K. et al., "Pulse Oximetry: Technical Aspects of Machine Design" by Jonas A. Pologe, Advances in Oxygen Monitoring, Little, Brown and Company, 1987, pp. 137-153.
Trial Exhibit JTX-212, U.S. Pat. No. 6,157,850, *Mallickrodt, Inc. v Masimo Corp.*, No. cv-00-6506-MRP (C.D. Cal.).
Trial Exhibit JTX-213, File History U.S. Pat. No. 5,632,272, *Mallickrodt, Inc. v Masimo Corp.*, No. cv-00-6506-MRP (C.D. Cal.).
Trial Exhibit JTX-541, U.S. Pat. No. 4,928,692 , *Mallickrodt, Inc. v Masimo Corp.*, No. cv-00-6506-MRP (C.D. Cal.).
Trial Exhibit JTX-547, U.S. Pat. No. 5,054,495, *Mallickrodt, Inc. v Masimo Corp.*, No. cv-00-6506-MRP (C.D. Cal.).
Trial Exhibit JTX-2643, Mallinckrodt 395 Overview, *Mallickrodt, Inc. v Masimo Corp.*, No. cv-00-6506-MRP (C.D. Cal.).
Trial Exhibit JTX-4500, Slide PCSat Development, *Mallickrodt, Inc. v Masimo Corp.*, No. cv-00-6506-MRP (C.D. Cal.).
Trial Exhibit JTX-4869, Slide Robert T. Stone, Ph.D.—Educational History, *Mallickrodt, Inc. v Masimo Corp.*, No. cv-00-6506-MRP (C.D. Cal.).
Trial Exhibit JTX-4870, Slide Robert T. Stone, Ph.D.—Work Experience, *Mallickrodt, Inc. v Masimo Corp.*, No. cv-00-6506-MRP (C.D. Cal.).
Trial Exhibit JTX-4890, Slide Comparison of '850 Patent Claim 1 to the N-200, *Mallickrodt, Inc. v Masimo Corp.*, No. cv-00-6506-MRP (C.D. Cal.).
Trial Exhibit JTX-4891, Slide Comparison of '850 Patent Claim 1 to the N-200, *Mallickrodt, Inc. v Masimo Corp.*, No. cv-00-6506-MRP (C.D. Cal.).
Trial Exhibit JTX-4892, Slide Comparison of '850 Patent Claim 1 to the N-200, *Mallickrodt, Inc. v Masimo Corp.*, No. cv-00-6506-MRP (C.D. Cal.).
Trial Exhibit JTX-4893, Slide Comparison of '850 Patent Claim 1 to the N-200, *Mallickrodt, Inc. v Masimo Corp.*, No. cv-00-6506-MRP (C.D. Cal.).
Trial Exhibit JTX-4895, Slide Comparison of '850 Patent Claim 11 to the N-200, *Mallickrodt, Inc. v Masimo Corp.*, No. cv-00-6506-MPR (C.D. Cal.).
Trial Exhibit JTX-4897, Slide Comparison of '850 Patent Claim 12 to the N-200, *Mallickrodt, Inc. v Masimo Corp.*, No. cv-00-6506-MRP (C.D. Cal.).
Trial Exhibit JTX-4900, Slide Comparison of '850 Patent Claim 12 to the N-200, *Mallickrodt, Inc. v Masimo Corp.*, No. cv-00-6506-MRP (C.D. Cal.).
Trial Exhibit JTX-4902, Slide Comparison of '850 Patent Claim 22 to the N-200, *Mallickrodt, Inc. v Masimo Corp.*, No. cv-00-6506-MRP (C.D. Cal.).

(56) References Cited

OTHER PUBLICATIONS

Trial Exhibit JTX-4903, Slide Nellcor Began Using Alternative Calculations in the 1980s, *Mallickrodt, Inc.* v *Masimo Corp.*, No. cv-00-6506-MRP (C.D. Cal.).
Trial Exhibit JTX-4904, Slice Fetal Oximeter Features, *Mallickrodt, Inc.* v *Masimo Corp.*, No. cv-00-6506-MRP (C.D. Cal.).
Trial Exhibit JTX-4905, Slide Fetal Oximeter, *Mallickrodt, Inc.* v *Masimo Corp.*, No. cv-00-6506-MRP (C.D. Cal.).
Trial Exhibit JTX-4906, Slide Comparison of '850 Patent Claim 1 to the Fetal Oximeter, *Mallickrodt, Inc.* v *Masimo Corp.*, No. cv-00-6506-MRP (C.D. Cal.).
Trial Exhibit JTX-4907, Slide Comparison of '850 Patent Claim 1 to the Fetal Oximeter, *Mallickrodt, Inc.* v *Masimo Corp.*, No. cv-00-6506-MRP (C.D. Cal.).
Trial Exhibit JTX-4908, Slide Comparison of '850 Patent Claim 1 to the Fetal Oximter, *Mallickrodt, Inc.* v *Masimo Corp.*, No. cv-00-6506-MRP (C.D. Cal.).
Trial Exhibit JTX-4909, Slide Comparison of '850 Patent Claim 1 to the Fetal Oximeter, *Mallickrodt, Inc.* v *Masimo Corp.*, No. cv-00-6506-MRP (C.D. Cal.).
Trial Exhibit JTX-4910, Slide Comparison of '850 Patent Claim 10 to the Fetal Oximeter, *Mallickrodt, Inc.* v *Masimo Corp.*, No. cv-00-6506-MRP (C.D. Cal.).
Trial Exhibit JTX-4911, Slide Comparison of '850 Patent Claim 11 to the Fetal Oximeter, *Mallickrodt, Inc.* v *Masimo Corp.*, No. cv-00-6506-MRP (C.D. Cal.).
Trial Exhibit JTX-4914, Slide PCSat Features, *Mallickrodt, Inc.* v *Masimo Corp.*, No. cv-00-6506-MRP (C.D. Cal.).
Trial Exhibit JTX-4917, Slide Comparison of '850 Patent Claim 1 to the PCSat, *Mallickrodt, Inc.* v *Masimo Corp.*, No. cv-00-6506-MRP (C.D. Cal.).
Trial Exhibit JTX-4918, Slide Comparison of '850 Patent Claim 1 to PCSat, *Mallickrodt, Inc.* v *Masimo Corp.*, cv-00-6506-MRP (C.D. Cal.).
Trial Exhibit JTX-4919, Slide Comparison of '850 Patent Claim 1 to PCSat, *Mallickrodt, Inc.* v *Masimo Corp.*, cv-00-6506-MRP (C.D. Cal.).
Trial Exhibit JTX-4920, Slide Comparison of 850 Patent Claim 1 to PCSat, *Mallickrodt, Inc.* v *Masimo Corp.*, No. cv-00-6506-MRP (C.D. Cal.).
Trial Exhibit JTX-4921, Slide Comparison of '850 Patent Claim 1 to PCSat, *Mallickrodt, Inc.* v *Masimo Corp.*, No. cv-00-6506-MRP (C.D. Cal.).
Trial Exhibit JTX-4922, Slide Comparison of '850 Patent Claim to PCSAT, *Mallickrodt, Inc.* v *Masimo Corp.*, No. cv-00-6506-MPR (C.D. Cal.).
Trial Exhibit JTX-4923, Slide Comparison of '850 Patent Claim 11 to PCSat, *Mallickrodt, Inc.* v *Masimo Corp.*, No. cv-00-6506-MRP (C.D. Cal.).
Trial Exhibit JTX-4924, Slide Comparison of '850 Patent Claim 12 to PCSat, *Mallickrodt, Inc.* v *Masimo Corp.*, No. cv-00-6506-MRP (C.D. Cal.).
Trial Exhibit Jtx-4925, Slide Comparison of '850 Patent Claim 15 to PCSat, *Mallickrodt, Inc.* v *Masimo Corp.*, No. cv-00-6506-MRP (C.D. Cal.).
Trial Exhibit JTX-4926, Slide Comparison of '850 Patent Claim 22 to PCSat, *Mallickrodt, Inc.* v *Masimo Corp.*, No. cv-00-6506-MRP (C.D. Cal.).
Trial Exhibit JTX-4933, Slide Uemura Patent, *Mallickrodt, Inc.* v *Masimo Corp.*, No. cv-00-6506-MRP (C.D. Cal.).
Trial Exhibit JTX-4936, Slide Comparion of '850 Patent Claim 1 to Uemura, *Mallickrodt, Inc.* v *Masimo Corp.*, No. cv-00-6506-MRP (C.D. Cal.).
Trial Exhibit JTX-4937, Slide Comparison of '850 Patent Claim 1 to Uemura, *Mallickrodt, Inc.* v *Masimo Corp.*, No. cv-00-6506-MRP (C.D. Cal.).
Trial Exhibit JTX-4939, Slide Comparison of '850 Patent Claim 1 to Uemura, *Mallickrodt, Inc.* v *Masimo Corp.*, No. cv-00-6506-MRP (C.D. Cal.).
Trial Exhibit JTX-4942, Slide Comparison of '850 Patent Claim 1 to Uemura, *Mallickrodt, Inc.* v *Masimo Corp.*, No. cv-00-6506-MRP (C.D. Cal.).
Trial Exhibit JTX-4947, Slide '850 Patent Opinions on Description and Enablement of a Kalman Filter, *Mallickrodt, Inc.* v *Masimo Corp.*, No. cv-00-6506-MRP (C.D. Cal.).
U.S. Pat. No. 6,206,830, DX 2858, *Masimo Corporation* v. *Philips Electronics & Philips Electronics North America Corporation, et al.*, Case 1:09-cv-00080-LPS (District of Delaware).
U.S. Appl. No. 90/012,403, filed Jul. 23, 2012, requesting ex parte reexamination of U.S. Pat. No. 6,263,222, including accompanying Reexam Request, claim charts, and other documentation filed under 37 C.F.R. § 1.510 and 35 U.S.C. § 302.
U.S. Appl. No. 90/012,409, filed Aug. 17, 2012, requesting ex parte reexamination of U.S. Pat. No. 6,699,194, includin442 gaccompanying Reexam Request, claim charts, and other documentation filed under 37 C.F.R. § 1.510 and 35 U.S.C. § 302.
U.S. Appl. No. 90/012,463, filed Sep. 5, 2012, requesting ex parte reexamination of of U.S. Pat. No. 7,215,984, including accompanying Reexam Request, claim charts, and other documentation filed under 37 C.F.R. § 1.510 and 35 U.S.C. § 302.
U.S. Appl. No. 90/012,532, filed Sep. 13, 2012, requesting ex parte reexamination of U.S. Pat. No. 7,499,835, including accompanying Reexam Request, claim charts, and other documentation filed under 37 C.F.R. § 1.510 and 35 U.S.C. § 302.
U.S. Appl. No. 90/012,534, filed Sep. 13, 2012, requesting ex parte reexamination of U.S. Pat. No. 7,962,188, including accompanying Reexam Request, claim charts, and other documentation filed under 37 C.F.R. § 1.510 and 35 U.S.C. § 302.
U.S. Appl. No. 90/012,538, filed Sep. 13, 2012, requesting ex parte reexamination of U.S. Pat. No. 7,377,899, including accompanying Reexam Request, claim charts, and other documentation filed under 37 C.F.R. § 1.510 and 35 U.S.C. § 302.
U.S. Appl. No. 90/012,541, filed Sep. 13, 2012, requesting ex parte reexamination of U.S. Pat. No. 7,899,507, including accompanying Reexam Request, claim charts, and other documentation filed under 37 C.F.R. § 1.510 and 35 U.S.C. § 302.
U.S. Appl. No. 90/012,542, filed Sep. 13, 2012, requesting ex parte reexamination of U.S. Pat. No. 8,180,420, including accompanying Reexam Request, claim charts, and other documentation filed under 37 C.F.R. § 1.510 and 35 U.S.C. § 302.
U.S. Appl. No. 90/012,543, filed Sep. 13, 2012, requesting ex parte reexamination of U.S. Pat. No. 6,850,787, including accompanying Reexam Request, claim charts, and other documentation filed under 37 C.F.R. § 1.510 and 35 U.S.C. § 302.
U.S. Appl. No. 90/012,546, filed Sep. 13, 2012, requesting ex parte reexamination of U.S. Pat. No. 7,438,683, including accompanying Reexam Request, claim charts, and other documentation filed under 37 C.F.R. k 1.510 and 35 U.S.C. § 302.
U.S. Appl. No. 90/012,548, filed Sep. 13, 2012, requesting ex parte reexamination of U.S. Pat. No. 7,880,606, including accompanying Reexam Request, claim charts, and other documentation filed under 37 C.F.R. § 1.510 and 35 U.S.C. § 302.
U.S. Appl. No. 90/012,551, filed Sep. 13, 2012, requesting ex parte reexamination of U.S. Pat. No. 6,970,792, including accompanying Reexam Request, claim charts, and other documentation filed under 37 C.F.R. § 1.510 and 35 U.S.C. § 302.
U.S. Appl. No. 90/012,553, filed Sep. 13, 2012, requesting ex parte reexamination of U.S. Pat. No. 7,024,233, including accompanying Reexam Request, claim charts, and other documentation filed under 37 C.F.R. § 1.510 and 35 U.S.C. § 302.
U.S. Appl. No. 90/012,555, filed Sep. 13, 2012, requesting ex parte reexamination of U.S. Pat. No. 7,440,787, including accompanying Reexam Request, claim charts, and other documentation filed under 37 C.F.R. § 1.510 and 35 U.S.C. § 302.
U.S. Appl. No. 90/012,557, filed Sep. 13, 2012, requesting ex parte reexamination of U.S. Pat. No. 8,150,487, including accompanying Reexam Request, claim charts, and other documentation filed under 37 C.F.R. § 1.510 and 35 U.S.C. § 302.
U.S. Appl. No. 90/012,559, filed Sep. 13, 2012, requesting ex parte reexamination of U.S. Pat. No. 8,190,223, including accompanying Reexam Request, claim charts, and other documentation filed under 37 C.F.R. § 1.510 and 35 U.S.C. § 302.

(56) References Cited

OTHER PUBLICATIONS

U.S. Appl. No. 90/012,561, filed Sep. 14, 2012, requesting ex parte reexamination of U.S. Pat. No. 8,019,400, including accompanying Reexam Request, claim charts, and other documentation filed under 37 C.F.R. § 1.510 and 35 U.S.C. § 302.
U.S. Appl. No. 90/012,562, filed Sep. 14, 2012 requesting ex parte reexamination of U.S. Pat. No. 6,463,311, including accompanying Reexam Request, claim charts, and other documentation filed under 37 C.F.R. § 1.510 and 35 U.S.C. § 302.
U.S. Appl. No. 90/012,566, filed Sep. 14, 2012, requesting ex parte reexamination of U.S. Pat. No. 7,530,955, including accompanying Reexam Request, claim charts, and other documentation filed under 37 C.F.R. § 1.510 and 35 U.S.C. § 302.
U.S. Appl. No. 90/012,567, filed Sep. 14, 2012, requesting ex parte reexamination of U.S. Pat. No. 6,684,090, including accompanying Reexam Request, claim charts, and other documentation filed under 37 C.F.R. § 1.510 and 35 U.S.C. § 302.
U.S. Appl. No. 90/012,568, filed Sep. 14, 2012, requesting ex parte reexamination of U.S. Pat. No. 8,128,572, including accompanying Reexam Request, claim charts, and other documentation filed under 37 C.F.R. § 1.510 and 35 U.S.C. § 302.
U.S. Appl. No. 90/012,699, filed Oct. 4, 2012, requesting ex parte reexamination of U.S. Pat. No. 6,002,952, including accompanying Reexam Request, claim charts, and other documentation filed under 37 C.F.R. § 1.510 and 35 U.S.C. § 302.
U.S. Appl. No. 95/002,183, filed Sep. 12, 2012, requesting inter partes reexamination of U.S. Pat. No. 7,530,955, including accompanying Reexam Request, claim charts, and other documentation filed under 37 C.F.R. § 1.913 and 35 U.S.C. § 311.
United States Courts of Appeals for the Federal Circuit-Opinion, Case No. 01-1028, -1084, *Masimo v. Mallinckrodt, Inc. andNellcor Puritan Bennett, Inc.*, Decided: Aug. 8, 2001.
United States District Court—Civil Minutes, Case No. SA CV 9911245 AHS (ANX), *Masimo v. Mallinckrodt and Nellcor Puritan Bennett*, Dated Oct. 4, 2000.
V. Ya. Volkov, "Enhancing the Reliability and Accuracy of Pulse Oximetry with a Built-In Expert System," *Biomedical Engineering*, vol. 27, No. 3 (May-Jun. 1993) (translated from Russian).
V. Ya. Volkov, "Principles and Algroithms for Determining Blood Oxygenation Level by Pulse Oximetry," *Biomedical Engineering*, vol. 27, No. 1 (Jan.-Feb. 1993) (translated from Russian).
Varanini, M., et al. "*A Two Channel Adaptive Filtering Approach for Recognition of the QRS Morphology*," pp. 141-144, Proceedings of the Computers in Cardiology Meeting, Venice, Institute of Electrical and Electronics Engineers, Sep. 23-26, 1991.
Widrow, B., "*Adaptive Noise Canceling: Principles and Applications*," Proceedings of IEEE, vol. 63, No. 12, Dec. 1975.
Widrow, Bernard, Adaptive Signal Processing, Prentice Hall, Englewood Cliffs, NJ, 1985.
Widrow, Bernard, Adaptive Signal Processing, Prentice Hall, Englewood Cliffs, NJ, Chapter 1 "Adaptive Systems", pp. 3-13, 1985.
Widrow, Bernard, et al., Chapter 12: "The Adaptive Interference Canceling" Adaptive Signal Processing, Prentice-Hall, Inc., pp. 302-367,1985.
Widrow, Bernard, et al., Chapter 2: "The Adaptive Linear Combiner", Adaptive Signal Processing, Prentice-Hall, Inc., pp. 15-26, 1985.
Wukitsch, et al., "Knowing Your Monitoring Equipment," Journal of Clinical Monitoring, vol. 4, No. 4 (Oct. 1998).
Y. Shimada et al., "Effects of multiple scattering and peripheral circulation on arterial oxygen saturation measured with a pulse-type oximeter," Medical & Biological Engineering & Computing, Sep. 1984, pp. 475-478.
Yeldennan, M., et al., *Ecg Enhancement by Adaptive Cancellation of Electrosurgical Interference*. pp. 1-21.
Yeldennan, M., et al., *Sodium Nitroprusside Infusion by Adaptive Control*. Adaptive Control by Inverse Modeling, Conference Record: 12th Asilosor Conference 90 (1978).
Yu, c., et al., "Improvement in Arterial Oxygen Control Using Multiple Model Adaptive Control Procedures," pp. 878-883.

Exhibit B, Preliminary Invalidity Contentions, Apr. 17, 2015, *Masimo Corporation v. Philips Electronics & Philips Electronics North America Corporation, et al.*, Case 1:09-cv-00080-LPS (District of Delaware).
510(k) Notification Siemens KION, K973971, Sep. 13, 1999.
Schaffartzik, *KION Ein neues Anasthesie-System*, Der Aanesthesist, Nov. 1997.
KION/KION-i Anesthesia Workstation: Service Manual.
SC 7000 and SC 9000XL Patient Monitors: Service Manual, Apr. 1997.
Pulse Oximeters—Premarket Notification Submissions [510(k)s]: Guidance for Industry and Food and Drug Administration Staff, U.S. Dep't of Health and Human Services, Food and Drug Administration, Mar. 4, 2013.
ISO 80601-2-61: Medical Electrical Equipment, Particular Requirements for Basic Safety and Essential Performance of Pulse Oximeter Equipment, Apr. 1, 2011.
Pan, et al., *A Real-Time QRS Detection Algorithm*, IEEE Transactions on Biomedical Engineering, vol. BME-32, No. 3, Mar. 1985.
May 18, 2015 [998] Order Denying [926] Philips' Renewed Motion for Judgment, *Masimo Corporation v. Philips Electronics North America Corporation & Philips Medizin Systeme Böblingen GmbH*, Case 1:09-cv-00080-LPS (District of Delaware).
May 18, 2015 [997] Memorandum Opinion Regarding [926] Philips' Motion for a New Trial, *Masimo Corporation v. Philips Electronics North America Corporation & Philips Medizin Systeme Böblingen GmbH* Case 1:09-cv-00080-LPS (District of Delaware).
May 18, 2015 [996] Order Denying [972] Masimo's Motion for Judgment, *Masimo Corporation v. Philips Electronics North America Corporation & Philips Medizin Systeme Böblingen GmbH* Case 1:09-cv-00080-LPS (District of Delaware).
May 18, 2015 [995] Memorandum Opinion Regarding Patent Misuse, *Masimo Corporation v. Philips Electronics North America Corporation & Philips Medizin Systeme Böblingen GmbH* Case 1:09-cv-00080-LPS (District of Delaware).
May 18, 2015 [994] Order Regarding [993] Memorandum Opinion Regarding Inequitable Conduct, *Masimo Corporation v. Philips Electronics North America Corporation & Philips Medizin Systeme Böblingen GmbH* Case 1:09-cv-00080-LPS (District of Delaware).
May 18, 2015 [993] Memorandum Opinion Regarding Inequitable Conduct, *Masimo Corporation v. Philips Electronics North America Corporation & Philips Medizin Systeme Böblingen GmbH* Case 1:09-cv-00080-LPS (District of Delaware).
May 22, 2015 Expert Report of Mr. James E. Corenman Regarding the Invalidity of the '952, '222, '086, '194, '060, '986, '958, '154, and '533 Patents, *Masimo Corporation v. Shenzhen Mindray Bio-Medical Electronics Co., Ltd.*, Case 8:12-cv-02206-CJC-JPR (District of California).
May 22, 2015 Expert Report of Michael Sofocleous, *Masimo Corporation, et al. v. Shenzhen Mindray Bio-Medical Electronics Co., Ltd.*, Case 8:12-cv-02206-CJC-JPR (District of California).
May 22, 2015 Expert Report of Mr. Thomas Scharf Regarding Invalidity of U.S. Pat. No. 6,263,222, *Masimo Corporation, et al. v. Shenzhen Mindray Bio-Medical Electronics Co., Ltd.*, Case 8:12-cv-02206-CJC-JPR (District of California).
May 22, 2015 Expert Report of Dr. Robert T. Stone, *Masimo Corporation, et al. v. Shenzhen Mindray Bio-Medical Electronics Co., Ltd.*, Case 8:12-cv-02206-CJC-JPR (District of California).
Shenzhen Mindray's Objections and Responses to Masimo Corporation's Seventh Set of Interrogatories (No. 35), *Masimo Corp. v. Shenzhen Mindray Bio-Medical Elecs. Co., Ltd.*, Case No. 8:12-cv-02206-CJC-JPR (C.D. Cal. filed Dec. 21, 2012).
Redacted Shenzhen Mindray's Fourth Supplemental Objections and Responses to Masimo Corporation's Second Set of Interrogatories Nos. 6-21, *Masimo Corp. v. Shenzhen Mindray Bio-Medical Elecs. Co., Ltd.*, Case No. 8:12-cv-02206-CJC-JPR C.D. Cal. filed Dec. 21, 2012).
Scharf, J.E., "Optimization of Portable Pulse Oximetry through Fourier Analysis", Proceedings of the Twelfth Southern Biomedical Engineering Conference, pp. 233-235, Apr. 1993.
Scharf, J.E., "Pulse Oximetry through Spectral Analysis", Proceedings of the Twelfth Southern Biomedical Engineering Conference, pp. 227-229, Apr. 1993.

(56) References Cited

OTHER PUBLICATIONS

Video Demonstration of Pulse Oximetry and the Fast Fourier Transform, Thomas Scharf.
Video Demonstration of Efficacy of the Frequency Domain Algorithm with Regard to Rejection of Motion Artifact, Dr. Robert T. Stone.
Apr. 9, 2015 [419] Masimo's Supplemental Memorandum in Opposition to Mindray's Motion to Compel Production, *Masimo Corporation, et al. v. Shenzhen Mindray Bio-Medical Electronics Co., Ltd.*, Case SACV12-02206 CJC (DFMx) (District of California).
Apr. 17, 2015 [441] Minute Order Granting Plaintiff's motion to compel [339] and Denying Def Motion to Compel [398], *Masimo Corporation, et al. v. Shenzhen Mindray Bio-Medical Electronics Co., Ltd.*, Case SACV12-02206 CJC (DFMx) (District of California).
Apr. 22, 2015 [452] Minute Order Granting [392] Masimo's Motion to Compel Interrogatory Responses, *Masimo Corporation, et al. v. Shenzhen Mindray Bio-Medical Electronics Co., Ltd.*, Case SACV12-02206 CJC (DFMx) (District of California).
May 7, 2015 [526] Mindray's Notice of Motion and Motion for Review of [441] Magistrate Judge's Apr. 17, 2015 Order, *Masimo Corporation, et al. v. Shenzhen Mindray Bio-Medical Electronics Co., Ltd.*, Case SACV12-02206 CJC (DFMx) (District of California).
May 7, 2015 [526-1] Memorandum in Support of Mindray's Motion for Review of [441] Magistrate Judge's Apr. 17, 2015 Order [Public], *Masimo Corporation, et al. v. Shenzhen Mindray Bio-Medical Electronics Co., Ltd.*, Case SACV12-02206 CJC (DFMx) (District of California).
May 7, 2015 [526-2] Declaration of Jose Patino in Support of Mindray's Motion for Review of [441] Magistrate Judge's Apr. 17, 2015 Order, *Masimo Corporation, et al. v. Shenzhen Mindray Bio-Medical Electronics Co., Ltd.*, Case SACV12-02206 CJC (DFMx) (District of California).
May 11, 2015[530] Mindray's Notice of Motion and Motion for Review of [452] Magistrate's Order, *Masimo Corporation, et al. v. Shenzhen Mindray Bio-Medical Electronics Co., Ltd.*, Case SACV12-02206 CJC (DFMx) (District of California).
May 11, 2015[530-1] Memorandum in Support of Mindray's Motion for Review of [452] Magistrate's Order, *Masimo Corporation, et al. v. Shenzhen Mindray Bio-Medical Electronics Co., Ltd.*, Case SACV12-02206 CJC (DFMx) (District of California).
May 11, 2015[530-2] Proposed Order Granting Mindray's Motion for Review of [452] Magistrate's Order, *Masimo Corporation, et al. v. Shenzhen Mindray Bio-Medical Electronics Co., Ltd.*, Case SACV12-02206 CJC (DFMx) (District of California).
May 18, 2015 [542] Masimo's Opposition to Mindray's Motion for Review of [441] Magistrate Judge's Apr. 17, 2015 Order, *Masimo Corporation, et al. v. Shenzhen Mindray Bio-Medical Electronics Co., Ltd.*, Case SACV12-02206 CJC (DFMx) (District of California).
May 18, 2015 [543] Masimo's Opposition to Mindray's Motion for Review of [452] Magistrate's Order, *Masimo Corporation, et al. v. Shenzhen Mindray Bio-Medical Electronics Co., Ltd.*, Case SACV12-02206 CJC (DFMx) (District of California).
May 22, 2015 [548] Mindray's Reply to Motion for Review of [441] Order, *Masimo Corporation, et al. v. Shenzhen Mindray Bio-Medical Electronics Co., Ltd.*, Case SACV12-02206 CJC (DFMx) (District of California).
May 22, 2015 [548-1] Declaration of Justin Gray in Support of Mindray's Reply to Motion for Review of [441] Order, *Masimo Corporation, et al. v. Shenzhen Mindray Bio-Medical Electronics Co., Ltd.*, Case SACV12-02206 CJC (DFMx) (District of California).
May 22, 2015 [549] Declaration of Christopher Bolten in Support of Mindray's Reply to Motion for Review of [441] Order, *Masimo Corporation, et al. v. Shenzhen Mindray Bio-Medical Electronics Co., Ltd.*, Case SACV12-02206 CJC (DFMx) (District of California).
May 22, 2015 [550] Mindray's Reply to Motion for Review of [452] Order, *Masimo Corporation, et al. v. Shenzhen Mindray Bio-Medical Electronics Co., Ltd.*, Case SACV12-02206 CJC (DFMx) (District of California).
May 27, 2015 [552] Corrected Declaration of Justin Gray in Support of Mindray's Motion for Review of [441] Magistrate Judge's Apr. 17, 2015 Order, *Masimo Corporation, et al. v. Shenzhen Mindray Bio-Medical Electronics Co., Ltd.*, Case SACV12-02206 CJC (DFMx) (District of California).
May 27, 2015 [552-2] Corrected Declaration of Christopher Bolten in Support of Mindray's Motion for Review of [441] Magistrate Judge's Apr. 17, 2015 Order, *Masimo Corporation, et al. v. Shenzhen Mindray Bio-Medical Electronics Co., Ltd.*, Case SACV12-02206 CJC (DFMx) (District of California).
Jun. 3, 2015 [554] Minute Order Denying [526] [530] Mindray's Motions for Review, *Masimo Corporation, et al. v. Shenzhen Mindray Bio-Medical Electronics Co., Ltd.*, Case SACV12-02206 CJC (DFMx) (District of California).
Jun. 15, 2015 [562] Stipulated Dismissal of Certain Claims and Counterclaims, *Masimo Corporation, et al. v. Shenzhen Mindray Bio-Medical Electronics Co., Ltd.*, Case SACV12-02206 CJC (DFMx) (District of California).
Jun. 15, 2015 [562-1] [Proposed] Order on Stipulated Dismissal of Certain Claims and Counterclaims, *Masimo Corporation, et al. v. Shenzhen Mindray Bio-Medical Electronics Co., Ltd.*, Case SACV12-02206 CJC (DFMx) (District of California).
Jun. 16, 2015 [564] Order on Stipulated Dismissal of Certain Claims and Counterclaims, *Masimo Corporation, et al. v. Shenzhen Mindray Bio-Medical Electronics Co., Ltd.*, Case SACV12-02206 CJC (DFMx) (District of California).
Jun. 22, 2015 [566] Mindray's Notice of Motion and Motion for Reconsideration of [554] Court Order, *Masimo Corporation, et al. v. Shenzhen Mindray Bio-Medical Electronics Co., Ltd.*, Case SACV12-02206 CJC (DFMx) (District of California).
Jun. 22, 2015 [566-1] Memorandum in Support of Mindray's Motion for Reconsideration of [554] Court Order, *Masimo Corporation, et al. v. Shenzhen Mindray Bio-Medical Electronics Co., Ltd.*, Case SACV12-02206 CJC (DFMx) (District of California).
Jun. 22, 2015 [566-2] Declaration of Justin Gray in Support of Mindray's Motion for Reconsideration of [554] Court Order, *Masimo Corporation, et al. v. Shenzhen Mindray Bio-Medical Electronics Co., Ltd.*, Case SACV12-02206 CJC (DFMx) (District of California).
Jun. 22, 2015 [566-3] [Proposed] Order Granting Mindray's Motion for Reconsideration of [554] Court Order, *Masimo Corporation, et al. v. Shenzhen Mindray Bio-Medical Electronics Co., Ltd.*, Case SACV12-02206 CJC (DFMx) (District of California).
Jun. 29, 2015 [570] Masimo's Opposition to Mindray's Motion for Reconsideration of [554] Court Order, *Masimo Corporation, et al. v. Shenzhen Mindray Bio-Medical Electronics Co., Ltd.*, Case SACV12-02206 CJC (DFMx) (District of California).
Jul. 6, 2015 [573] Reply in Support of Mindray's Motion for Reconsideration of [554] Court Order, *Masimo Corporation, et al. v. Shenzhen Mindray Bio-Medical Electronics Co., Ltd.*, Case SACV12-02206 CJC (DFMx) (District of California).
Jul. 16, 2015 [574] Minute Order Denying Defendant's Motion for Reconsideration [566], *Masimo Corporation, et al. v. Shenzhen Mindray Bio-Medical Electronics Co., Ltd.*, Case SACV12-02206 CJC (DFMx) (District of California).
Mar. 31, 2015[392] Joint Stipulation Accompanying Masimo's Motion to Compel Interrogatory Responses, *Masimo Corporation, et al. v. Shenzhen Mindray Bio-Medical Electronics Co., Ltd.*, Case SACV12-02206 CJC (JPRx) (District of California).
Mar. 31, 2015[392-2] Declaration of Mark Kachner in Support of Joint Stipulation Accompanying Masimo's Motion to Compel Interrogatory Responses, *Masimo Corporation, et al. v. Shenzhen Mindray Bio-Medical Electronics Co., Ltd.*, Case SACV12-02206 CJC (JPRx) (District of California).
Mar. 31, 2015[392-6] Declaration of Justin Gray in Opposition to Masimo's Motion to Compel Interrogatory Responses, *Masimo Corporation, et al. v. Shenzhen Mindray Bio-Medical Electronics Co., Ltd.*, Case SACV12-02206 CJC (DFMx) (District of California).
Mar. 31, 2015[392-7] [Proposed] Order Granting Masimo's Motion to Compel Interrogatory Responses, *Masimo Corporation, et al. v. Shenzhen Mindray Bio-Medical Electronics Co., Ltd.*, Case SACV12-02206 CJC (DFMx) (District of California).
Apr. 2, 2015 [398] Shenzhen Mindray's Notice of Motion and Motion to Compel Production of Documents, *Masimo Corporation,*

(56) References Cited

OTHER PUBLICATIONS

*et al.* v. *Shenzhen Mindray Bio-Medical Electronics Co., Ltd.*, Case SACV12-02206 CJC (DFMx) (District of California).
Apr. 2, 2015 [398-1] Joint Stipulation Accompanying Shenzhen Mindray's Notice of Motion and Motion to Compel Production of Documents [Redacted] , *Masimo Corporation, et al.* v. *Shenzhen Mindray Bio-Medical Electronics Co., Ltd.*, Case SACV12-02206 CJC (DFMx) (District of California).
Apr. 2, 2015 [398-2] Declaration of Justin Gray in Support of Shenzhen Mindray's Motion to Compel Production of Documents, *Masimo Corporation, et al.* v. *Shenzhen Mindray Bio-Medical Electronics Co., Ltd.*, Case SACV12-02206 CJC (DFMx) (District of California).
Apr. 2, 2015 [398-6] [Proposed] Order Granting Shenzhen Mindray's Motion to Compel Production of Documents, *Masimo Corporation, et al.* v. *Shenzhen Mindray Bio-Medical Electronics Co., Ltd.*, Case SACV12-02206 CJC (DFMx) (District of California).
Apr. 7, 2015 [410] Masimo's Supplemental Memorandum in Support of Motion to Compel Interrogatory Responses, *Masimo Corporation, et al.* v. *Shenzhen Mindray Bio-Medical Electronics Co., Ltd.*, Case SACV12-02206 CJC (DFMx) (District of California).
Apr. 7, 2015 [411] Mindray's Supplemental Opposition to Masimo's Motion to Compel Interrogatory Responses, *Masimo Corporation, et al.* v. *Shenzhen Mindray Bio-Medical Electronics Co., Ltd.*, Case SACV12-02206 CJC (DFMx) (District of California).
Masimo Corporation And Masimo International Sarl's Notice Of Motion And Motion For Summary Judgment Of No Prosecution Laches, D.I. 577, Aug. 10, 2015, *Masimo Corporation* v. *Shenzhen Mindray Bio-Medical Electronics Co., Ltd.*, Case No. SACV12-02206 CJC (DFMx).
[Proposed] Order Granting Masimo Corporation And Masimo International Sarl's Motion For Summary Judgment Of No Inequitable Conduct, D.I. 584-1, Aug. 10, 2015, *Masimo Corporation* v. *Shenzhen Mindray Bio-Medical Electronics Co., Ltd.*, Case No. SACV12-02206 CJC (DFMx).
[Proposed] Statement Of Uncontroverted Facts And Conclusions Of Law In Support Of Masimo's Motion For Summary Judgment Of No Prosecution Laches, D.I. 577-2, Aug. 10, 2015, *Masimo Corporation* v. *Shenzhen Mindray Bio-Medical Electronics Co., Ltd.*, Case No. SACV12-02206 CJC (DFMx).
Memorandum In Support Of Masimo Corporation And Masimo International Sarl's Motion For Summary Judgment Of No Prosecution Laches, D.I. 578, Aug. 10, 2015, *Masimo Corporation* v. *Shenzhen Mindray Bio-Medical Electronics Co., Ltd.*, Case No. SACV12-02206 CJC (DFMx).
Masimo Corporation And Masimo International Sarl's Notice Of Motion And Motion For Summary Judgment Of No Inequitable Conduct, D.I. 584, Aug. 10, 2015, *Masimo Corporation* v. *Shenzhen Mindray Bio-Medical Electronics Co., Ltd.*, Case No. SACV12-02206 CJC (DFMx).
[Proposed] Order Granting Masimo Corporation And Masimo International Sarl's Motion For Summary Judgment Of No Inequitable Conduct, D.I. 577-1, Aug. 10, 2015, *Masimo Corporation* v. *Shenzhen Mindray Bio-Medical Electronics Co., Ltd.*, Case No. SACV12-02206 CJC (DFMx).
[Proposed] Statement Of Uncontroverted Facts And Conclusion Of Law In Support Of Masimo's Motion For Summary Judgment Of No Inequitable Conduct, D.I. 584-2, Aug. 10, 2015, *Masimo Corporation* v. *Shenzhen Mindray Bio-Medical Electronics Co., Ltd.*, Case No. SACV12-02206 CJC (DFMx).
Memorandum In Support Of Masimo Corporation And Masimo International Sarl's Motion For Summary Judgment Of No Inequitable Conduct, D.I. 585, Aug. 10, 2015, *Masimo Corporation* v. *Shenzhen Mindray Bio-Medical Electronics Co., Ltd.*, Case No. SACV12-02206 CJC (DFMx).
Shenzhen Mindray Biomedical Electronics Co., Ltd.'S Notice Of Motion And Motion For Summary Judgment Of Invalidity Of U.S. Pat. No. 7,489,958, D.I. 590, Aug. 10, 2015, *Masimo Corporation* v. *Shenzhen Mindray Bio-Medical Electronics Co., Ltd.*, Case No. SACV12-02206 CJC (DFMx).
Memorandum Of Points And Authorities In Support Of Shenzhen Mindray Biomedical Electronics Co., Ltd.'s Motion For Summary Judgment Of Invalidity Of U.S. Pat. No. 7,489,958, D.I. 590-1, Aug. 10, 2015, *Masimo Corporation* v. *Shenzhen Mindray Bio-Medical Electronics Co., Ltd.*, Case No. SACV12-02206 CJC (DFMx).
Statement Of Uncontroverted Facts And Conclusions Of Law In Support Of Shenzhen Mindray Bio-Medical Electronics Co., Ltd.'s Motion For Summary Judgment Of Invalidity Of U.S. Pat. No. 7,489,958, D.I. 590-2, Aug. 10, 2015, *Masimo Corporation* v. *Shenzhen Mindray Bio-Medical Electronics Co., Ltd.*, Case No. SACV12-02206 CJC (DFMx).
Declaration Of Nicola A. Pisano In Support Of Shenzhen Mindray Bio-Medical Electronics Co., Ltd.'s Motion For Summary Judgment Of Invalidity Of U.S. Pat. No. 7,489,958, D.I. 590-3, Aug. 10, 2015, *Masimo Corporation* v. *Shenzhen Mindray Bio-Medical Electronics Co., Ltd.*, Case No. SACV12-02206 CJC (DFMx).
[Proposed] Order Granting Shenzhen Mindray Biomedical Electronics Co., Ltd.'s Motion For Summary Judgment Of Invalidity Of U.S. Pat. No. 7,489,958, D.I. 590-10, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 1, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 2, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 3, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 4, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 5, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 6, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 7, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 8, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 9, Aug. 10, 2015,

(56) References Cited

OTHER PUBLICATIONS

*Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 10, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 11, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part, 12, Aug. 10, 2015, *Masimo Corporation* v. *Shenzhen Mindray Bio-Medical Electronics Co., Ltd.*, Case No. SACV12-02206 CJC (DFMx).
Declaration Of Nicholas A. Belair In Support Of Masimo Corporation And Masimo International Sarl's Motion For Summary Judgment Of No Inequitable Conduct And Motion For Summary Judgment Of No Prosecution Laches, D.I. 591, Part 13, Aug. 10, 2015, *Masimo Corporation* v. *Shenzhen Mindray Bio-Medical Electronics Co., Ltd.*, Case No. SACV12-02206 CJC (DFMx).
Shenzhen Mindray Biomedical Electronics Co., Ltd.'s Notice Of Motion And Motion To Exclude The Expert Testimony Of Dr. Nitin Shah, D.I. 600, Aug. 10, 2015, *Masimo Corporation* v. *Shenzhen Mindray Bio-Medical Electronics Co., Ltd.*, Case No. SACV12-02206 CJC (DFMx).
Memorandum Of Points And Authorities In Support Of Shenzhen Mindray Biomedical Electronics Co., Ltd.'S Motion To Exclude The Expert Testimony Of Dr. Nitin Shah, D.I. 600-1, Aug. 10, 2015, *Masimo Corporation* v. *Shenzhen Mindray Bio-Medical Electronics Co., Ltd.*, Case No. SACV12-02206 CJC (DFMx).
Declaration Of Justin E. Gray In Support Of Shenzhen Mindray Bio-Medical Electronics Co., Ltd.'s Motion To Exclude The Expert Testimony Of Dr. Nitin Shah, D.I. 600-2, Part 1, Aug. 10, 2015, *Masimo Corporation* v. *Shenzhen Mindray Bio-Medical Electronics Co., Ltd.*, Case No. SACV12-02206 CJC (DFMx).
Declaration Of Justin E. Gray In Support Of Shenzhen Mindray Bio-Medical Electronics Co., Ltd.'s Motion To Exclude The Expert Testimony Of Dr. Nitin Shah, D.I. 600-2, Part 2, Aug. 10, 2015, *Masimo Corporation* v. *Shenzhen Mindray Bio-Medical Electronics Co., Ltd.*, Case No., SACV12-02206 CJC (DFMx).
Declaration Of Justin E. Gray In Support Of Shenzhen Mindray Bio-Medical Electronics Co., Ltd.'s Motion To Exclude The Expert Testimony Of Dr. Nitin Shah, D.I. 600-2, Part 3, Aug. 10, 2015, *Masimo Corporation* v. *Shenzhen Mindray Bio-Medical Electronics Co., Ltd.*, Case No. SACV12-02206 CJC (DFMx).
Declaration Of Justin E. Gray In Support Of Shenzhen Mindray Bio-Medical Electronics Co., Ltd.'s Motion To Exclude The Expert Testimony Of Dr. Nitin Shah, D.I. 600-2, Part 4, Aug. 10, 2015, *Masimo Corporation* v. *Shenzhen Mindray Bio-Medical Electronics Co., Ltd.*, Case No. SACV12-02206 CJC (DFMx).
[Proposed] Order Granting Shenzhen Mindray Biomedical Electronics Co., Ltd.'s Motion To Exclude The Expert Testimony Of Dr. Nitin Shah, D.I. 600-9, Aug. 10, 2015, *Masimo Corporation* v. *Shenzhen Mindray Bio-Medical Electronics Co., Ltd.*, Case No. SACV12-02206 CJC (DFMx).
Shenzhen Mindray Biomedical Electronics Co., Ltd.'S Notice Of Motion And Motion To Exclude The Expert Testimony Of Mohamed Diab And Any Reliance On His Expert Opinions, D.I. 617, Aug. 10, 2015, *Masimo Corporation* v. *Shenzhen Mindray Bio-Medical Electronics Co., Ltd.*, Case No. SACV12-02206 CJC (DFMx).
Memorandum Of Points And Authorities In Support Of Shenzhen Mindray Bio-Medical Electronics Co., Ltd.'s Motion To Exclude The Expert Testimony Of Mohamed Diab And Any Reliance On His Expert Opinions, D.I. 617-1, Aug. 10, 2015, *Masimo Corporation* v. *Shenzhen Mindray Bio-Medical Electronics Co., Ltd.*, Case No. SACV12-02206 CJC (DFMx).
Declaration Of Nicola A. Pisano In Support Of Shenzhen Mindray Bio-Medical Electronics Co., Ltd.'s Motion To Exclude The Expert Testimony Of Mohamed Diab And Any Reliance On His Expert Opinions, D.I. 617-2, Part 1, Aug. 10, 2015, *Masimo Corporation* v. *Shenzhen Mindray Bio-Medical Electronics Co., Ltd.*, Case No. SACV12-02206 CJC (DFMx).
Declaration Of Nicola A. Pisano In Support Of Shenzhen Mindray Bio-Medical Electronics Co., Ltd.'s Motion To Exclude The Expert Testimony Of Mohamed Diab And Any Reliance On His Expert Opinions, D.I. 617-2, Part 2, Aug. 10, 2015, *Masimo Corporation* v. *Shenzhen Mindray Bio-Medical Electronics Co., Ltd.*, Case No. SACV12-02206 CJC (DFMx).
Declaration Of Nicola A. Pisano In Support Of Shenzhen Mindray Bio-Medical Electronics Co., Ltd.'s Motion To Exclude The Expert Testimony Of Mohamed Diab And Any Reliance On His Expert Opinions, D.I. 617-2, Part 3, Aug. 10, 2015, *Masimo Corporation* v. *Shenzhen Mindray Bio-Medical Electronics Co., Ltd.*, Case No. SACV12-02206 CJC (DFMx).
Declaration Of Nicola A. Pisano In Support Of Shenzhen Mindray Bio-Medical Electronics Co., Ltd.'s Motion To Exclude The Expert Testimony Of Mohamed Diab And Any Reliance On His Expert Opinions, D.I. 617-2, Part 4, Aug. 10, 2015, *Masimo Corporation* v. *Shenzhen Mindray Bio-Medical Electronics Co., Ltd.*, Case No. SACV12-02206 CJC (DFMx).
Declaration Of Nicola A. Pisano In Support Of Shenzhen Mindray Bio-Medical Electronics Co., Ltd.'s Motion To Exclude The Expert Testimony Of Mohamed Diab And Any Reliance On His Expert Opinions, D.I. 617-2, Part 5, Aug. 10, 2015, *Masimo Corporation* v. *Shenzhen Mindray Bio-Medical Electronics Co., Ltd.*, Case No. SACV12-02206 CJC (DFMx).
Declaration Of Nicola A. Pisano In Support Of Shenzhen Mindray Bio-Medical Electronics Co., Ltd.'s Motion To Exclude The Expert Testimony Of Mohamed Diab And Any Reliance On His Expert Opinions, D.I. 617-2, Part 6, Aug. 10, 2015, *Masimo Corporation* v. *Shenzhen Mindray Bio-Medical Electronics Co., Ltd.*, Case No. SACV12-02206 CJC (DFMx).
[Proposed] Order Granting Shenzhen Mindray Biomedical Electronics Co., Ltd.'s Motion To Exclude The Expert Testimony Of Mohamed Diab And Any Reliance On His Expert Opinions, D.I. 617-34, Aug. 10, 2015, *Masimo Corporation* v. *Shenzhen Mindray Bio-Medical Electronics Co., Ltd.*, Case SACV12-02206 CJC (DFMx).
Shenzhen Mindray Biomedical Electronics Co., Ltd.'S Notice Of Motion And Motion To Exclude The Expert Testimony Of Richard Meyst, D.I. 620, Aug. 10, 2015, *Masimo Corporation* v. *Shenzhen Mindray Bio-Medical Electronics Co., Ltd.*, Case No. SACV12-02206 CJC (DFMx).
Memorandum Of Points & Authorities In Support Of Shenzhen Mindray Biomedical Electronics Co., Ltd.'s Motion To Exclude The Expert Testimony Of Richard Meyst, D.I. 620-1, Aug. 10, 2015, *Masimo Corporation* v. *Shenzhen Mindray Bio-Medical Electronics Co., Ltd.*, Case No. SACV12-02206 CJC (DFMx).
Shenzhen Mindray Biomedical Electronics Co., Ltd.'s Declaration Of Scott A. Penner In Support Of Motion To Exclude The Expert Testimony Of Richard Meyst, D.I. 620-2, Aug. 10, 2015, *Masimo Corporation* v. *Shenzhen Mindray Bio-Medical Electronics Co., Ltd.*, Case No. SACV12-02206 CJC (DFMx).
[Proposed] Order Granting Shenzhen Mindray Biomedical Electronics Co., Ltd.'s Motion To Exclude The Expert Testimony Of Richard Meyst, D.I. 620-9, Aug. 10, 2015, *Masimo Corporation* v. *Shenzhen Mindray Bio-Medical Electronics Co., Ltd.*, Case No. SACV12-02206 CJC (DFMx).
Shenzhen Mindray Biomedical Electronics Co., Ltd.'s Notice Of Motion And Motion For Partial Summary Judgment Of No Direct Infringement, No Pre-Suit Indirect Infringement, And No Willful Infringement, D.I. 623, Aug. 10, 2015, *Masimo Corporation* v. *Shenzhen Mindray Bio-Medical Electronics Co., Ltd.*, Case No. SACV12-02206 CJC (DFMx).
Memorandum Of Points And Authorities In Support Of Shenzhen Mindray Biomedical Electronics Co., Ltd.'s Motion For Partial Sum-

(56) References Cited

OTHER PUBLICATIONS mary Judgment Of No Direct Infringement, No Presuit Indirect Infringement, And No Willful Infringement, D.I. 623-1, Aug. 10, 2015, *Masimo Corporation v. Shenzhen Mindray Bio-Medical Electronics Co., Ltd.*, Case No. SACV12-02206 CJC (DFMx).
Statement Of Uncontroverted Facts And Conclusions Of Law In Support Of Shenzhen Mindray Bio-Medical Electronics Co., Ltd.'s Motion For Partial Summary Judgment Of No Direct Infringement, No Presuit Indirect Infringement, And No Willful Infringement, D.I. 623-2, Aug. 10, 2015, *Masimo Corporation v. Shenzhen Mindray Bio-Medical Electronics Co., Ltd.*, Case No. SACV12-02206 CJC (DFMx).
Declaration of Justin E. Gray In Support Of Shenzhen Mindray Bio-Medical Electronics Co., Ltd.'s Motion For Partial Summary Judgment Of No Direct Infringement, No Pre-Suit Indirect Infringement, And No Willful Infringement, D.I. 623-3, Part 1, Aug. 10, 2015, *Masimo Corporation v. Shenzhen Mindray Bio-Medical Electronics Co., Ltd.*, Case No. SACV12-02206 CJC (DFMx).
Declaration Of Justin E. Gray In Support Of Shenzhen Mindray Bio-Medical Electronics Co., Ltd.'s Motion For Partial Summary Judgment Of No Direct Infringement, No Pre-Suit Indirect Infringement, And No Willful Infringement, D.I. 623-3, Part 2, Aug. 10, 2015, *Masimo Corporation v. Shenzhen Mindray Bio-Medical Electronics Co., Ltd.*, Case No. SACV12-02206 CJC (DFMx).
Declaration Of Justin E. Gray In Support Of Shenzhen Mindray Bio-Medical Electronics Co., Ltd.'s Motion For Partial Summary Judgment Of No Direct Infringement, No Pre-Suit Indirect Infringement, And No Willful Infringement, D.I. 623-3, Part 3, Aug. 10, 2015, *Masimo Corporation v. Shenzhen Mindray Bio-Medical Electronics Co., Ltd.*, Case No. SACV12-02206 CJC (DFMx).
[Proposed] Order Granting Shenzhen Mindray Bio-Medical Electronics Co., Ltd.'s Motion For Partial Summary Judgment Of No Direct Infringement, No Pre-Suit Indirect Infringement, And No Willful Infringement, D.I. 623-14, Aug. 10, 2015, *Masimo Corporation v. Shenzhen Mindray Bio-Medical Electronics Co., Ltd.*, Case No. SACV12-02206 CJC (DFMx).
Shenzhen Mindray Biomedical Electronics Co., Ltd.'s Notice Of Motion And Motion To Exclude The Expert Testimony Of Vijay Madisetti, D.I. 627, Aug. 10, 2015, *Masimo Corporation v. Shenzhen Mindray Bio-Medical Electronics Co., Ltd.*, Case No. SACV12-02206 CJC (DFMx).
Shenzhen Mindray Biomedical Electronics Co., Ltd.'s Memorandum Of Points And Authorities In Support Of Its Motion To Exclude The Expert Testimony Of Vijay Madisetti, D.I. 627-1, Aug. 10, 2015, *Masimo Corporation v. Shenzhen Mindray Bio-Medical Electronics Co., Ltd.*, Case No. SACV12-02206 CJC (DFMx).
Shenzhen Mindray Biomedical Electronics Co., Ltd.'s Declaration Of Scott A. Penner In Support Of Motion To Exclude The Expert Testimony Of Vijay Madisetti, D.I. 627-2, Aug. 10, 2015, *Masimo Corporation v. Shenzhen Mindray Bio-Medical Electronics Co., Ltd.*, Case No. SACV12-02206 CJC (DFMx).
[Proposed] Order Granting Shenzhen Mindray Biomedical Electronics Co., Ltd's Motion To Exclude The Expert Testimony Of Vijay Madisetti, D.I. 627-16, Aug. 10, 2015, *Masimo Corporation v. Shenzhen Mindray Bio-Medical Electronics Co., Ltd.*, Case No. SACV12-02206 CJC (DFMx).
Shenzhen Mindray Biomedical Electronics Co., Ltd.'s Notice Of Motion And Motion For Partial Summary Judgment On Priority Date Of U.S. Pat. No. 6,745,060, D.I. 634, Aug. 10, 2015, *Masimo Corporation v. Shenzhen Mindray Bio-Medical Electronics Co., Ltd.*, Case No. SACV12-02206 CJC (DFMx).
Memorandum Of Points And Authorities In Support Of Shenzhen Mindray Biomedical Electronics Co., Ltd.'s Motion For Partial Summary Judgment On Priority Date Of U.S. Pat. No. 6,745,060, D.I. 634-1, Aug. 10, 2015, *Masimo Corporation v. Shenzhen Mindray Bio-Medical Electronics Co., Ltd.*, Case No. SACV12-02206 CJC (DFMx).
Statement Of Uncontroverted Facts And Conclusions Of Law In Support Of Shenzhen Mindray Bio-Medical Electronics Co., Ltd.'s Motion For Partial Summary Judgment On Priority Date Of U.S. Pat.
No. 6,745,060, D.I. 634-2, Aug. 10, 2015, *Masimo Corporation v. Shenzhen Mindray Bio-Medical Electronics Co., Ltd.*, Case No. SACV12-02206 CJC (DFMx).
Declaration Of Scott A. Penner In Support Of Shenzhen Mindray Biomedical Electronics Co., Ltd.'s Motion For Partial Summary Judgment On Priority Date Of U.S. Pat. No. 6,745,060, D.I. 634-3, Part 1, Aug. 10, 2015, *Masimo Corporation v. Shenzhen Mindray Bio-Medical Electronics Co., Ltd.*, Case No. SACV12-02206 CJC (DFMx).
Declaration Of Scott A. Penner In Support Of Shenzhen Mindray Biomedical Electronics Co., Ltd.'s Motion For Partial Summary Judgment On Priority Date Of U.S. Pat. No. 6,745,060, D.I. 634-3, Part 2, Aug. 10, 2015, *Masimo Corporation v. Shenzhen Mindray Bio-Medical Electronics Co., Ltd.*, Case No. SACV12-02206 CJC (DFMx).
Declaration Of Scott A. Penner In Support Of Shenzhen Mindray Biomedical Electronics Co., Ltd.'s Motion For Partial Summary Judgment On Priority Date Of U.S. Pat. No. 6,745,060, D.I. 634-3, Part 3, Aug. 10, 2015, *Masimo Corporation v. Shenzhen Mindray Bio-Medical Electronics Co., Ltd.*, Case No. SACV12-02206 CJC (DFMx).
Declaration Of Scott A. Penner In Support Of Shenzhen Mindray Biomedical Electronics Co., Ltd.'s Motion For Partial Summary Judgment On Priority Date Of U.S. Pat. No. 6,745,060, D.I. 634-3, Part 4, Aug. 10, 2015, *Masimo Corporation v. Shenzhen Mindray Bio-Medical Electronics Co., Ltd.*, Case No. SACV12-02206 CJC (DFMx).
Declaration Of Scott A. Penner In Support Of Shenzhen Mindray Biomedical Electronics Co., Ltd.'s Motion For Partial Summary Judgment On Priority Date Of U.S. Pat. No. 6,745,060, D.I. 634-3, Part 5, Aug. 10, 2015, *Masimo Corporation v. Shenzhen Mindray Bio-Medical Electronics Co., Ltd.*, Case No. SACV12-02206 CJC (DFMx).
Declaration Of Scott A. Penner In Support Of Shenzhen Mindray Biomedical Electronics Co., Ltd.'s Motion For Partial Summary Judgment On Priority Date Of U.S. Pat. No. 6,745,060, D.I. 634-3, Part 6, Aug. 10, 2015, *Masimo Corporation v. Shenzhen Mindray Bio-Medical Electronics Co., Ltd.*, Case No. SACV12-02206 CJC (DFMx).
Declaration Of Scott A. Penner In Support Of Shenzhen Mindray Biomedical Electronics Co., Ltd.'s Motion For Partial Summary Judgment On Priority Date Of U.S. Pat. No. 6,745,060, D.I. 634-3, Part 7, Aug. 10, 2015, *Masimo Corporation v. Shenzhen Mindray Bio-Medical Electronics Co., Ltd.*, Case No. SACV12-02206 CJC (DFMx).
[Proposed] Order Granting Shenzhen Mindray Biomedical Electronics Co., Ltd.'s Motion For Partial Summary Judgment On Priority Date Of U.S. Pat. No. 6,745,060, D.I. 634-25, Aug. 10, 2015, *Masimo Corporation v. Shenzhen Mindray Bio-Medical Electronics Co., Ltd.*, Case No. SACV12-02206 CJC (DFMx).
[Redacted] Philips' Opening Markman Brief, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 1, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 2, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 3, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 4, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 5, Aug. 18, 2015, *Masimo Corporation v. Shenzhen Mindray Bio-Medical Electronics Co., Ltd.*, Case No. SACV12-02206 CJC (DFMx).

(56) References Cited

OTHER PUBLICATIONS

Phillips Exhibits 1-15 to Opening Markman Brief (AEO Exhibits 10, 12, and 13 Removed), Part 6, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 7, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 8, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 9, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 10, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 11, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 12, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 13, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 14, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 15, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 16, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 17, Aug. 18, 2015, *Masimo Corporation v. Shenzhen Mindray Bio-Medical Electronics Co., Ltd.*, Case No. SACV12-02206 CJC (DFMx).
Phillips Exhibits 1-15 to Opening Markman Brief (AEO Exhibits 10, 12, and 13 Removed), Part 18, Aug. 18, 2015, *Masimo Corporation v. Shenzhen Mindray Bio-Medical Electronics Co., Ltd.*, Case No. SACV12-02206 CJC (DFMx).
[Redacted] Masimo's Answering Markman and Opposition to Phillips Summary Judgment, Sep. 4, 2015, *Masimo Corporation v. Shenzhen Mindray Bio-Medical Electronics Co., Ltd.*, Case No. SACV12-02206 CJC (DFMx).
Masimo's Exhibit 16-17 to Answering Markman Brief and Opposition to Phillips, Sep. 4, 2015, *Masimo Corporation v. Shenzhen Mindray Bio-Medical Electronics Co., Ltd.*, Case No. SACV12-02206 CJC (DFMx).
Deposition Transcript of Robert Stone [Mini], Jul. 16, 2015, *Masimo Corporation v. Shenzhen Mindray Bio-Medical Electronics Co., Ltd.*, Case No. SACV12-02206 CJC (DFMx).
Deposition Transcript of Mohamed Diab [Non-Confidential] [Mini], Jul. 17, 2015, *Masimo Corporation v. Shenzhen Mindray Bio-Medical Electronics Co., Ltd.*, Case No. SACV12-02206 CJC (DFMx).
Deposition Transcript of Richard Meyst [Mini], Jul. 17, 2015, *Masimo Corporation v. Shenzhen Mindray Bio-Medical Electronics Co., Ltd.*, Case No. SACV12-02206 CJC (DFMx).
Deposition Transcript of Stephen Kunin [Mini], Jul. 21, 2015, *Masimo Corporation v. Shenzhen Mindray Bio-Medical Electronics Co., Ltd.*, Case No. SACV12-02206 CJC (DFMx).
Deposition Transcript of Thomas Scharf [Mini], Jul. 22, 2015, *Masimo Corporation v. Shenzhen Mindray Bio-Medical Electronics Co., Ltd.*, Case No. SACV12-02206 CJC (DFMx).
Deposition Transcript of Nitin Shah [Mini], Jul. 23, 2015, *Masimo Corporation v. Shenzhen Mindray Bio-Medical Electronics Co., Ltd.*, Case No. SACV12-02206 CJC (DFMx).
Deposition Transcript of James Corenman [Mini], Jul. 24, 2015, *Masimo Corporation v. Shenzhen Mindray Bio-Medical Electronics Co., Ltd.*, Case No. SACV12-02206 CJC (DFMx).
Errata Sheet, signature page of Stephen Kunin, Aug. 10, 2015, *Masimo Corporation v. Shenzhen Mindray Bio-Medical Electronics Co., Ltd.*, Case No. SACV12-02206 CJC (DFMx).
Errata Sheet, signature page of Mohamed Diab, Aug. 24, 2015, *Masimo Corporation v. Shenzhen Mindray Bio-Medical Electronics Co., Ltd.*, Case No. SACV12-02206 CJC (DFMx).
Expert Report of Dennis E. Bahr, May 22, 2015, *Masimo Corporation v. Shenzhen Mindray Bio-Medical Electronics Co., Ltd.*, Case No. SACV12-02206 CJC (DFMx).
Expert Report of Dr. Nitin Shah, May 22, 2015, *Masimo Corporation v. Shenzhen Mindray Bio-Medical Electronics Co., Ltd.*, Case No. SACV12-02206 CJC (DFMx).
Expert Report of Dr. Robert T. Stone, May 22, 2015, *Masimo Corporation v. Shenzhen Mindray Bio-Medical Electronics Co., Ltd.*, Case No. SACV12-02206 CJC (DFMx).
Expert Report of James Corenman re Invalidity of Masimo's Patents, May 22, 2015, *Masimo Corporation v. Shenzhen Mindray Bio-Medical Electronics Co., Ltd.*, Case No. SACV12-02206 CJC (DFMx).
Expert Report of Michael Sofocleous, Part 1, May 22, 2015, *Masimo Corporation v. Shenzhen Mindray Bio-Medical Electronics Co., Ltd.*, Case No. SACV12-02206 CJC (DFMx).
Expert Report of Michael Sofocleous, Part 2, May 22, 2015, *Masimo Corporation v. Shenzhen Mindray Bio-Medical Electronics Co., Ltd.*, Case No. SACV12-02206 CJC (DFMx).
Expert Report of Thomas Scharf re Invalidity, May 22, 2015, *Masimo Corporation v. Shenzhen Mindray Bio-Medical Electronics Co., Ltd.*, Case No. SACV12-02206 CJC (DFMx).
[Redacted] Rebuttal Validity Report of Vijay Madisetti, Jun. 19, 2015, *Masimo Corporation v. Shenzhen Mindray Bio-Medical Electronics Co., Ltd.*, Case No. SACV12-02206 CJC (DFMx).
Disclosure of Expert Testimony of Mohamed Diab pursuant to Fed R. Civ P 26(a)(2)(C), Jun. 19, 2015, *Masimo Corporation v. Shenzhen Mindray Bio-Medical Electronics Co., Ltd.*, Case No. SACV12-02206 CJC (DFMx).
Rebuttal Expert Report for Stephen G Kunin, Jun. 19, 2015, *Masimo Corporation v. Shenzhen Mindray Bio-Medical Electronics Co., Ltd.*, Case No. SACV12-02206 CJC (DFMx).
Rebuttal Expert Report of Dr. Nitin Shah, Jun. 19, 2015, *Masimo Corporation v. Shenzhen Mindray Bio-Medical Electronics Co., Ltd.*, Case No. SACV12-02206 CJC (DFMx).
Rebuttal Expert Report of Professor Gail Dr. Baura Ph.D, Jun. 19, 2015, *Masimo Corporation v. Shenzhen Mindray Bio-Medical Electronics Co., Ltd.*, Case No. SACV12-02206 CJC (DFMx).
Rebuttal Expert Report of Richard Meyst, Jun. 19, 2015, *Masimo Corporation v. Shenzhen Mindray Bio-Medical Electronics Co., Ltd.*, Case No. SACV12-02206 CJC (DFMx).
Rebuttal Expert Report of Thomas Scharf, Jun. 19, 2015, *Masimo Corporation v. Shenzhen Mindray Bio-Medical Electronics Co., Ltd.*, Case No. SACV12-02206 CJC (DFMx).
Errata to Expert Report of James Corenman re Invalidity of the Patents, Jul. 21, 2015, *Masimo Corporation v. Shenzhen Mindray Bio-Medical Electronics Co., Ltd.*, Case No. SACV12-02206 CJC (DFMx).
Errata to Expert Report of Dr. Robert T. Stone, Jul. 24, 2015, *Masimo Corporation v. Shenzhen Mindray Bio-Medical Electronics Co., Ltd.*, Case No. SACV12-02206 CJC (DFMx).
Masimo's Opposition to Shenzhen Mindray's Motion to Exclude the Expert Testimony of Dr. Nitin Shah, D.I. 658, Aug. 31, 2015, *Masimo Corporation v. Shenzhen Mindray Bio-Medical Electronics Co., Ltd.*, Case No. SACV12-02206 CJC (DFMx).

(56) References Cited

OTHER PUBLICATIONS

Declaration of Mark D. Kachner in Support of Masimo's Opposition to Shenzhen Mindray's Motion to Exclude the Expert Testimony of Dr. Nitin Shah, D.I. 658-1, Aug. 31, 2015, *Masimo Corporation v. Shenzhen Mindray Bio-Medical Electronics Co., Ltd.*, Case No. SACV12-02206 CJC (DFMx).

Masimo's Opposition to Shenzhen Mindray's Motion to Exclude Expert Testimony of Richard Meyst, D.I. 664, Aug. 31, 2015, *Masimo Corporation v. Shenzhen Mindray Bio-Medical Electronics Co., Ltd.*, Case No. SACV12-02206 CJC (DFMx).

Declaration of Michael C. Lee in Support of Masimo's Opposition to Shenzhen Mindray's Motion to Exclude the Expert Testimony of Richard Meyst, D.I. 664-1, Aug. 31, 2015, *Masimo Corporation v. Shenzhen Mindray Bio-Medical Electronics Co., Ltd.*, Case No. SACV12-02206 CJC (DFMx).

Masimo's Opposition to Shenzhen Mindray's Motion to Exclude Expert Testimony of Mohamed Diab and Any Reliance on His Expert Opinions, D.I. 669, Aug. 31, 2015, *Masimo Corporation v. Shenzhen Mindray Bio-Medical Electronics Co., Ltd.*, Case No. SACV12-02206 CJC (DFMx).

Declaration of Mohamed K. Diab in Support of Masimo's Opposition to Shenzhen Mindray's Motion to Exclude the Expert Testimony of Mohamed Diab and Any Reliance on His Expert Opinions, D.I. 669-1, Aug. 31, 2015, *Masimo Corporation v. Shenzhen Mindray Bio-Medical Electronics Co., Ltd.*, Case No. SACV12-02206 CJC (DFMx).

Declaration of Jon W. Gurka in Support of Masimo's Opposition to Mindray's Motion to Exclude Testimony of Mohamed Diab, D.I. 669-2, Aug. 31, 2015, *Masimo Corporation v. Shenzhen Mindray Bio-Medical Electronics Co., Ltd.*, Case No. SACV12-02206 CJC (DFMx).

[Public] Masimo's Opposition to Shenzhen Mindray's Motion for Summary Judgment of Invalidity of U.S. Pat. No. 7,489,958, D.I. 670, Aug. 31, 2015, *Masimo Corporation v. Shenzhen Mindray Bio-Medical Electronics Co., Ltd.*, Case No. SACV12-02206 CJC (DFMx).

Declaration of Perry D. Oldham in Support of Masimo's Opposition to Shenzhen Mindray's Motion for Summary Judgment on Invalidity of U.S. Pat. No. 7,489,958, D.I. 670-1, Aug. 31, 2015, *Masimo Corporation v. Shenzhen Mindray Bio-Medical Electronics Co., Ltd.*, Case No. SACV12-02206 CJC (DFMx).

Statement of Genuine Disputes of Material Fact by Masimo Re Shenzhen Mindray's Motion for Summary Judgment of Invalidity of U.S. Pat. No. 7,489,958, D.I. 676, Aug. 31, 2015, *Masimo Corporation v. Shenzhen Mindray Bio-Medical Electronics Co., Ltd.*, Case No. SACV12-02206 CJC (DFMx).

[Public] Masimo's Opposition to Shenzhen Mindray's Motion for Partial Summary Judgment of No Direct Infringement, No Pre-Suit Indirect Infringement, and No Willful Infringement, D.I. 683, Aug. 31, 2015, *Masimo Corporation v. Shenzhen Mindray Bio-Medical Electronics Co., Ltd.*, Case No. SACV12-02206 CJC (DFMx).

[Public] Declaration of Joe Kiani in Support of Masimo's Opposition to Shenzhen Mindray's Motion for Summary Judgment and No Direct Infringement, No Pre-Suit Indirect Infringement, and No Willful Infringement, D.I. 683-1, Aug. 31, 2015, *Masimo Corporation v. Shenzhen Mindray Bio-Medical Electronics Co., Ltd.*, Case No. SACV12-02206 CJC (DFMx).

[Public] Declaration of Stephen C. Jensen in Support of Masimo's Opposition to Shenzhen Mindray's Motion for Summary Judgment and No Direct Infringement, No Pre-Suit Indirect Infringement, and No Willful Infringement, D.I. 683-3, Aug. 31, 2015, *Masimo Corporation v. Shenzhen Mindray Bio-Medical Electronics Co., Ltd.*, Case No. SACV12-02206 CJC (DFMx).

[Public] Statement of Genuine Disputes of Material Fact by Masimo Regarding Shenzhen Mindray's Motion for Summary Judgment and No Direct Infringement, No Pre-Suit Indirect Infringement, and No Willful Infringement, D.I. 684, Aug. 31, 2015, *Masimo Corporation v. Shenzhen Mindray Bio-Medical Electronics Co., Ltd.*, Case No. SACV12-02206 CJC (DFMx).

Declaration of Michael C. Lee in Support of Masimo's Opposition to Shenzhen Mindray's Motion for Summary Judgment and No Direct Infringement, No Pre-Suit Indirect Infringement, and No Willful Infringement, D.I. 685, Aug. 31, 2015, *Masimo Corporation v. Shenzhen Mindray Bio-Medical Electronics Co., Ltd.*, Case No. SACV12-02206 CJC (DFMx).

[Public] Masimo's Opposition re Shenzhen Mindray's Motion for Partial Summary Judgment on Priority Date of U.S. Pat. No. 6,745,060, D.I 688, Aug. 31, 2015, *Masimo Corporation v. Shenzhen Mindray Bio-Medical Electronics Co., Ltd.*, Case No. SACV12-02206 CJC (DFMx).

[Public] Masimo's Statement of Genuine Disputes of Material Fact re Shenzhen Mindray's Motion for Partial Summary Judgment on Priority Date of U.S. Pat. No. 6,745,060, D.I. 689, Aug. 31, 2015, *Masimo Corporation v. Shenzhen Mindray Bio-Medical Electronics Co., Ltd.*, Case No. SACV12-02206 CJC (DFMx).

Declaration Of Perry D. Oldham In Support of Masimo's Opposition to Shenzhen Mindray's Motion for Partial Summary Judgment on Priority Date of U.S. Pat. No. 6,745,060, D.I. 690, Aug. 31, 2015, *Masimo Corporation v. Shenzhen Mindray Bio-Medical Electronics Co., Ltd.*, Case No. SACV12-02206 CJC (DFMx).

Memorandum in Opposition to Masimo Corporation and Masimo International Sarl's Motion for Summary Judgment of No Prosecution Laches, D.I. 696, Aug. 31, 2015, *Masimo Corporation v. Shenzhen Mindray Bio-Medical Electronics Co., Ltd.*, Case No. SACV12-02206 CJC (DFMx).

Statement of Genuine Disputes of Material Fact in Opposition to Masimo's Motion for Summary Judgment of No Prosecution Laches, D.I. 696-1, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 1, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 2, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 3, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 4, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 5, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 6, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 7, Aug. 31, 2015, *Masimo Corporation v. Shenzhen Mindray Bio-Medical Electronics Co., Ltd.*, Case No. SACV12-02206 CJC (DFMx).

(56) References Cited

OTHER PUBLICATIONS

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 8, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 9, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 10, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Shenzhen Mindray Bio-Medical Electronics Co., Ltd.'s Opposition to Masimo Corporation and Masimo International Sarl's Motion for Summary Judgment of No Prosecution Laches, D.I. 696-2, Part 11, Aug. 31, 2015, *Masimo Corporation v. Shenzhen Mindray Bio-Medical Electronics Co., Ltd.*, Case No. SACV12-02206 CJC (DFMx).

[Public] Masimo's Opposition to Shenzhen Mindray's Motion to Exclude Expert Testimony of Vijay Madisetti, D.I. 710, Aug. 31, 2015, *Mashimo Corporation v. Shenzhen Mindray Bio-Medical Electronics Co., Ltd.*, Case No. SACV12-02206 CJC (DFMx).

Declaration of Mohamed Diab in Support of Masimo's Opposition to Shenzhen Mindray's Motion to Exclude Expert Testimony of Vijay Madisetti, D.I. 710-1, Aug. 31, 2015, *Masimo Corporation v. Shenzhen Mindray Bio-Medical Electronics Co., Ltd.*, Case No. SACV12-02206 CJC (DFMx), Declaration of Perry D. Oldham in Support of Masimo's Opposition to Shenzhen Mindray's Motion to Exclude Expert Testimony of Vijay Madisetti, D.I. 710-2, Part 1, Aug. 31, 2015, *Masimo Corporation v. Shenzhen Mindray Bio-Medical Electronics Co., Ltd.*, Case No. SACV12-02206 CJC (DFMx).

Declaration of Perry D. Oldham in Support of Masimo's Opposition to Shenzhen Mindray's Motion to Exclude Expert Testimony of Vijay Madisetti, D.I. 710-2, Part 2, Aug. 31, 2015, *Masimo Corporation v. Shenzhen Mindray Bio-Medical Electronics Co., Ltd.*, Case No. SACV12-02206 CJC (DFMx).

Declaration of Perry D. Oldham in Support of Masimo's Opposition to Shenzhen Mindray's Motion to Exclude Expert Testimony of Vijay Madisetti, D.I. 710-2, Part 3, Aug. 31, 2015, *Masimo Corporation v. Shenzhen Mindray Bio-Medical Electronics Co., Ltd.*, Case No. SACV12-02206 CJC (DFMx).

Declaration of Vijay Madisetti in Support of Masimo's Opposition to Shenzhen Mindray's Motion to Exclude Expert Testimony of Vijay Madisetti, D.I. 719, Aug. 31, 2015, *Masimo Corporation v. Shenzhen Mindray Bio-Medical Electronics Co., Ltd.*, Case No. SACV12-02206 CJC (DFMx).

[Redacted] Memorandum in Opposition to Masimo Corporation and Masimo International Sarl's Motion for Summary Judgment of No Inequitable Conduct, D.I. 725, Aug. 31, 2015, *Masimo Corporation v. Shenzhen Mindray Bio-Medical Electronics Co., Ltd.*, Case No. SACV12-02206 CJC (DFMx).

[Redacted] Statement of Genuine Disputes of Material Fact and Conclusions of Law in Opposition to Masimo's Motion for Summary Judgment of No Inequitable Conduct, D.I. 725-1, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 1, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 2, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 3, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 4, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 5, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 6, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 7, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 8, Aug. 31, 2015, *Masimo Corporation v. Shenzhen Mindray Bio-Medical Electronics Co., Ltd.*, Case No. SACV12-02206 CJC (DFMx).

Declaration of Nicola A. Pisano in Support of Opposition to Masimo Corporation and Masimo International Sarl's Motion for Summary Judgment of No Inequitable Conduct, D.I. 725-2, Part 9, Aug. 31, 2015, *Masimo Corporation v. Shenzhen Mindray Bio-Medical Electronics Co., Ltd.*, Case No. SACV12-02206 CJC (DFMx).

Reply in Support of Shenzhen Mindray Bio-Medical Electronics Co., Ltd.'s Motion for Summary Judgment of Invalidity of U.S. Pat. No. 7,489,958, D.I. 735, Sep. 14, 2015, Case No. SACV12-02206 CJC (DFMx).

Statement of Genuine Disputes of Materials Fact in Response to Masimo's Additional Facts in Opposition to Shenzhen Mindray's Motion for Summary Judgment of Invalidity of U.S. Pat. No. 7,489,958, D.I. 735-1, Sep. 14, 2015, Case No. SACV12-02206 CJC (DFMx).

Reply in Support of Shenzhen Mindray Bio-Medical Electronics Co., Ltd.'s Motion to Exclude the Expert Testimony of Dr. Nitin Shah, D.I. 736, Sep. 14, 2015, Case No. SACV12-02206 CJC (DFMx).

Reply Memorandum in Support of Shenzhen Mindray Bio-Medical Electronics Co., Ltd.'s Motion to Exclude the Expert Testimony of Richard Meyst, D.I. 745, Sep. 14, 2015, Case No. SACV12-02206 CJC (DFMx).

Declaration of Scott A. Penner in Support of Shenzhen Mindray Bio-Medical Electronics Co., Ltd.'s Motion to Exclude the Expert Testimony of Richard Meyst, D.I. 745-1, Sep. 14, 2015, Case No. SACV12-02206 CJC (DFMx).

Masimo's Reply Brief in Support of their Motion for Summary Judgment of no Prosecution Laches, D.I. 751, Sep. 14, 2015, Case No. SACV12-02206 CJC (DFMx).

Masimo's Reply Brief in Support of their Motion for Summary Judgment of no Inequitable Conduct, D.I. 753, Sep. 14, 2015, Case No. SACV12-02206 CJC (DFMx).

Supplemental Declaration of Nicholas A. Belair in Support of Masimo's Reply Brief in Support of its Motion for Summary Judgment of no Inequitable Conduct, D.I. 755, Sep. 14, 2015, Case No. SACV12-02206 CJC (DFMx).

(56) References Cited

OTHER PUBLICATIONS

Reply in Support of Shenzhen Mindray Bio-Medical Electronics Co., Ltd.'s Motion to Exclude the Expert Testimony of Mohamed Diab and any Reliance on his Expert Opinions, D.I. 760, Sep. 14, 2015, Case No. SACV12-02206 CJC (DFMx).
Supplemental Declaration of Nicola A. Pisano in Support of Shenzhen Mindray Bio-Medical Electronics Co., Ltd.'s Reply in Support of Motion to Exclude the Expert Testimony of Mohamed Diab and any Reliance on his Expert Opinions, D.I. 760-1, Sep. 14, 2015, Case No. SACV12-02206 CJC (DFMx).
Reply Memorandum in Support of Shenzhen Mindray Bio-Medical Electronics Co., Ltd.'s Motion to Exclude the Expert Testimony of Vijay Madisetti, D.I. 767, Sep. 14, 2015, Case No. SACV12-02206 CJC (DFMx).
Supplemental Declaration of Scott A. Penner in Support of Shenzhen Mindray Bio-Medical Electronics Co., Ltd.'s Reply in Support of its Motion to Exclude the Expert Testimony of Vijay Madisetti, D.I. 767-1, Sep. 14, 2015, Case No. SACV12-02206 CJC (DFMx).
Reply Memorandum in Support of Shenzhen Mindray Bio-Medical Electronics Co., Ltd.'s Motion for Partial Summary Judgment on Priority Date of U.S. Pat. No. 6,745,060, D.I. 779, Sep. 14, 2015, Case No. SACV12-02206 CJC (DFMx).
Supplemental Declaration of Scott A. Penner in Support of Shenzhen Mindray Bio-Medical Electronics Co., Ltd.'s Reply in Support of its Motion for Partial Summary Judgment on Priority Date of U.S. Pat. No. 6,745,060, D.I. 779-1, Sep. 14, 2015, Case No. SACV12-02206 CJC (DFMx).
Statement of Genuine Disputes of Material Fcts in Additional Statement of Genuine Disputes of Material Facts Re Shenzhen Mindray's Motion for Partial Summary Judgment on Priority Date of U.S. Pat. No. 6,745,060, D.I. 779-6, Sep. 14, 2015, Case No. SACV12-02206 CJC (DFMx).
Reply in Support of Shenzhen Mindray Bio-Medical Electronics Co., Ltd.'s Motion for Partial Summary Judgment of no Direct Infringement, no Pre-suit Indirect Infringement, and no Willful Infringement, D.I. 785, Sep. 14, 2015, Case No. SACV12-02206 CJC (DFMx).
Statement of Genuine Disputes of Material Facts in Response to Masimo's Additional Facts in Opposition to Shenzhen Mindray's Motion for Partial Summary Judgment of no Direct Infringement, No Pre-suit Indirect Infringement, and no Willful Infringement, D.I. 785-1, Sep. 14, 2015, Case No. SACV12-02206 CJC (DFMx).
Declaration of Justin E. Gray in Support of Shenzhen Mindray Bio-Medical Electronics Co., Ltd.'s Reply in Support of Motion for Partial Summary Judgment of no Direct Infringement, No Pre-suit Indirect Infringement, and no Willful Infringement, D.I. 785-2, Sep. 14, 2015, Case No. SACV12-02206 CJC (DFMx).
[Public] Joint Claim Construction Brief (Masimo II) and Joint Brief Related to Philips' Motion for Summary Judgment on Indefiniteness, Sep. 17, 2015, *Masimo Corp.* v. *Philips Elecs. North America Corp. et al.*, No. 1:09-cv-00080-LPS-MPT (D. Del.).
[Public] Appendix of Exhibits in Support of the Joint Claim Construction brief (Masimo II) and Joint Brief Related to Philips' Motion for Summary Judgment on Indefiniteness, vol. 1—Exhibits 1-9, Sep. 17, 2015, *Masimo Corp.* v. *Philips Elecs. North America Corp. et al.*, No. 1:09-cv-00080-LPS-MPT (D. Del.).
[Public] Appendix of Exhibits in Support of the Joint Claim Construction brief (Masimo II) and Joint Brief Related to Philips' Motion for Summary Judgment on Indefiniteness, vol. II—Exhibits 10-23, Sep. 17, 2015, *Masimo Corp.* v. *Philips Elecs. North America Corp. et al.*, No. 1:09-cv-00080-LPS-MPT (D. Del.).
[Public] Exhibits 18-19 in Support of the Joint Claim Construction brief (Masimo II) and Joint Brief Related to Philips' Motion for Summary Judgment on Indefiniteness, Sep. 17, 2015, *Masimo Corp.* v. *Philips Elecs. North America Corp. et al.*, No. 1:09-cv-00080-LPS-MPT (D. Del.).
[Public] Exhibits 20, Part 1, in Support of the Joint Claim Construction brief (Masimo II) and Joint Brief Related to Philips' Motion for Summary Judgment on Indefiniteness, Sep. 17, 2015, *Masimo Corp.* v. *Philips Elecs. North America Corp et al.*, No. 1:09-cv-00080-LPS-MPT (D. Del.).
[Public] Exhibits 20, Part 2, in Support of the Joint Claim Construction brief (Masimo II) and Joint Brief Related to Philips' Motion for Summary Judgment on Indefiniteness, Sep. 17, 2015, *Masimo Corp.* v. *Philips Elecs. North America Corp et al.*, No. 1:09-cv-00080-LPS-MPT (D. Del.).
[Public] Exhibits 20, Part 3, in Support of the Joint Claim Construction brief (Masimo II) and Joint Brief Related to Philips' Motion for Summary Judgment on Indefiniteness, Sep. 17, 2015, *Masimo Corp.* v. *Philips Elecs. North America Corp et al.*, No. 1:09-cv-00080-LPS-MPT (D. Del.).
[Public] Exhibits 20, Part 4, in Support of the Joint Claim Construction brief (Masimo II) and Joint Brief Related to Philips' Motion for Summary Judgment on Indefiniteness, Sep. 17, 2015, *Masimo Corp.* v. *Philips Elecs. North America Corp et al.*, No. 1:09-cv-00080-LPS-MPT (D. Del.).
[Public] Exhibits 20, Part 5, in Support of the Joint Claim Construction brief (Masimo II) and Joint Brief Related to Philips' Motion for Summary Judgment on Indefiniteness, Sep. 17, 2015, *Masimo Corp.* v. *Philips Elecs. North America Corp et al.*, No. 1:09-cv-00080-LPS-MPT (D. Del.).
[Public] Exhibits 21-23, in Support of the Joint Claim Construction brief (Masimo II) and Joint Brief Related to Philips' Motion for Summary Judgment on Indefiniteness, Sep. 17, 2015, *Masimo Corp.* v. *Philips Elecs. North America Corp et al.*, No. 1:09-cv-00080-LPS-MPT (D. Del.).
Order Denying Parties' Applications to File Under Seal, Motions for Partial Summary Judgment, and Motions to Exclude Experts, D.I. 789, Sep. 24, 2015, *Masimo Corporation* v. *Shenzhen Mindray Bio-Medical Electronics Co., Ltd.*, Case No. SACV12-02206 CJC (DFMx) (C.D. Cal.).
Joint Claim Construction Brief (Masimo II) and Joint Brief related to Philips' Motion for Summary Judgment on Indefiniteness, Public Version, C.A. No. 11-742-LPS-MPT, Public Version dated Sep. 23, 2015.
Appendix of Exhibits in Support of the Joint Claim Construction Brief (Masimo II) and Joint Brief Related to Philips' Motion for Summary Judgment on Indefiniteness, vol. I—Exhibits 1-9, Public Version dated Sep. 23, 2015.
Appendix of Exhibits in Support of the Joint Claim Construction Brief (Masimo II) and Joint Brief Related to Philips' Motion for Summary Judgment on Indefiniteness, vol. II—Exhibits 10-23, Public Version dated Sep. 23, 2015.
Exhibits 18-19 in C.A. No. CV-00/6506 MRP (AJWx).
Exhibit 20 in C.A. No. 11-742-LPS-MPT.
Exhibits 21-23 in C.A. No. CV-00/6506 MRP (AJWx) and 09-80-LPS-MPT.
Transcript of Video Demonstration of Pulse Oximetry and the Fast Fourier Transform, Thomas Scharf, received May 21, 2015, transcribed Sep. 28, 2015, *Masimo Corporation* v. *Shenzhen Mindray Bio-Medical Electronics Co., Ltd.*, Case No. SACV12-02206 CJC (DFMx) (C.D. Cal.).
Transcript of Video Demonstration of Efficacy of the Frequency Domain Algorithm with Regard to Rejection of Motion Artifact, Dr. Robert T. Stone, received May 21, 2015, transcribed, Sep. 28, 2015, *Masimo Corporation* v. *Shenzhen Mindray Bio-Medical Electronics Co., Ltd.*, Case No. SACV12-02206 CJC (DFMx) (C.D. Cal.).
[807] [Redacted] Memorandum in Opposition to Masimo Corporation and Masimo International Sarl's Motion In Limine, *Masimo Corporation and Masimo International Sarl* v. *Shenzhen Mindray Bio-Medical Electronics Co., Ltd.*, Case 8:12-cv-02206-CJC-DFM, Filed Oct. 26, 2015, 14 pgs.
[807-1] Declaration of Justin E. Gray in Support of Shenzhen Mindray's Opposition to Masimo Corporation and Masimo International Sarl's Motion In Limine, *Masimo Corporation and Masimo International Sarl* v. *Shenzhen Mindray Bio-Medical Electronics Co., Ltd*, Case 8:12-cv-02206-CJC-DFM, Filed Oct. 26, 2015, 35 pgs.

(56) References Cited

OTHER PUBLICATIONS

[814] Masimo's Reply in Support of Its Motion In Limine to Preclude Irrelevant Attacks on the Lawyers at Knobbe Martens, *Masimo Corporation and Masimo International Sarl* v. *Shenzhen Mindray Bio-Medical Electronics Co., Ltd*, Case 8:12-cv-02206-CJC-DFM, Filed Nov. 2, 2015, 12 pgs.

Memorandum Opinion, D.I. 103, Dec. 1, 2015, *Masimo Corp.* v. *Philips Elecs. North America Corp. et al.*, No. 1:09-cv-00080-LPS-MPT, 1:11-cv-00742-LPS-MPT (D. Del.).

Order, D.I. 104, Dec. 1, 2015, *Masimo Corp.* v. *Philips Elecs. North America Corp. et al.*, No. 1:09-cv-00080-LPS-MPT, 1:11-cv-00742-LPS-MPT (D. Del.).

* cited by examiner

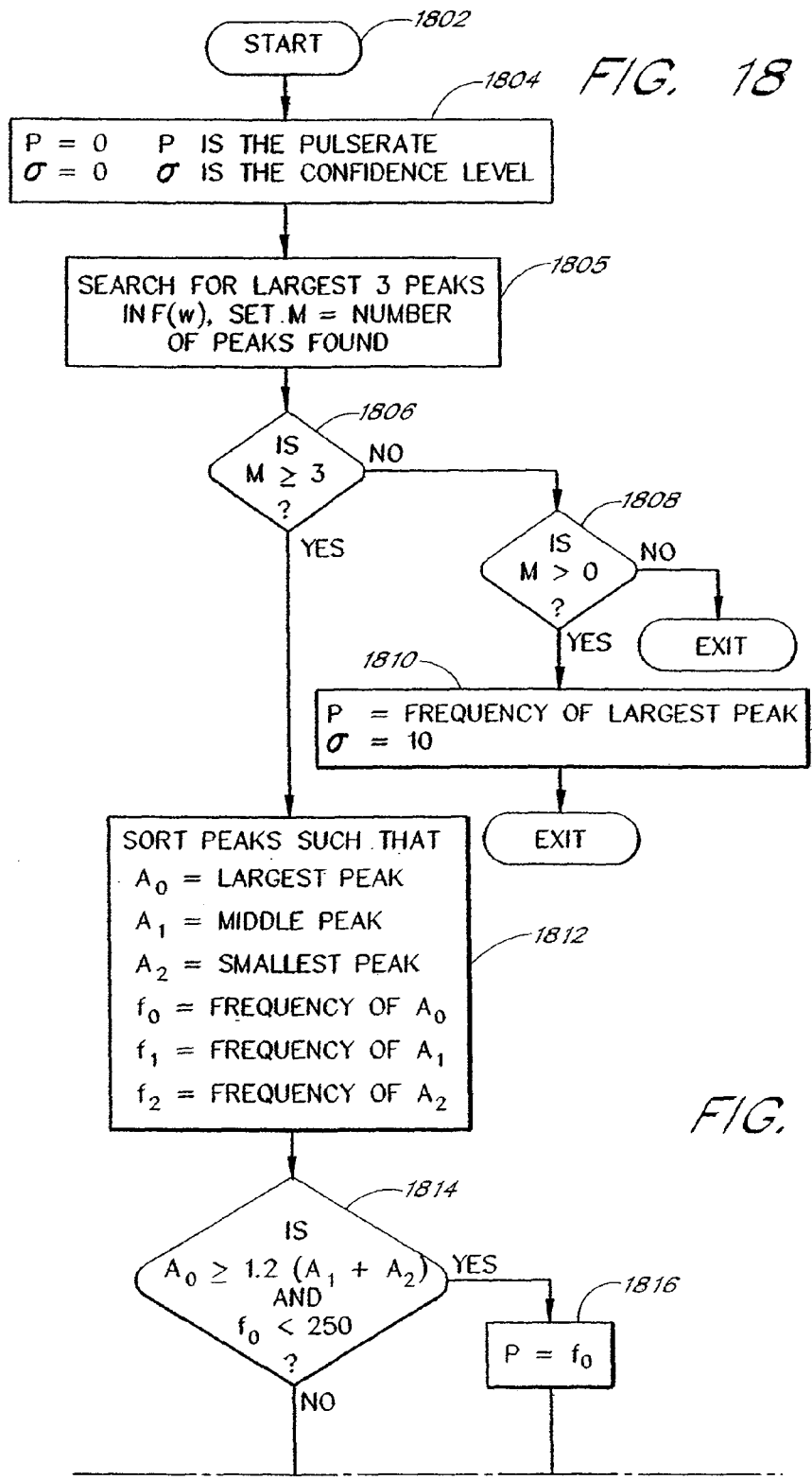

SIGNAL PROCESSING APPARATUS AND METHOD

PRIORITY CLAIM

This application is a continuation of U.S. application Ser. No. 13/471,340, filed May 14, 2012, which is a continuation of U.S. application Ser. No. 11/842,128, filed on Aug. 20, 2007, which is a continuation of U.S. application Ser. No. 10/791,683, filed on Mar. 2, 2004, which is a continuation of U.S. application Ser. No. 09/547,588, filed Apr. 11, 2000 (now U.S. Pat. No. 6,699,194), which is a continuation of U.S. application Ser. No. 09/081,539, filed May 19, 1998 (now U.S. Pat. No. 6,067,462), which is a divisional of U.S. application Ser. No. 08/834,194, filed Apr. 14, 1997 (now U.S. Pat. No. 6,002,952). The present application incorporates the foregoing disclosures herein by reference.

FIELD OF THE INVENTION

The present invention relates to the field of signal processing. More specifically, the present invention relates to the processing of measured signals, containing a primary signal portion and a secondary signal portion, for the removal or derivation of either the primary or secondary signal portion when little is known about either of these components. The present invention is especially useful for physiological monitoring systems including blood oxygen saturation systems and pulserate measurement systems. The present invention further relates to a method and apparatus for signal processing of signals in order to compute an estimate for pulserate.

BACKGROUND

Signal processors are typically employed to remove or derive either the primary or secondary signal portion from a composite measured signal including a primary signal portion and a secondary signal portion. For example, a composite signal may contain a primary signal portion comprising desirable data and a secondary signal portion comprising noise. If the secondary signal portion occupies a different frequency spectrum than the primary signal portion, then conventional filtering techniques such as low pass, band pass, and high pass filtering are available to remove or derive either the primary or the secondary signal portion from the total signal. Fixed single or multiple notch filters could also be employed if at least one of the primary and secondary signal portions exists at a fixed frequency band.

It is often the case that an overlap in frequency spectrum between the primary and secondary signal portions exists. Complicating matters further, the statistical properties of one or both of the primary and secondary signal portions may change with time. In such cases, conventional filtering techniques are ineffective in extracting either the primary or secondary signal. If, however, a description of either the primary or secondary signal portion can be derived, correlation canceling, such as adaptive noise canceling, can be employed to remove either the primary or secondary signal portion of the signal isolating the other portion. In other words, given sufficient information about one of the signal portions, that signal portion can be extracted.

Conventional correlation cancelers, such as adaptive noise cancelers, dynamically change their transfer function to adapt to and remove portions of a composite signal. However, correlation cancelers and adaptive noise cancelers require either a secondary reference or a primary reference which correlates to either the secondary signal portion only or the primary signal portion only. For instance, for a measured signal containing noise and desirable signal, the noise can be removed with a correlation canceler if a noise reference is available. This is often the case. Although the amplitudes of the reference signals are not necessarily the same as the amplitudes of the corresponding primary or secondary signal portions, the reference signals have a frequency spectrum which is similar to that of the primary or secondary signal portions.

In many cases, nothing or very little is known about the secondary and primary signal portions. One area where measured signals comprising a primary signal portion and a secondary signal portion about which no information can easily be determined is physiological monitoring. Physiological monitoring generally involves measured signals derived from a physiological system, such as the human body. Measurements which are typically taken with physiological monitoring systems include electrocardiographs, blood pressure, blood gas saturation (such as oxygen saturation), capnographs, other blood constituent monitoring, heart rate, respiration rate, electro-encephalograph (EEG) and depth of anesthesia, for example. Other types of measurements include those which measure the pressure and quantity of a substance within the body such as cardiac output, venous oxygen saturation, arterial oxygen saturation, bilirubin, total hemoglobin, breathalyzer testing, drug testing, cholesterol testing, glucose testing, and carbon dioxide testing, protein testing, carbon monoxide testing, and other in-vivo measurements, for example. Complications arising in these measurements are often due to motion of the patient, both external and internal (muscle movement, vessel movement, and probe movement, for example), during the measurement process.

Many types of physiological measurements can be made by using the known properties of energy attenuation as a selected form of energy passes through a test medium such as a finger, shown schematically in FIG. 1.

A blood gas monitor is one example of a physiological monitoring system which is based upon the measurement of energy attenuated by biological tissues or substances. Blood gas monitors transmit light into the test medium and measure the attenuation of the light as a function of time. The output signal of a blood gas monitor which is sensitive to the arterial blood flow contains a component having a waveform representative of the patient's arterial pulse. This type of signal, which contains a component related to the patient's pulse, is called a plethysmographic wave, and is shown in FIG. 2A as a curve s(t) 201. Plethysmographic waveforms are used in blood gas saturation measurements. As the heart beats, the amount of blood in the arteries increases and decreases, causing increases and decreases in energy attenuation, illustrated by a cyclic wave seen in the curve 201.

Typically, a digit such as a finger, an ear lobe, or other portion of the body where blood flows close to the skin, is employed as the medium through which light energy is transmitted for blood gas attenuation measurements. The finger comprises skin, fat, bone, muscle, etc., as shown FIG. 1, each of which attenuates energy incident on the finger in a generally predictable and constant manner. However, when fleshy portions of the finger are compressed erratically, for example by motion of the finger, energy attenuation becomes erratic.

An example of a more realistic measured waveform is shown in FIG. 2B, as a curve M(t) 202. The curve 202 illustrates the effect of motion and noise n(t) added to the clean waveform s(t) shown in FIG. 201. The primary plethysmographic waveform portion of the signal M(t) is the waveform representative of the pulse, corresponding to the sawtooth-like pattern wave in curve 201. The large, secondary motion-induced excursions in signal amplitude obscure the primary plethysmographic signal s(t). Even small variations in amplitude make it difficult to distinguish the primary signal component s(t) in the presence of a secondary signal component n(t).

A pulse oximeter is a type of blood gas monitor which non-invasively measures the arterial saturation of oxygen in the blood. The pumping of the heart forces freshly oxygenated blood into the arteries causing greater energy attenuation. As well understood in the art, the arterial saturation of oxygenated blood may be determined from the depth of the valleys relative to the peaks of two plethysmographic waveforms measured at separate wavelengths. Patient movement introduces motion artifacts to the composite signal as illustrated in the plethysmographic waveform illustrated in FIG. 2B. These motion artifacts distort the measured signal.

SUMMARY OF THE INVENTION

The present invention involves several different embodiments using the novel signal model in accordance with the present invention to estimate the desired signal portion of a measured data signal where the measured data contains desired and undesired components. In one embodiment, a signal processor acquires a first measured signal and a second measured signal. The first signal comprises a desired signal portion and an undesired signal portion. The second measured signal comprises a desired signal portion and an undesired signal portion. The signals may be acquired by propagating energy through a medium and measuring an attenuated signal after transmission or reflection. Alternatively, the signals may be acquired by measuring energy generated by the medium.

In one embodiment, the desired signal portions of the first and second measured signals are approximately equal to one another, to with a first constant multiplier. The undesired signal portions of the first and second measured signals are also approximately equal to one another, to within a second constant multiplier. A scrubber coefficient may be determined, such that an estimate for the first signal can be generated by inputting the first and second measured signals, and the scrubber coefficient into a waveform scrubber. The output of the waveform scrubber is generated by multiplying the first measured signal by the scrubber coefficient and then adding the result to the second measured signal.

In one embodiment, the scrubber coefficient is determined by normalizing the first and second measured signals, and then transforming the normalized signals into a spectral domain. The spectral domain signals are then divided by one another to produce a series of spectral ratio lines. The need for waveform scrubbing can be determined by comparing the largest ratio line to the smallest ratio line. If the difference does not exceed a threshold value, the no scrubbing is needed. If the difference does exceed a threshold value, then the waveform must be scrubbed, and the scrubbing coefficient corresponds to the magnitude of the largest ratio line.

Another aspect of the present invention involves a physiological monitor having a signal processor which computes an estimate for an unknown pulserate from the measured data. In one embodiment, the signal processor receives measured data from a detector that measures a physiological property related to the heartbeat. The signal processor transforms the data into a spectral domain and then identifies a series of spectral peaks and the frequencies associated with those peaks. The signal processor then applies a set of rules to the spectral peaks and the associated frequencies in order to compute an estimate for the pulserate.

In yet another embodiment of the pulserate detector, the signal processor performs a first transform to transform the measured data into a first transform space. The signal processor then performs a second transform to transform the data from the first transform space into a second transform space. The signal processor then searches the data in the second transform space to find the pulserate.

In another embodiment, the transform into the first transform space is a spectral transform such as a Fourier transform. In another embodiment, the transform into the second transform space is a spectral transform such as a Fourier transform. In yet another embodiment, once the data has been transformed into the second transform space, the signal processor performs a 1/x mapping on the spectral coordinates before searching for the pulserate.

In another embodiment, the signal processor transforms the measured data into a first spectral domain, and then transforms the data from the first spectral domain into a second spectral domain. After twice transforming the data, the signal processor performs a 1/x remapping on the coordinates of the second spectral domain. The signal processor then searches the remapped data for the largest spectral peak corresponding to a pulserate less than 120 beats per minute. If such a peak is found, then the signal processor outputs the frequency corresponding to that peak as being the pulserate. Otherwise, the signal processor searches the data transformed into the first spectral domain for the largest spectral peak in that domain, and outputs a pulserate corresponding to the frequency of the largest peak in the first spectral domain.

In another embodiment of the pulserate detector, the signal processor first transforms the measured data into a first spectral domain. Then the signal processor takes the magnitude of the transformed data and then transforms the magnitudes into a second spectral domain. Then the signal processor then performs a 1/x mapping of the spectral coordinates. After the 1/x mapping, the signal processor feeds the transformed and remapped data into a neural network. The output of the neural network is the pulserate.

BRIEF DESCRIPTION OF THE DRAWINGS

FIGS. 18A, 18B, and 18C are a flowchart showing the process steps of the rule based pulserate detection method.

DETAILED DESCRIPTION OF THE INVENTION

Figure 1:
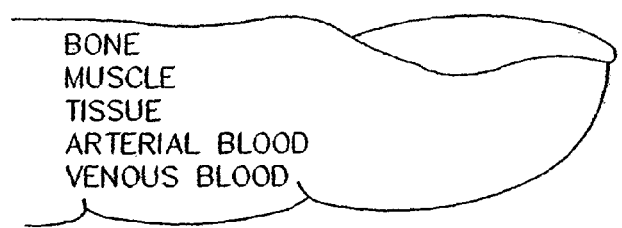
FIG. 1 schematically illustrates a typical finger.
Figure 2A:
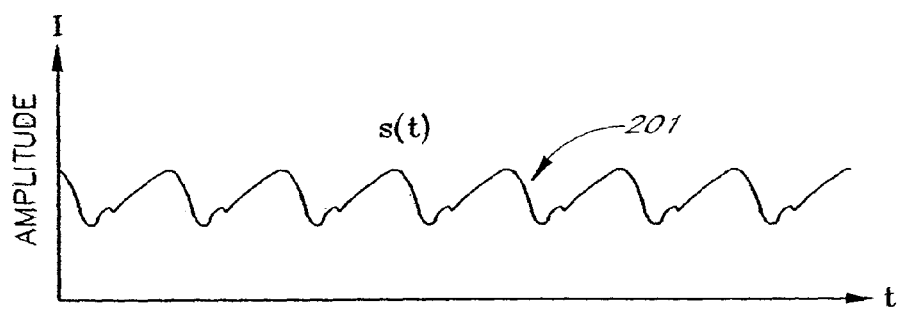
FIG. 2A illustrates an ideal plethysmographic waveform.
Figure 2B:
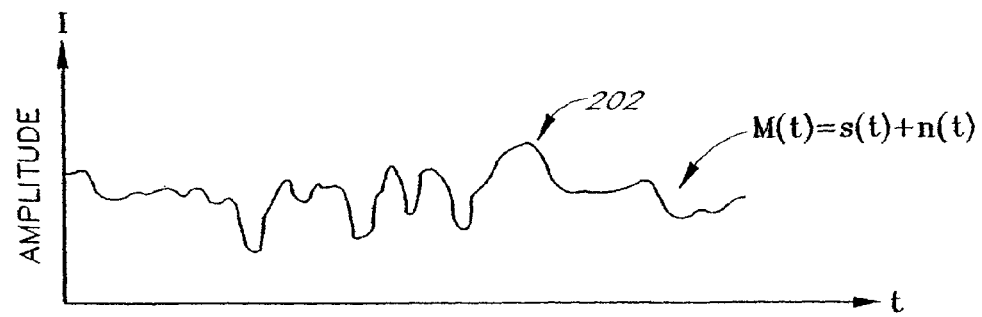
FIG. 2B illustrates a plethysmographic waveform which includes a motion induced erratic signal portion.

The present invention involves a system which uses first and second measured signals that each contain a primary signal portion and a secondary signal portion. In other words, given first and second composite signals $c_1(t)=s_1(t)+n_1(t)$ and $c_2(t)=s_2(t)+n_2(t)$, the system of the present invention can be used to isolate either the primary signal portion $s(t)$ or the secondary signal portion $n(t)$ of the two composite signals. Following processing, the output of the system provides a good approximation $n"(t)$ to the secondary signal portion $n(t)$ or a good approximation $s"(t)$ to the primary signal portion $s(t)$.

The system of the present invention is particularly useful where the primary signal portion $s(t)$, the secondary signal portion $n(t)$, or both, may contain one or more of a constant portion, a predictable portion, an erratic portion, a random portion, etc. The primary signal approximation $s"(t)$ or the secondary signal approximation $n"(t)$ is derived by removing as many of the secondary signal portions $n(t)$ or primary signal portions $s(t)$ from the composite signal $c(t)$ as possible. The remaining signal forms either the primary signal approximation $s"(t)$ or the secondary signal approximation $n"(t)$, respectively. The constant portion and the predictable portion of the secondary signal $n(t)$ are easily removed with traditional filtering techniques, such as simple subtraction, low pass, band pass, and high pass filtering. The erratic portion is more difficult to remove due to its unpredictable nature. If something is known about the erratic signal, even statistically, it could be removed, at least partially, from the measured signal via traditional filtering techniques. However, often no information is known about the erratic portion of the secondary signal $n(t)$. In this case, traditional filtering techniques are usually insufficient.

In order to remove the secondary signal $n(t)$, a signal model in accordance with the present invention is defined as follows for the first and second measured signals $c_1$ and $c_2$:

$$c_1 = s_1 + n_1 \quad (1)$$

$$c_2 = s_2 + n_2 \quad (2)$$

with $$s_1 = r_a s_2 \quad (3)$$

and $$n_1 = r_v n_2$$

or $$r_a = \frac{s_1}{s_2} \quad (4)$$

and $$r_v = \frac{n_1}{n_2}$$

where $s_1$ and $n_1$ are at least somewhat (preferably substantially) uncorrelated and $s_2$ and $n_2$ are at least somewhat (preferably substantially) uncorrelated. The first and second measured signals $c_1$ and $c_2$ are related by correlation coefficients $r_a$ and $r_v$ as defined above. The use and selection of these coefficients is described in further detail below.

In accordance with one aspect of the present invention this signal model is used in combination with a waveform scrubber to remove the undesired portion of the measured signals.

The description that follows can best be understood in view of the following list which briefly describes how the invention is broken down and described according to the following topics:

1. A general overview of pulse oximetry measurements, in connection with FIGS. 1 through 4, provides a general theory and system block diagram for a red/infrared pulse oximetry apparatus for measurement of physiological data such as blood oxygen saturation and pulserate;

2. A more detailed description of the relationship between the data RD(t) measured using red light, and the data IR(t) measured using infrared light, normalization of RD(t) and IR(t), and the relationship of the normalized RD(t) and IR(t) to blood oxygen saturation, is provided in connection with FIGS. 5 through 8;

3. A mathematical model and description of the effect of motion artifacts on RD(t) and IR(t) and a method for detecting and removing the artifacts to create a clean spectrum $F(\omega) = RD(\omega)/IR(\omega)$, are provided in connection with FIGS. 10 through 13;

4. A mathematical model and a description of a rule based signal processing technique used by the pulse oximeter to determine pulserate, are provided in connection with FIGS. 14 through 16; and 5. A mathematical model and a description of a transform based signal processing technique used by the pulse oximeter to determine pulserate, are provided in connection with FIG. 17.

Pulse Oximetry Measurements

A specific example of a physiological monitor using a processor of the present invention to determine a secondary reference $n'(t)$ for input to a canceler that removes erratic motion-induced secondary signal portions is a pulse oximeter. Pulse oximetry may also be performed using a processor of the present invention to determine a primary signal reference $s'(t)$ which may be used for display purposes or for input to a processor to derive information about patient movement, pulserate, and venous blood oxygen saturation.

A pulse oximeter typically causes energy to propagate through a medium where blood flows close to the surface, for example, an ear lobe, or a digit such as a finger, a forehead or a fetus' scalp. An attenuated signal is measured after propagation through or reflected from the medium. The pulse oximeter estimates the saturation of oxygenated blood.

Freshly oxygenated blood is pumped at high pressure from the heart into the arteries for use by the body. The volume of blood in the arteries and arterioles varies with the heartbeat, giving rise to a variation in absorption of energy at the rate of the heartbeat, or the pulse. The blood scatters both red and infrared light, and thus as the volume of blood changes, the amount of scattering changes as well. Typically the effects due to scattering are small when compared to the effects due to the change in blood volume.

Oxygen depleted, or deoxygenated, blood is returned to the heart by the veins along with unused oxygenated blood. The volume of blood in the veins varies with back pressure due to breathing as well as local uncontrolled motion of muscles. These variations typically occur at a rate that is much slower than the heartbeat. Thus, when there is no motion induced variation in the thickness of the veins, venous blood causes a low frequency variation in absorption of energy. When there is motion induced variation in the thickness of the veins, the scattering changes as well and this absorption is coupled with the erratic variation in absorption due to motion artifacts.

In absorption measurements using the transmission of energy through a medium, two light emitting diodes (LEDs) are positioned close to a portion of the body where blood flows close to the surface, such as a finger, and a photodetector is positioned near the LEDs. Typically, in pulse oximetry measurements, one LED emits a visible wavelength, preferably red, and the other LED emits an infrared wavelength. However, one skilled in the art will realize that other wavelength combinations, as well as combinations of more than two wavelengths, could be used. The finger comprises skin, tissue, muscle, both arterial blood and venous blood, fat, etc., each of which absorbs light energy differently due to different absorption coefficients, different concentrations, different thicknesses, and changing optical pathlengths. When the patient is not moving, absorption is substantially constant except for the flow of blood. The constant attenuation can be determined and subtracted from the signal via traditional filtering techniques. When the patient moves, this causes perturbation such as changing optical pathlength due to movement of background fluids (e.g., venous blood having a different saturation than the arterial blood). Therefore, the measured signal becomes erratic. Erratic motion induced noise typically cannot be predetermined and/or subtracted from the measured signal via traditional filtering techniques. Thus, determining the oxygen saturation of arterial blood and venous blood becomes more difficult.

Figure 3:
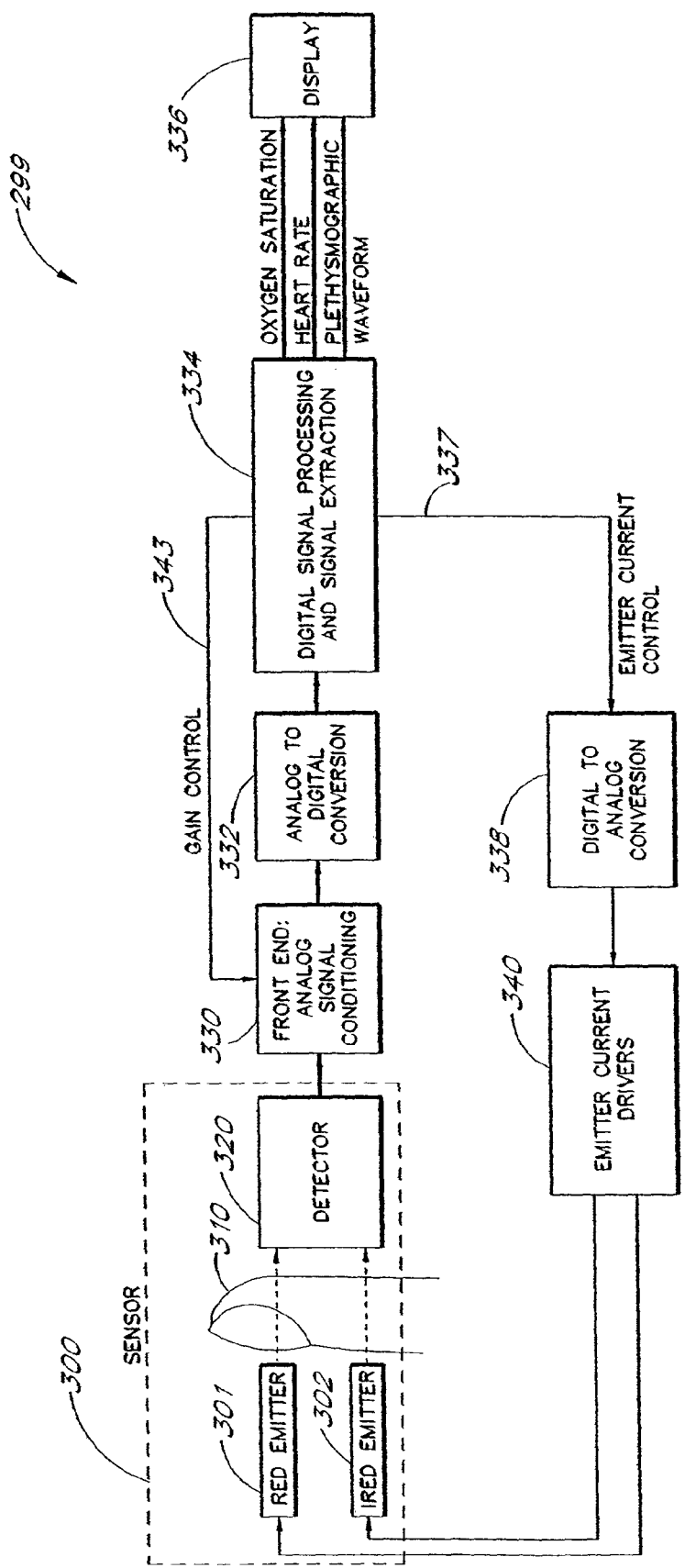
FIG. 3 illustrates a schematic diagram of a physiological monitor in accordance with the teachings of one aspect of the present invention

FIG. 3 depicts a general hardware block diagram of a pulse oximeter 299. A sensor 300 has two light emitters 301 and 302, such as LED's. One LED 301 emitting light of red wavelengths and another LED 302 emitting light of infrared wavelengths are placed adjacent a finger 310. A photodetector 320, which produces an electrical signal corresponding to the attenuated visible and infrared light energy signals is, located near the LED's 301 and 302. The photodetector 320 is connected to front end analog signal conditioning circuitry 330.

The front end analog signal conditioning circuit 330 has outputs coupled to an analog to digital conversion circuit 332. The analog to digital conversion circuit 332 has outputs coupled to a digital signal processing system 334. The digital signal processing system 334 provides the desired parameters as outputs for a display 336. Outputs for display are, for example, blood oxygen saturation, heart rate, and a clean plethysmographic waveform.

The signal processing system also provides an emitter current control output 337 to a digital-to-analog converter circuit 338 which provides control information for a set of light emitter drivers 340. The light emitter drivers 340 couple to the light emitters 301, 302. The digital signal processing system 334 also provides a gain control output 343 for the front end analog signal conditioning circuitry 330.

Figure 4:
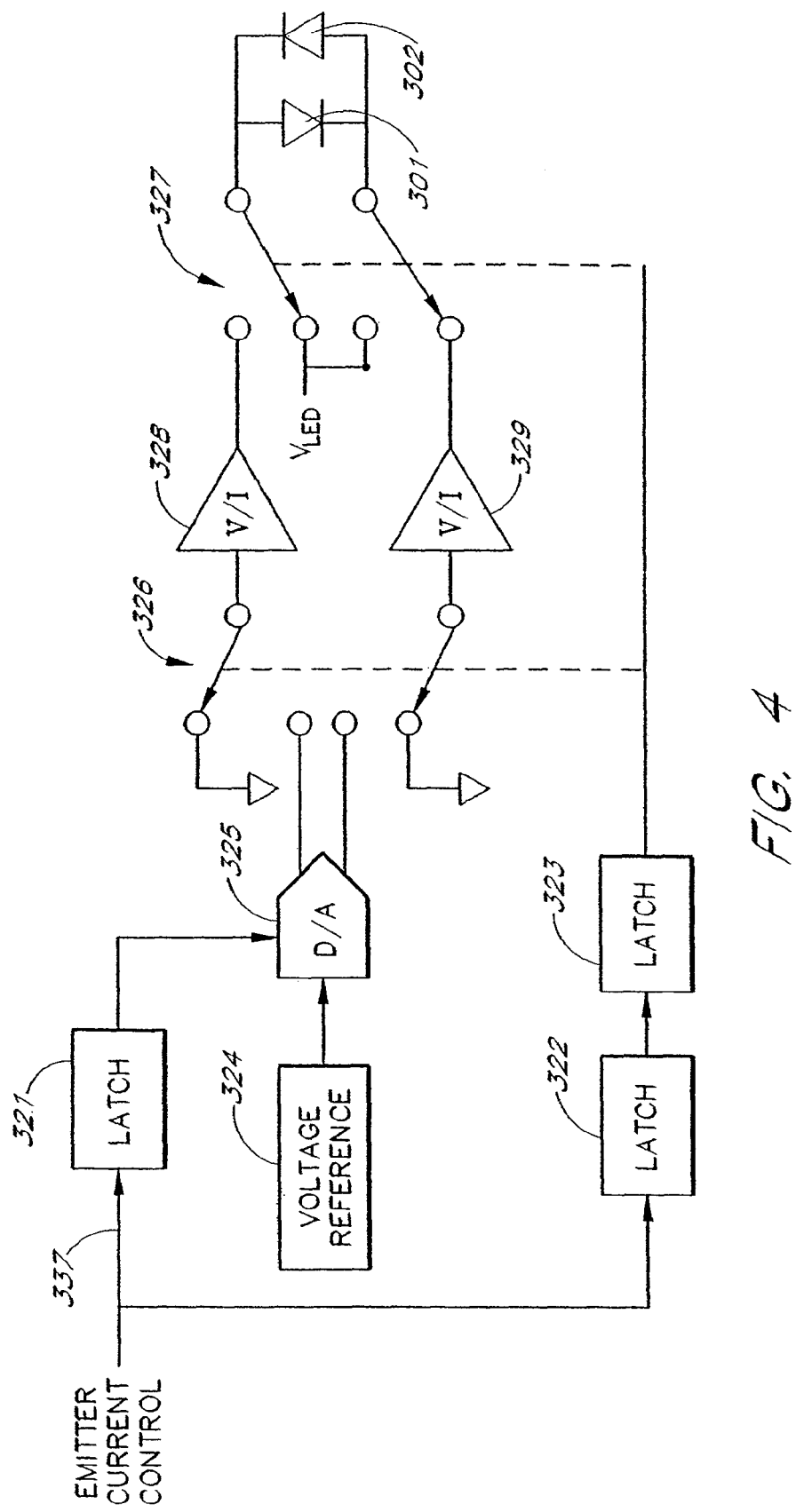
FIG. 4 illustrates an example of a low noise emitter current driver with accompanying digital to analog converter in accordance with the teachings of one aspect of the present invention.

FIG. 4 illustrates a preferred embodiment for the combination of the emitter drivers 340 and the digital to analog conversion circuit 338. As depicted in FIG. 4, the driver comprises first and second input latches 321, 322, a synchronizing latch 323, a voltage reference 324, a digital to analog conversion circuit 325, first and second switch banks 326, 327, first and second voltage to current converters 328, 329 and the LED emitters 301, 302 corresponding to the LED emitters 301, 302 of FIG. 3.

The preferred driver depicted in FIG. 4 is advantageous in that the present inventors recognized that much of the noise in the oximeter 299 of FIG. 3 is caused by the LED emitters 301, 302. Therefore, the emitter driver circuit of FIG. 4 is designed to minimize the noise from the emitters 301, 302. The first and second input latches 321, 322 are connected directly to the digital signal processor (DSP) bus 337. Therefore, these action of these latches significantly minimizes the bandwidth (resulting in noise) present on the DSP bus 337 which passes through to the driver circuitry of FIG. 4. The outputs of the first and second input latches 321, 322, only change when the latches detect their respective address on the DSP bus 337. The first input latch 321, receives the setting for the digital to analog converter circuit 325. The second input latch 322 receives switching control data for the switch banks 326, 327. The synchronizing latch 323 accepts the synchronizing pulses which maintain synchronization between the activation of emitters 301, 302 and the analog to digital conversion circuit 332.

The voltage reference 324 is also chosen as a low noise DC voltage reference for the digital to analog conversion circuit 325. In addition, in the present embodiment, the voltage reference 324 has a lowpass output filter with a very low corner frequency (e.g., 1 Hz in the present embodiment). The digital to analog converter 325 also has a lowpass filter at its output with a very low corner frequency (e.g., 1 Hz). The digital to analog converter 338 provides signals for each of the emitters 301, 302.

In the present embodiment, the output of the voltage to current converters 328, 329 are switched such that with the emitters 301, 302 connected in back-to-back configuration, only one emitter is active an any given time. In addition, the voltage to current converter 328 or 329 for the inactive emitter is switched off at its input as well, such that it is completely deactivated. This reduces noise from the switching and voltage to current conversion circuitry. In the present embodiment, low noise voltage to current converters are selected (e.g., Op 27 Op Amps), and the feedback loop is configured to have a low pass filter to reduce noise. In the present embodiment, the low pass filtering function of the voltage to current converters 328, 329 has a corner frequency of just above 316.7 Hz, which is the switching speed for the emitters, as further discussed below. Accordingly, the preferred driver circuit of FIG. 4, minimizes the noise of the emitters 301, 302.

In general, each of the red and infrared light emitters 301, 302 emits energy which is partially absorbed by the finger 310 and the remaining energy is received by the photodetector 320. The photodetector 320 produces an electrical signal which corresponds to the intensity of the light energy striking the photodetector 320. The front end analog signal conditioning circuitry 330 receives the intensity signals and filters and conditions these signals, as further described below, for further processing. The resultant signals are provided to the analog-to-digital conversion circuitry 332 which converts the analog signals to digital signals for further processing by the digital signal processing system 334. In the present embodiment, the output of the digital signal processing system 334 provides clean plethysmographic waveforms of the detected signals and provides values for oxygen saturation and pulse rate to the display 336.

It should be understood that in different embodiments of the present invention, one or more of the outputs may be provided. The digital signal processing system 334 also provides control for driving the light emitters 301, 302 with an emitter current control signal on the emitter current control output 337. This value is a digital value which is converted by the digital-to-analog conversion circuit 338 which provides a control signal to the emitter current drivers 340. The emitter current drivers 340 provide the appropriate current drives for the red emitter 301 and the infrared emitter 302. Further detail of the operation of the physiological monitor for pulse oximetry is explained below.

In the present embodiment, the light emitters 301, 302 are driven via the emitter current driver 340 to provide light transmission with digital modulation at 316.7 Hz. In the present embodiment, the light emitters 301, 302 are driven at a power level which provides an acceptable intensity for detection by the detector and for conditioning by the front end analog signal conditioning circuitry 330. Once this energy level is determined for a given patient by the digital signal processing system 334, the current level for the red and infrared emitters is maintained constant. It should be understood, however, that the current may be adjusted for changes in the ambient room light and other changes which would effect the voltage input to the front end analog signal conditioning circuitry 330. In the present invention, the red and infrared light emitters 301, 302 are modulated as follows: for one complete 316.7 Hz red cycle, the red emitter 301 is activated for the first quarter cycle, and off for the remaining three-quarters cycle; for one complete 316.7 Hz infrared cycle, the infrared light emitter 302 is activated for one quarter cycle and is off for the remaining threequarters cycle. In order to only receive one signal at a time, the emitters are cycled on and off alternatively, in sequence, with each only active for a quarter cycle per 316.7 Hz cycle and with a quarter cycle separating the active times.

The light signal is attenuated (amplitude modulated) by the pumping of blood through the finger 310 (or other sample medium). The attenuated (amplitude modulated) signal is detected by the photodetector 320 at the 316.7 Hz carrier frequency for the red and infrared light. Because only a single photodetector is used, the photodetector 320 receives both the red and infrared signals to form a time division multiplexed (TDM) signal. The TDM signal is provided to the front analog signal conditioning circuitry 330 and may be demodulated by either before or after analog to digital conversion.

Saturation Curves and Normalization

Figure 5:
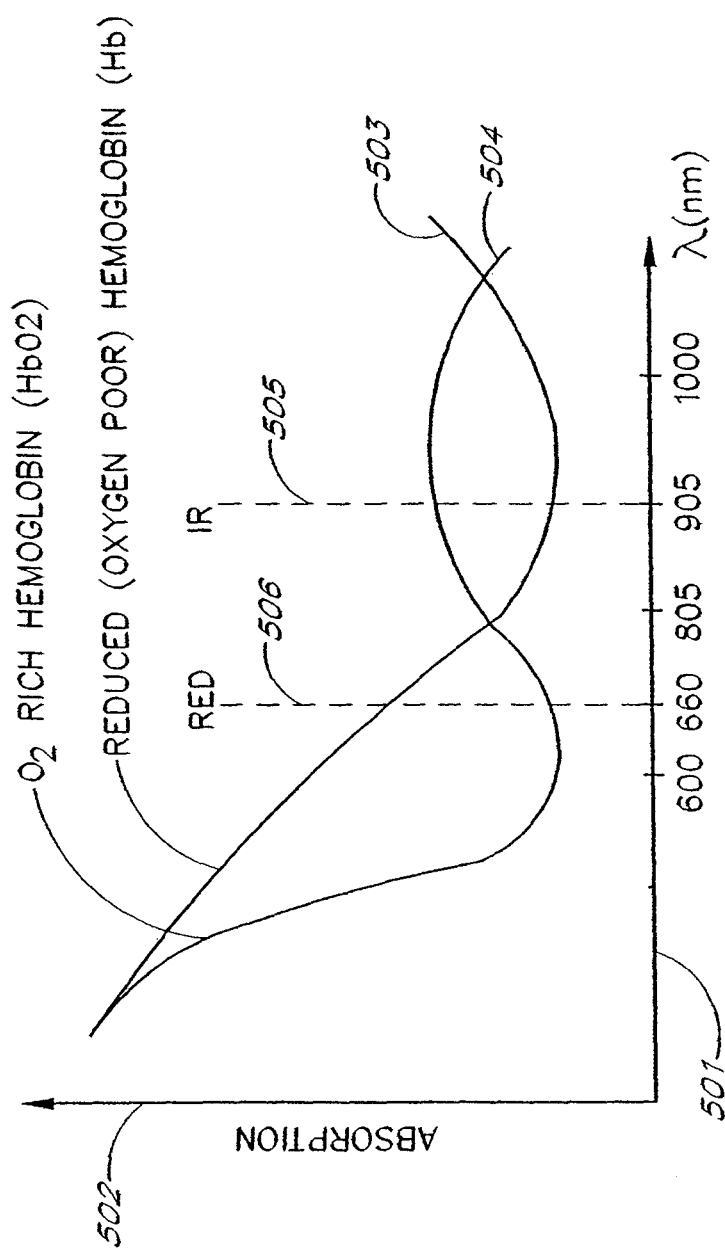
FIG. 5 illustrates the absorption properties of hemoglobin at various wavelength.

The ability of the apparatus 299 to measure the desired physiologic properties lies in the optical absorption properties of hemoglobin, as illustrated in FIG. 5. FIG. 5 shows an x axis 501 corresponding to a wavelength of light and a y axis 502 corresponding to an absorption coefficient for light passing through a medium. A reduced hemoglobin (Hb) curve 503 shows the absorption properties of oxygen poor hemoglobin. An oxygen rich hemoglobin (Hb02) curve 504 shows the absorption properties of oxygen rich hemoglobin. A reference line 506 highlights the region where the curves 503 and 504 pass through a value on the x axis 501 corresponding to 660 nm (nanometer) wavelength (the nominal operational wavelength of the red emitter 301). A reference line 505 highlights the region where the curves 503 and 504 pass through a value on the x axis 501 corresponding to 905 nm wavelength (the nominal operational wavelength of the infrared emitter 302).

At the reference line 506, the Hb curve 503 shows more absorption than the HbO2 curve 504. Conversely, at the reference line 505, the HbO2 curve shows more absorption than the Hb curve 503. The pulse oximeter can thus measure the blood oxygen saturation by measuring absorption of the blood at 660 nm and 905 nn, and the comparing the two absorption measurements.

According to the Beer-Lambert law of absorption, the intensity of light transmitted through an absorbing medium is given by:

$$I = I_0 e^{-\epsilon d c} \qquad (5)$$

where $I_0$ is the intensity of the incident light, $\epsilon$ is the absorption coefficient, c is the concentration coefficient and d is the thickness of the absorbing medium. In pulse oximetry applications, there are two sources, red and infrared, and thus two incident intensities, $I_{0,RD}$ for red, and $I_{0,IR}$ for infrared. Furthermore, in blood there are two concentrations of interest, namely the concentration of oxygen poor hemoglobin, denoted by $C_{Hb}$ and the concentration of oxygen rich hemoglobin, denoted by $C_{HbO2}$. The combination of the two optical wavelengths and the two concentrations means that there are four absorption coefficients, namely $\epsilon_{RD,Hb}$, $\epsilon_{RD,HbO2}$, $\epsilon_{IR,Hb}$, and $\epsilon_{IR,HbO2}$. Using these quantities, and assuming no time variation in any of the values except d, gives two separate Beer-Lambert equations for the pulse oximeter.

$$I_{RD} = I_{0,RD} e^{-[\epsilon_{RD,Hb} C_{Hb} + \epsilon_{RD,HbO2} C_{HbO2}] d(t)} \qquad (6)$$

$$I_{IR} = I_{0,IR} e^{-[\epsilon_{IR,Hb} C_{Hb} + \epsilon_{IR,HbO2} C_{HbO2}] d(t)} \qquad (7)$$

The measurement apparatus 299 does not provide a capability for measuring the incident terms and $I_{0,RD}$ and $I_{0,IR}$ appearing in the above equation, and thus, strictly speaking, the value of $I_{RD}$ and $I_{IR}$ cannot be determined. However, in the pulse oximeter, only differential measurements are necessary. In other words, it is only the time varying nature of the values $I_{RD}$ and $I_{IR}$ and the relationship between the values that are important. The time variation in d(t) occurs primarily because blood flows in and out of the finger with each heartbeat. As blood flows into the finger, the effective value of d, as well as the scattering component, increases, and as blood flows out, the effective value of d and the scattering decreases. There are also time variations in the concentrations $C_{Hb}$ and $C_{HbO2}$ as the blood oxygen saturation level changes. Fortunately, these variations are slow compared to the variations in d(t), and they can be ignored.

Figure 6:
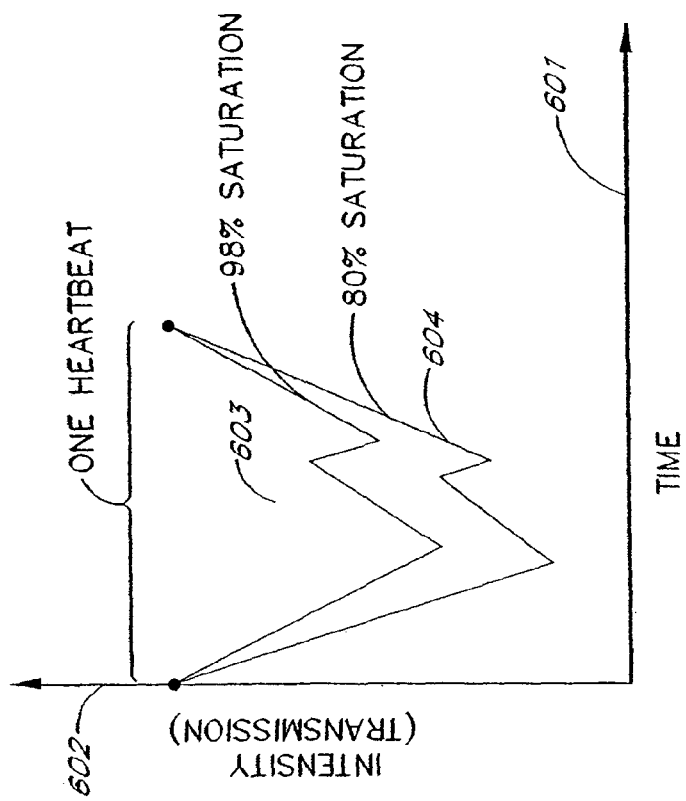
FIG. 6 illustrates one cycle of an idealized plethysmographic waveform for various levels of oxygen saturation at a fixed perfusion.

FIG. 6 illustrates one cycle of an idealized plethysmographic waveform for various levels of oxygen saturation. The figure shows an x-y plot having a time axis 601 in the x direction, and a transmission axis 602 in the y direction. The transmission axis 602 shows the intensity of the red light transmitted through the finger. A curve 604 shows the transmission of red light for 80% blood oxygen saturation. A curve 603 shows transmission of red light for 98% blood oxygen saturation. The curves 603 and 604 are intended to show different values of saturation given the same perfusion d. As shown in the figure, at the beginning of a heartbeat, red transmission is at a maximum because the finger contains relatively little blood. As the heartbeat progresses, blood is perfused into the finger and the amount of light transmission diminishes. Transmission diminishes because the additional material, the blood, increases the effective path length d in Equation (6). Transmission also diminishes somewhat because of scattering produced by the blood. If the blood is highly saturated with oxygen, as shown in the curve 603, the transmission diminishes only slightly because, as shown in FIG. 5, HbO2 has a relatively small absorption coefficient in the red wavelengths. If the blood has low oxygen saturation, as shown in the curve 604, then transmission diminishes significantly more because, as shown in FIG. 5, Hb has a relatively large absorption in the red wavelengths.

If FIG. 6 were redrawn to show the transmission properties of infrared light, then the curves 603 and 604 would essentially be interchanged, because as shown in FIG. 5, more infrared light is absorbed by HbO2 than is absorbed by Hb.

Figure 7:
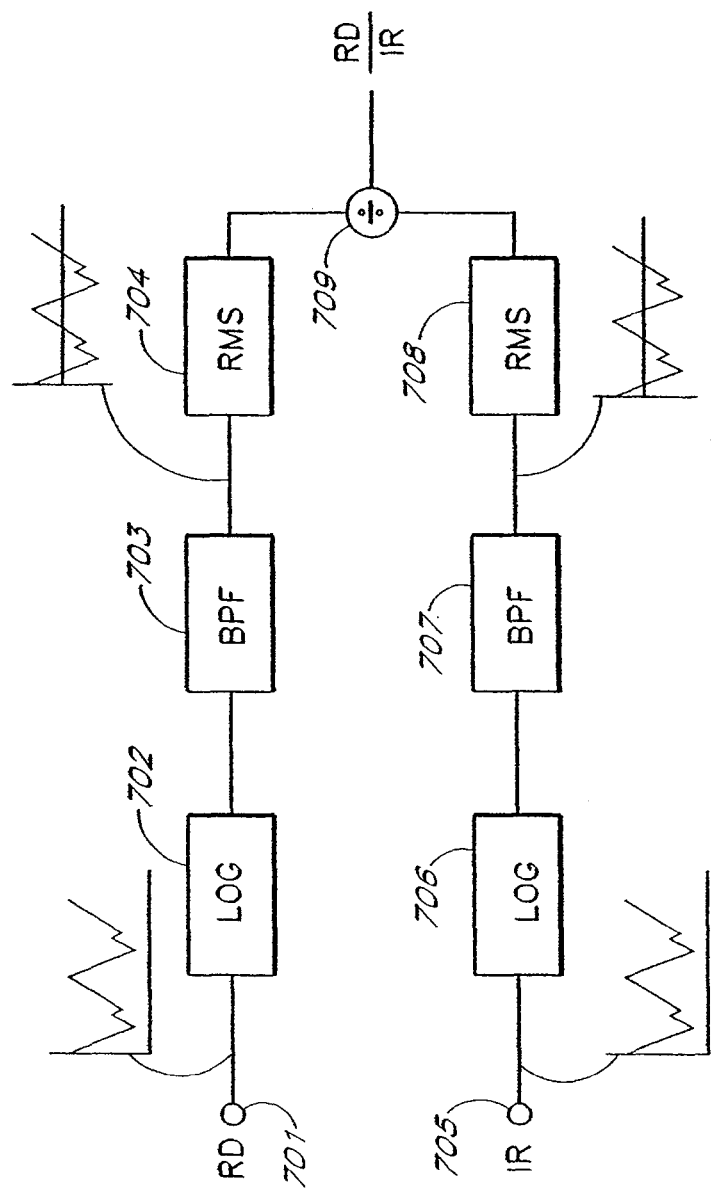
FIG. 7 illustrates a block diagram of the signal processing used to compute the ratio of red signal to infrared signal in accordance with one aspect of the present invention.

The above properties of the absorption of light by Hb and HbO2 advantageously provide a way to measure blood oxygen saturation by computing the ratio of red light to infrared light. FIG. 7 shows one embodiment of a signal processing apparatus for obtaining the desired ratio. FIG. 7 shows a red signal path which begins at a RD signal input 701. The RD signal input 701 corresponds to the amount of red light transmitted through the finger. The signal at the RD signal input 701 is fed into a logarithmic amplifier 702 which in turn feeds a bandpass filter 703. The output of the bandpass filter 703 is fed into a root-means-square (RMS) detector 704. The output of the RMS detector 704 is fed to a numerator input of a divider 709. FIG. 7 further shows an IR signal path comprising an IR input 705, a logarithmic amplifier 706, a bandpass filter 707, and an RMS detector 708. The output of the RMS detector 708 is fed to a denominator input of the divider 709.

In a preferred embodiment, the elements shown in FIG. 7 are part of the signal processing block 334 shown in FIG. 3. The RD input 701 and IR input 705 are obtained by demultiplexing the output of the detector 320, also shown in FIG. 3. The signals at the inputs 701 and 705 correspond to $I_{RD}$ and $I_{IR}$ respectively, and are similar to the curves shown in FIG. 6. However, in the preferred embodiment, the signals are uncalibrated (i.e., the scale of the y axis 602 is unknown) because the value of $I_{0,RD}$ and $I_{0,IR}$ in Equations (6) and (7) are unknown. This is not an impediment to the measurement of the blood oxygen saturation, because saturation can be obtained without reference to either $I_{0,RD}$ or $I_{0,IR}$ as follows. Taking the natural logarithm (in signal processing blocks 702 and 706) of both Equation (6) and Equation (7) yields:

$$\ln(I_{RD}) = \ln(I_{0,RD}) - [\epsilon_{RD,Hb} C_{Hb} + \epsilon_{RD,HbO2} C_{HbO2}] d(t) \quad (8)$$

$$\ln(I_{IR}) = \ln(I_{0,IR}) - [\epsilon_{IR,Hb} C_{Hb} + \epsilon_{IR,HbO2} C_{HbO2}] d(t) \quad (9)$$

Applying a bandpass filter (in signal processing blocks 703 and 707) removes the non-time varying components, and allows Equations (8) and (9) to be rewritten as:

$$RD(t) = -[\epsilon_{RD,Hb} C_{Hb} + \epsilon_{RD,HbO2} C_{HbO2}] d(t) \quad (10)$$

$$IR(t) = -[\epsilon_{IR,Hb} C_{Hb} + \epsilon_{IR,HbO2} C_{HbO2}] d(t) \quad (11)$$

Figure 8:
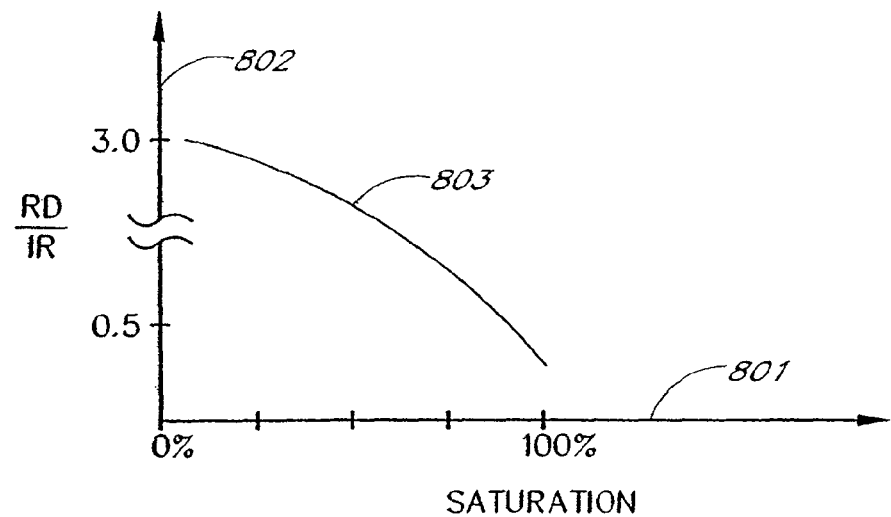
FIG. 8 is a graph which illustrates the relationship between the red/infrared ratio and blood oxygen saturation.
Figure 9:
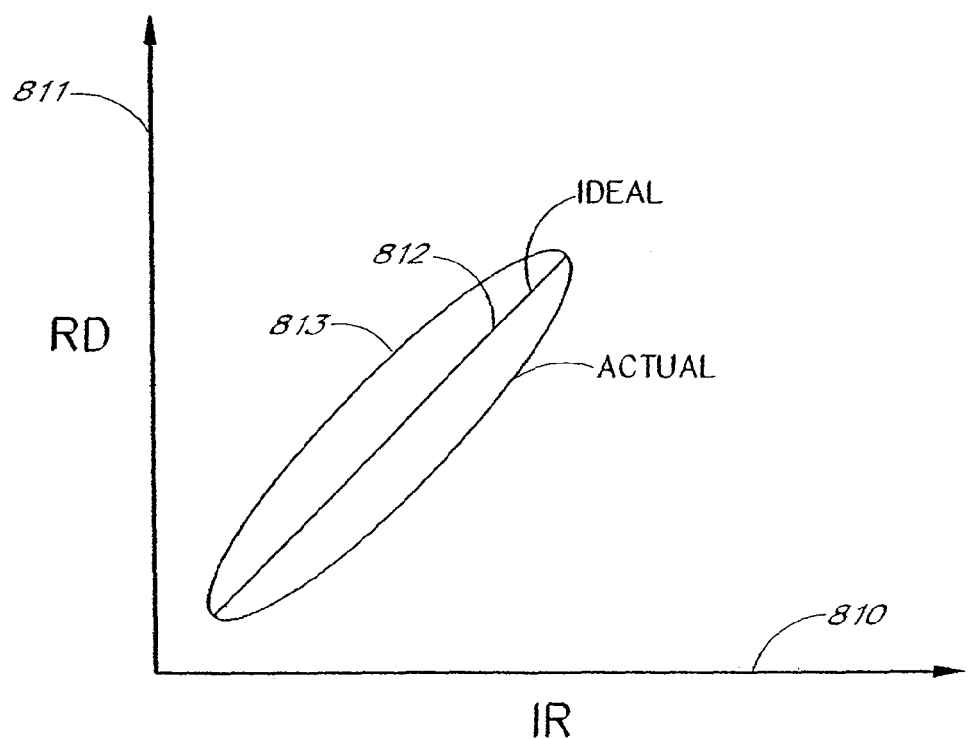
FIG. 9 is a graph which illustrates the relationship between the ideal red and infrared signals, and the relationship between measured red and infrared signals.

FIG. 9 shows a plot of RD(t) versus IR(t). In FIG. 9, an x axis 810 corresponds to IR(t) and a y axis 811 corresponds to RD(t). A straight line 812, having a positive slope, illustrates how the plot of RD(t) versus IR(t) would appear under ideal conditions of no noise, no scattering, and no motion artifacts. A curve 813 depicts a more realistic locus of points RD(t) versus IR(t) under normal measurement conditions. FIG. 8 shows a plot of blood oxygen saturation versus the ratio of the RMS value of RD(t)/IR(t). FIG. 8 shows an x axis 801 corresponding to blood oxygen saturation from 0% to 100% and a y axis corresponding to RMS(RD(t))/RMS(IR(t)) ranging from 0 to 3. A saturation curve 803 depicts the relationship between RMS(RD(t))/RMS(IR(t)) and blood oxygen saturation. The blood oxygen saturation is given by sat=100*$C_{HbO2}/(C_{Hb}+C_{HbO2})$. It is obtained by dividing Equation (10) by Equation (11) and solving for $C_{HbO2}$ and $C_{Hb}$ using the measured values of RD(t) and IR(t), and the known values of the absorption coefficients. Note that the unknown quantity d(t) is approximately the same for both red and infrared and thus divides out.

Detection and Removal of Motion Artifacts

Figure 10:
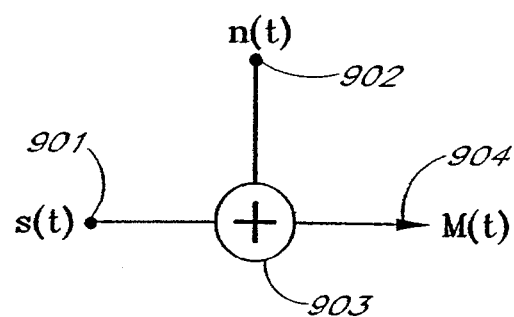
FIG. 10 illustrates a model for measured data in a pulse oximeter.

Persons skilled in the art know that the data obtained during pulse oximetry measurements using red and infrared light are often contaminated due to motion. Identification and removal of these motion artifacts is often a prerequisite to any signal processing used to obtain blood oxygen saturation, pulserate, or other physiological data. FIG. 10 schematically illustrates an additive noise process model that can be used, in conjunction with Equation (10) and Equation (11) to approximate the measured data contaminated by such motion artifacts. FIG. 9 shows a desired signal input s(t) 901 and an undesired signal input n(t) 902. The desired signal s(t) 901 and the undesired signal input n(t) 902 are summed by a summing junction 903. The output of the summing junction 903 represents the actual measured data M(t) 904. As applied to Equation (10), the desired signal s(t) 901 corresponds to RD(t). As applied to Equation (11), the desired signal s(t) 901 represents IR(t).

In FIG. 10, the desired signal s(t) 901, which contains the desired physiologic data is not directly accessible. Only the measured signal M(t) 904 is accessible. Thus, the problem is to obtain an estimate of the undesired signal n(t) 902 so that it can be subtracted from the measured signal to yield the desired signal. One such method for removing the undesired signal n(t) involves the use of a correlation canceler as is found in U.S. Pat. No. 5,432,036 (the '036 patent) assigned to the same assignee as the present application.

The correlation canceler is a complex operation requiring significant computational overhead. In accordance with one embodiment of the present invention, a new and novel method for detecting the presence of motion artifacts and removing these artifacts can be found in the spectral domain representations of the signals RD(t) and IR(t). Use of the spectral domain representations is more compatible with many of the digital signal processor (DSP) devices currently available. Further, the use of the spectral domain representations provides a method, as disclosed below, a way to estimate the amount of motion and noise separately. As a further advantage, it is noted that, under certain circumstances, the correlation canceler would drive the output signal to zero. The spectral domain method of detecting artifacts is far less likely to drive the output signal to zero.

Figure 11:
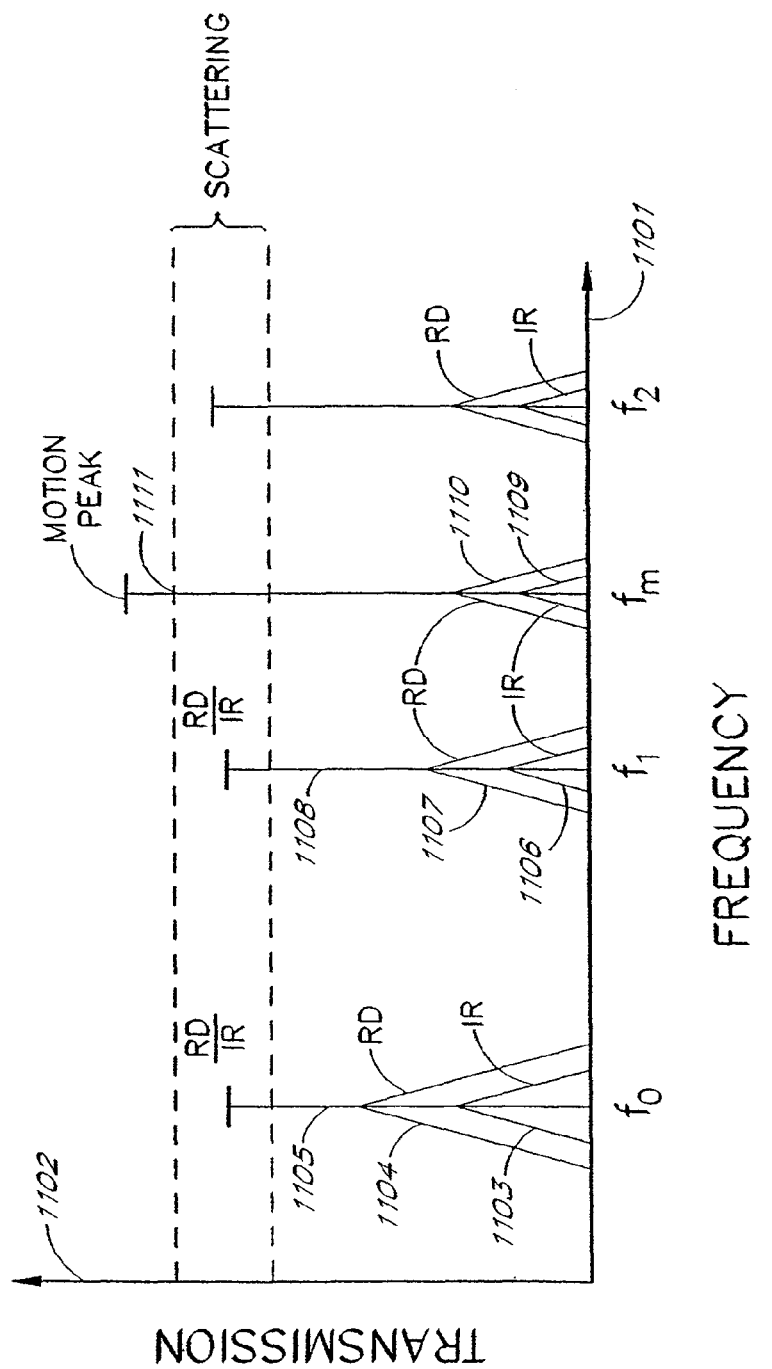
FIG. 11 is an idealized frequency domain plot of the red and infrared transmission signals

FIG. 11 shows an idealized illustration of the spectrum of RD(t) and IR(t). FIG. 11 shows an x axis 1101 corresponding to frequency, and a y axis 1102 corresponding to the magnitude of the spectral components. The spectrum of RD(t), denoted mathematically as:

$$RD(\omega) = \mathcal{F}[RD(t)] \quad (12)$$

is shown as a series of peaks, comprising a first spectral peak 1104 at a fundamental frequency $f_0$, a second spectral peak 1107 at a first harmonic $f_1$ and a third spectral peak 1110 at a frequency $f_m$. The spectrum of IR(t), denoted mathematically as:

$$IR(\omega) = \mathcal{F}[IR(t)] \quad (13)$$

is shown as a series of peaks, comprising a first spectral peak 1103 at the fundamental frequency $f_0$, a second spectral peak 1106 at the first harmonic $f_1$ and a third spectral peak 1109 at a frequency $f_m$. The ratio of the spectral components, given by $RD(\omega)/IR(\omega)$, is shown as a first ratio line 1105 at the fundamental frequency $f_0$, a second ratio line 1108 at the first harmonic $f_1$ and a third ratio line 1111 at the frequency $f_m$. As discussed below, when there are no motion artifacts in the spectrum of FIG. 11, all of the spectral peaks will occur at harmonic frequencies, and all of the ratio lines will have approximately the same height. Under conditions of no motion, difference in the height of the ratio lines will be due primarily to scattering effects. The spectral peaks 1110 and 1109 corresponding to the frequency $f_m$, which is not necessarily a harmonic of $f_0$, represent peaks due to motion, and therefor having an amplitude different from that of the first spectral line 1105 and the second spectral line 1108.

One skilled in the art will recognize that the representations in FIG. 11 have been idealized for the purposes of explanation. In particular, in actual measured data, especially data contaminated by noise and other undesired components, the frequencies of the spectral peaks of $RD(\omega)$ do not correspond exactly to the spectral peaks of $IR(\omega)$. Although corresponding frequencies will typically be quite close, variations of a few percent are not unexpected. Thus, for example, it will be obvious to one skilled in the art that, due to the imperfections in most measured data, the fundamental frequency $f_0$ found for $RD(\omega)$ will often be different from the fundamental frequency $f_0$ found for $IR(\omega)$. The same comments would apply to other harmonics (e.g., $f_1$ and $f_2$) as well. In one embodiment of the present invention, the frequencies $f_0$, $f_1$, $f_2$ (or equivalently $\omega_0$, $\omega_1$, $\omega_2$), etc. (hereinafter the frequency peaks) correspond to the frequency peaks found in $RD(\omega)$, and the ratios $RD(\omega)/IR(\omega)$ are calculated using values of $RD(\omega)$ and $IR(\omega)$ at those frequencies, regardless of whether they also happen to correspond to a frequency peak in $IR(\omega)$. In another embodiment of the present invention, the frequency peaks correspond the frequency peaks found in $IR(\omega)$, and the ratios $RD(\omega)/IR(\omega)$ are calculated using the values of $RD(\omega)$ and $IR(\omega)$ at those frequencies, regardless of whether they also happen to correspond to a frequency peak in $RD(\omega)$. In yet another embodiment of the present invention, the frequency peaks of $RD(\omega)$ and $IR(\omega)$ are found separately, and the ratios $RD(\omega)/IR(\omega)$ are calculated by matching the frequency peaks of $RD(\omega)$ with the nearest frequency peaks of $IR(\omega)$.

In an ideal measurement, the red and infrared spectra are the same to within a constant scale factor. Thus, in an ideal measurement, all of the ratio lines 1105, 1108 and 1111 have substantially the same amplitude. Any differences in the amplitude of these lines is likely due to motion or other contaminations represented by n(t) (including scattering effects). For each component, red and infrared, the model of FIG. 9 can be expressed as:

$$S_1(t) = A(t) + N(t) \tag{14}$$

$$S_2(t) = rA(t)h(t) + \mu N(t)\eta(t)$$
$$\approx rA(t) + \mu N(t)$$

where $S_1(t)$ represents the infrared signal, $A(t)$ represents the desired infrared signal and $N(t)$ represents the noise signal. Likewise, $S_2(t)$ represents the measured red signal, r represents the ratio of red to infrared ($RD(\omega)/IR(\omega)$) expected in an uncontaminated measurement, and $\mu$ represents the ratio of red noise to infrared noise. The quantities h(t) and f(t) are primarily due to scattering, and thus required because, strictly speaking, A(t) and N(t) in the red channel and infrared channels are not simply related by a constant. However, for most purposes, the quantities h(t) and η(t) are sufficiently close to unity that they can be ignored.

Introducing an arbitrary scaling factor a into the equation for $S_1$, and then subtracting the two equations yield (for notational convenience, the time dependence of S, A and N will not be explicitly shown):

$$\alpha S_1 - S_2 = A(\alpha-r) + N(\alpha-\mu) \tag{15}$$

Two special cases arise from Equation (17). First, when Equation (17) reduces to:

$$N = \frac{\alpha S_1 - S_2}{r - \mu} \tag{16}$$

Second, when a=μ, Equation (17) reduces to:

$$A = \frac{\alpha S_1 - S_2}{\mu - r} \tag{17}$$

The values of μ and r can be found from the ratio of $RD(\omega)/IR(\omega)$ as shown in FIG. 11 and the following two observations. First, since r is the coupling coefficient between red and infrared (the ratio of red to infrared) then r is expected to be reasonably constant over short periods of time. Likewise, μ is expected to be relatively constant because it is merely the coupling coefficient between the noise in the red and infrared signals. Second, the condition μ=r is not expected to occur because that would mean that the saturation due to arterial blood is equal in magnitude to the saturation due to venous blood. One skilled in the art will recognize, that, except for short periods of time, arterial blood saturation and venous blood saturation cannot be the same, because a living body consumes oxygen from the blood as the blood passes from the arteries to the veins. Arterial blood and venous blood saturation can be the same for short periods of time, and even reversed, especially where blood pooling has occurred and a quick desaturation is taking place. It is always expected that μ is larger than r. Therefore, in one embodiment of the present invention, the value of μ corresponds to the largest peak in FIG. 11 and the value of r corresponds to the smallest peak of FIG. 11. Further, the presence of motion artifacts in the data are easily detectable by examination of the relationship between μ and r.

In a preferred embodiment, the value of μ is found by classifying the ratio peaks according to a ratio threshold g. The ratio threshold g is computed identifying the first N ratio lines $R_N$ associated with the first N spectral peaks. The ratio threshold g is then computed as a modified center of mass for the $R_N$ lines according to the following equation.

$$g = \frac{N}{\sum_{i=0}^{N-1} \frac{1}{R_i}}$$

Each ratio line is then compared with the ratio threshold g. Only those ratio lines whose magnitude is larger than the ratio threshold g are included in a set Y of ratio lines. Only ratio lines in the set Y are used in the calculation of μ. In one embodiment, the value of µ is the magnitude of the largest ratio peak in the set of ratio peaks $R_i$ for i=0 . . . N. In an alternate embodiment, the value of µ is the magnitude of the ratio peak corresponding to the largest spectral peak in the set Y.

The values of µ and r are used to determine whether motion artifacts are present. In one embodiment, the ratio µ/r is calculated. If the ratio is close to unity, then, to within a constant scaling factor, the spectrum RD(ω) is approximately the same as the spectrum IR(ω) and thus there are no motion artifacts. If, on the other hand, the ratio µ/r is not close to unity, then the shape of the spectrum RD(ω) is different from the spectrum IR(ω), signaling the presence of motion artifacts, and thus the spectrum must be scrubbed according to Equation (17).

In a preferred embodiment, a delta is computed by subtracting the magnitude of the smallest ratio line from the magnitude of the largest ratio line. If the delta is smaller than a threshold value, then the spectrum RD(ω) is approximately the same as the spectrum IR(ω) and thus there are no motion artifacts, but only variations due to scattering. If, on the other hand, the delta µ–r is greater than the threshold value, then the shape of the spectrum RD(ω) is different from the spectrum IR(ω), signaling the presence of motion artifacts, and thus the spectrum must be scrubbed according to Equation (19).

Figure 12:
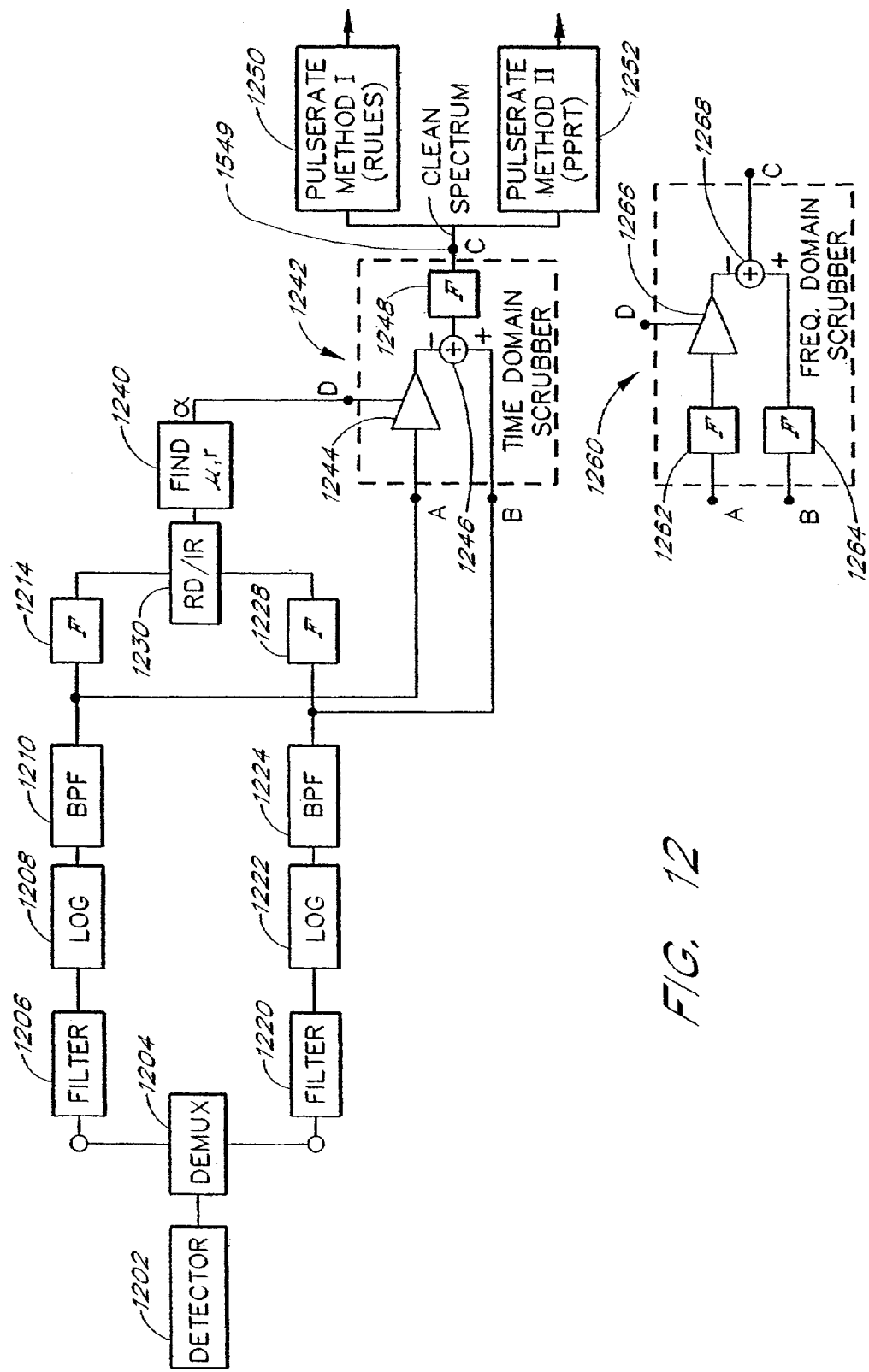
FIG. 12 is a block diagram of a motion detector and removal system in accordance with one aspect of the present invention.

FIG. 12 shows a block diagram of a signal processing system that implements the motion detection and spectrum scrubbing operations in accordance with one aspect of the present invention. In FIG. 12, an input from a single sensor 1202 that receives red and infrared light is fed into a demultiplexer 1204 which separates the red and infrared signals. The red signal is fed into a filter 1206 which removes unwanted spectral components. The output of the filter 1206 is normalized (as is described in the text describing FIG. 7) by the series combination of a log amplifier 1208, and a bandpass filter 1210. The output RD(t) of the bandpass filter 1210 is fed into a Fourier transform block 1214. The output of the transform block 1214 is fed into the numerator term of a divider 1230. The infrared output from the demultiplexer 1204 is processed, in the same fashion as the red signal, by the series combination of a filter 1220, a log amplifier 1222, a bandpass filter 1224, and a Fourier transform block 1228. The output of the Fourier transform block 1228 is fed into a denominator input of the divider 1230. An output of the divider 1230 is fed into a process block 1240 which determines µ, and r, and which computes a according to the flowchart of FIG. 13. An a output of the process block 1240 is fed as an input to a time domain waveform scrubber 1242. The time domain waveform scrubber 1242 has three input terminals, A, B, and D, and a single output terminal C. The time domain scrubber terminal A is connected to the output of the bandpass filter 1210. The time domain scrubber terminal B is connected to the output of the bandpass filter 1224. The time domain scrubber terminal D is connected to the a output of the process block 1240. Inside the time domain scrubber 1242, the terminal A is connected to a signal input of a gain controlled amplifier 1244. A gain control input of the amplifier 1244 is connected to the scrubber terminal D. The scrubber terminal B is connected to a plus input of an adder 1246. An output of the amplifier 1244 is connected to a minus input of the adder 1246. An output of the adder 1246 is connected to a Fourier transform block 1248. An output of the Fourier transform block 1248 is connected to the scrubber output terminal C.

One skilled in the art will recognize that the linearity of the Fourier transform allows the scrubbing operation to be carried out in the frequency domain as well. A frequency domain scrubber 1240 is also shown in FIG. 12. The frequency domain scrubber 1260 has the same four terminals, A, B, C, and D, as the time domain scrubber 1242.

Inside the frequency domain scrubber 1260, the terminal A is connected to a signal input of a Fourier transform block 1262. The output of the Fourier transform block 1262 is connected to a signal input of a gain controlled amplifier 1266. A gain control input of the amplifier 1266 is connected to the scrubber terminal D. The scrubber terminal B is connected to a Fourier transform block 1264. An output of the transform block 1264 is connected to a plus input of an adder 1268. An output of the amplifier 1266 is connected to a minus input of the adder 1268. An output of the adder 1268 is connected to the scrubber output terminal C.

Regardless of whether the time domain scrubber 1242 or the frequency domain scrubber 1260 is used, the scrubber output C is a plethysmographic waveform in the frequency domain at a terminal 1249. Ideally, the waveform at terminal 1249 is cleaner (e.g., has a better signal to noise ratio) than the waveform at either scrubber input A or scrubber input B. The waveform at terminal 1249 can be displayed on a display (not shown) or sent to a rule based pulserate detector 1250 and/or a transform based pulserate detector 1252.

Figure 13:
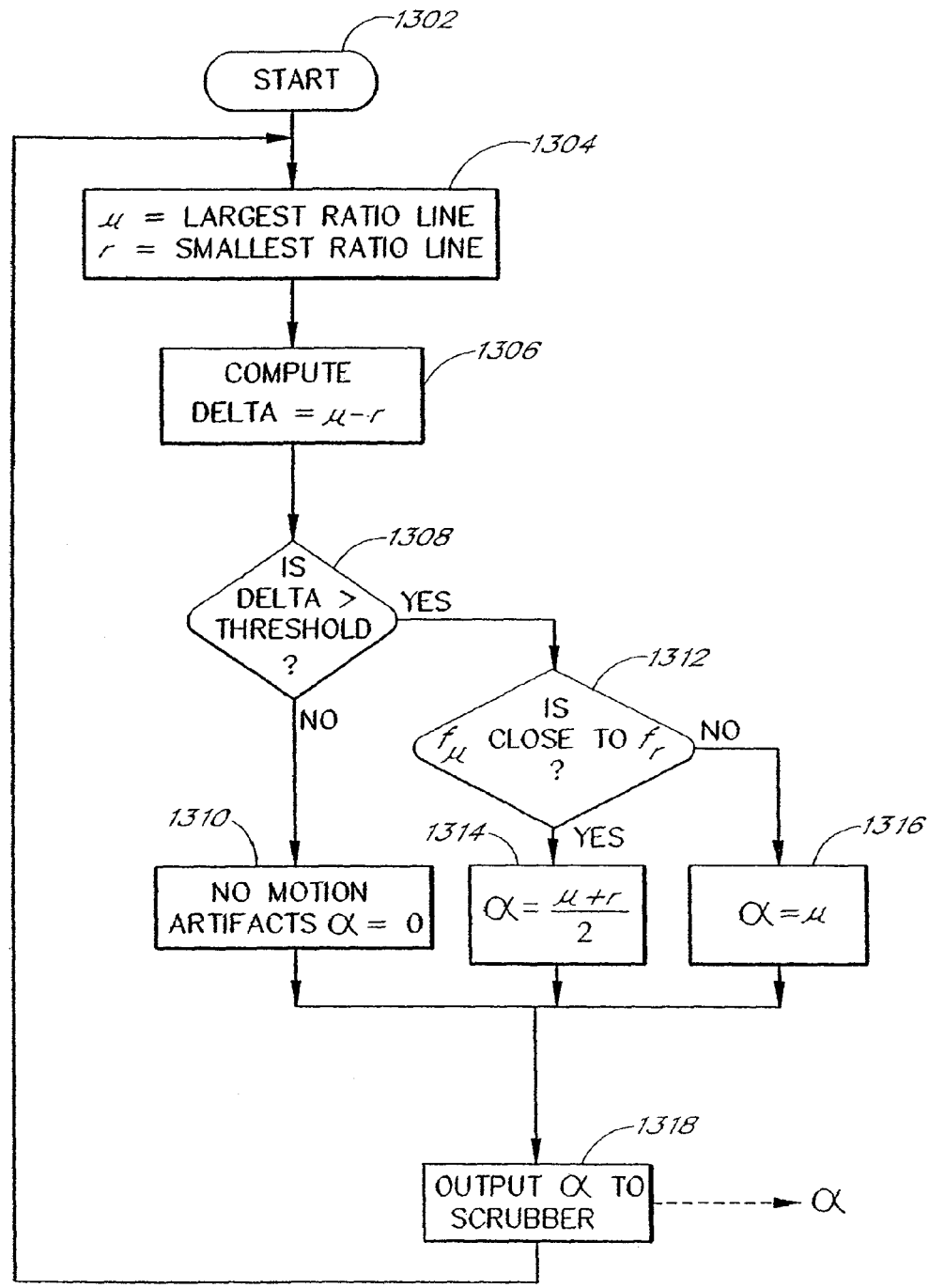
FIG. 13 is a flowchart showing the processing steps of a motion detector and removal method in accordance with one aspect of the present invention.

FIG. 13 is a flowchart which illustrates the process steps performed by the signal processing block 1240 in FIG. 12. The flowchart of FIG. 13 begins at a start block 1302 and proceeds to a process block 1304. In the process block 1304, the spectrum $F(\omega)=RD(\omega)/IR(\omega)$ is searched for the largest ratio line µ and smallest ratio line r and the frequencies $f_\mu$ and $f_r$ at which those two lines occur. The process then advances to a process block 1306 where the difference, delta d=µ–r is computed. The process then proceeds to a decision block 1308. If, in the decision block 1308, the delta d is greater than a threshold value, then motion artifacts are present and the process advances to a decision block 1312 to continue the calculation of α. Otherwise, if in the process block 1308, the delta d is less than the threshold value, then no scrubbing ins necessary and the process advances to a process block 1310. Since both µ and r are ratios, they are dimensionless. The delta d is also dimensionless. In a preferred embodiment, the threshold value is 0.5. In the process block 1310, the value of α is set to 0, which essentially disables the scrubber. In the decision block 1312, the frequencies $f_\mu$ and $f_r$ are compared. If the two frequencies are close together, then the process advances to a process block 1314; otherwise, the process advances to a process block 1316. In the process block 1314 the value of a is set to α=(µ+r)/2. In the process block 1316 the value of α is set to a=µ. The process blocks 1310, 1314 and 1316 all advance to a process block 1318 where the value of α is sent to the scrubber. Upon completion of the process block 1318, the process jumps back to the process block 1304 to recalculate α.

One skilled in the art will recognize that the flowchart in FIG. 13 can be modified to perform additional functions. For example, upon detecting that motion artifacts are present (during the transition to the decision block 1312), an indicator can be lit, or an alarm can be sent, to warn the medical clinician that motion artifacts were present. In yet another embodiment, upon transitioning to the process block 1312, the delta d could be examined against a second threshold to determine whether the motion artifacts were so severe that further processing was impossible.

Rule Based Pulserate Detection

In addition to measuring blood oxygen saturation, a pulse oximeter is able to perform continuous monitoring of a patient's pulserate. As shown in FIG. 6, each heartbeat forces blood into the arteries and that increase in blood is detected by the plethysmographic apparatus. Thus, the scrubbed spectrum present at the terminal 1250 in FIG. 12 contains some of the information that would be found in the Fourier spectrum of an electrocardiograph (EKG).

Figure 14A:
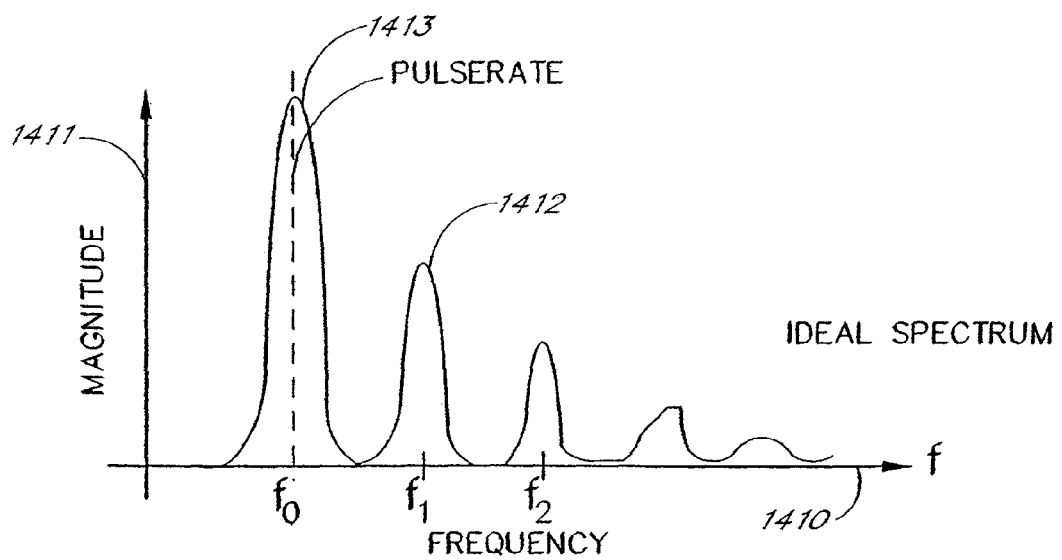
FIG. 14A is an idealized frequency domain plot of an plethysmographic wave.

FIG. 14A shows an ideal spectrum F(ω) of a clean plethysmographic wave from a heart that is beating with a very regular beat. The figure shows an x axis 1410 corresponding to frequency and a y axis 1411 corresponding to the magnitude of the spectral components. A curve 1412 shows |F(ω)|. It is well known, that the waveform of a human heartbeat is not a pure sine wave, and thus the curve 1412 is not a single spectral line, but rather a first spectral line at a fundamental frequency $f_0$ and a series of decreasing harmonics at $2f_0, 3f_0$, etc. Clearly, under these conditions, the frequency $f_0$ corresponds to the pulserate.

Figure 14B:
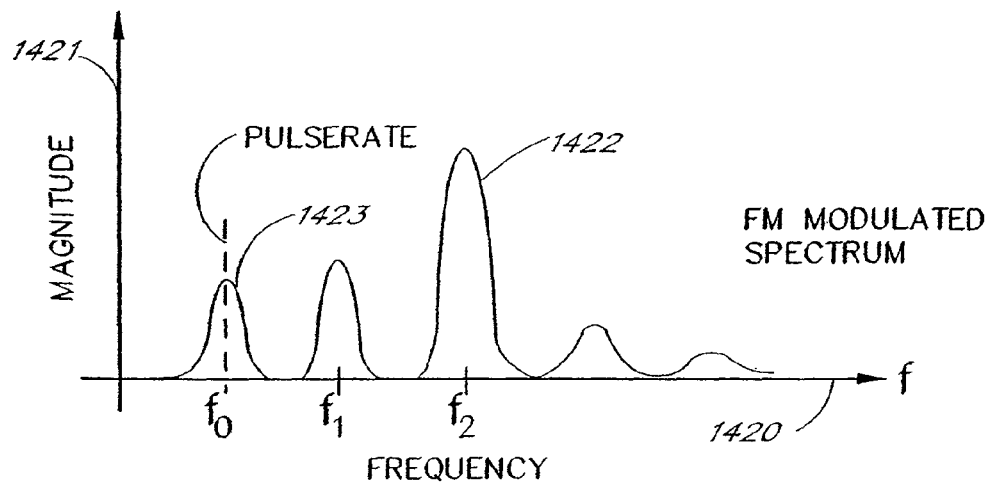
FIG. 14B is an idealized frequency domain plot of a plethysmographic wave showing the effect of FM modulation.

Often the ideal waveform of FIG. 14A is not seen because the heart is beating irregularly or because the cardio-vascular system of the subject is producing a large dicrotic notch. This leads to a spectrum in which the largest spectral line is not necessarily the pulserate. FIG. 14B shows one example of such a waveform. Like FIG. 14A, FIG. 14B shows an x axis 1420 corresponding to frequency, and a y axis 1421 corresponding to amplitude. A curve 1422 shows F(ω). However, unlike the curve 1412, the curve 1422 shows a spectral line at a fundamental frequency $f_0$, and a series of harmonics $f_1$ and $f_2$ having amplitudes larger than the amplitude of the fundamental, with $f_2$ being the largest. The curve 1422 illustrates the folly of attempting to determining pulserate merely by finding the largest spectral line. Such an algorithm, applied to the curve 1422 would report a pulserate that was three times higher than the actual pulse rate.

Figure 14C:
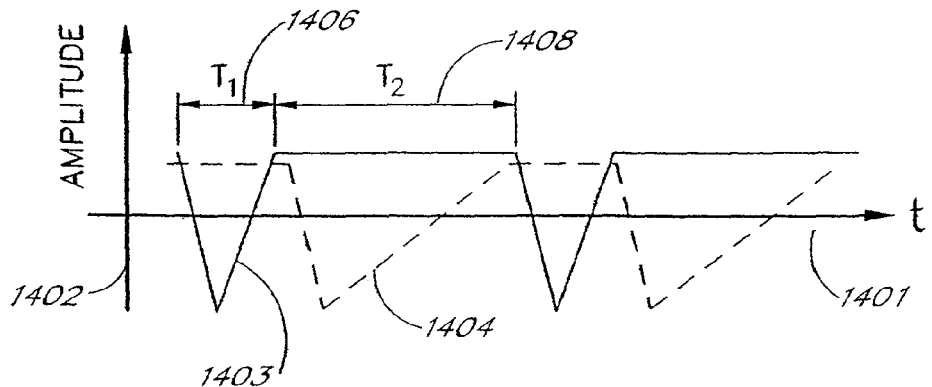
FIG. 14C is an idealized time domain plot of a superimposed pair of plethysmographic waves that can be used to model an FM modulated plethysmographic wave.

The spectrum shown in curve 1422 is commonly seen in plethysmographic waveforms and corresponds to a frequency modulated (FM) heartbeat. In accordance with one aspect of the present invention, a rule based method for determining the pulserate of a heart producing the spectrum of FIG. 14B is disclosed. The rule based method is based on a time domain model (a "stick model") plotted in FIG. 14C. This elegantly simple model captures the essential feature of the plethysmographic waveform. FIG. 14C shows an x axis 1401 corresponding to time, and a y axis 1402 corresponding to the amount of blood being forced into the arteries by a heart. FIG. 14C further shows two overlapping waveforms. A first waveform 1403 shows to blood being forced into the arteries during a first time interval $T_1$. A second waveform 1404 shows blood being forced into the arteries during a second time interval $T_2$. The two time intervals, $T_1$ and $T_2$, do not overlap and the total period of the sum of the two waveforms is $T_1+T_2$. The sum of the two waveforms represents a heart that is beating at two different pulserates on alternate beats. For example, if the heartbeats were numbered, then on every even numbered beat, the heartbeat would last $T_1$ seconds. On every odd numbered beat, the heartbeat would last $T_2$ seconds. This is not art unusual occurrence, and there are physiological reasons why this occurs. The spectrum shown in FIG. 14B is essentially the spectrum of the superposition of the waveforms 1403 and 1404.

Figure 15:
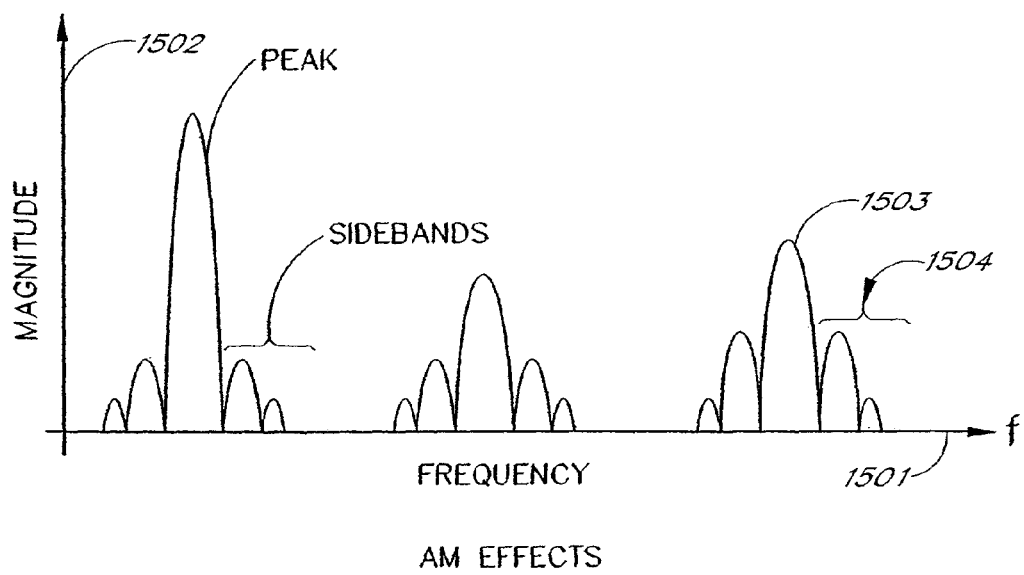
FIG. 15 is an idealized frequency domain plot of a plethysmographic wave showing the effects of AM modulation.

Amplitude modulation (AM) of the plethysmographic waveform is also possible and common. Amplitude modulation occurs primarily when the heart beats with different strength on different heartbeats. FIG. 15 shows a sample spectrum F(w) that exhibits the effects of AM. FIG. 15 shows a frequency axis 1501 and a spectrum axis 1502. The spectrum consists of a series of spectral peaks 1503 and sidebands 1504. One skilled in the art will recognize this as a typical AM spectrum of a carrier and its associated modulation sidebands. Under some conditions, of high pulserate and substantial modulation bandwidth, the sidebands 1504 due to one spectral peak 1503 can overlap the sidebands due to an adjacent spectral peak. This overlap significantly complicates the waveform (not shown).

Figure 16A:
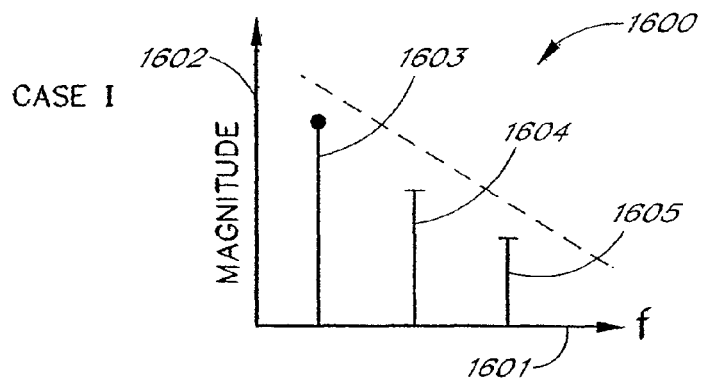
FIGS. 16A, 16B, and 16C are a group of idealized frequency domain plots that illustrate the various categories used in the rule based method for determining pulserate in accordance with one aspect of the present invention.
Figure 16B:
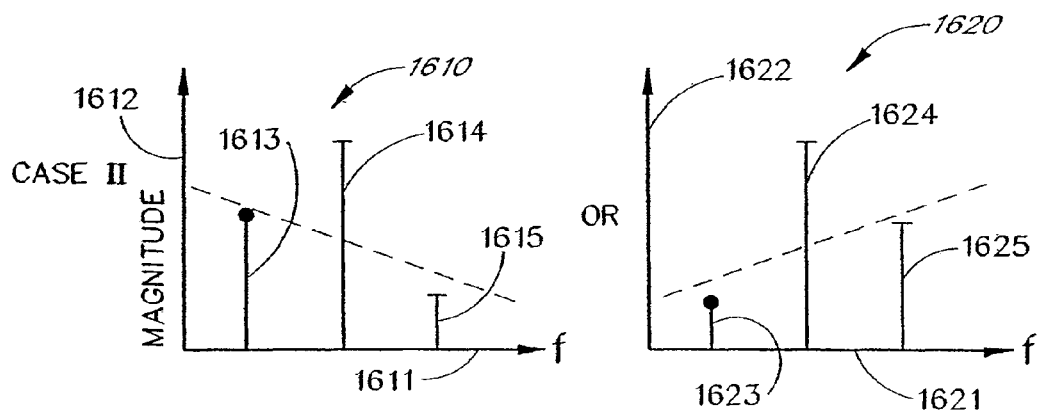
Figure 16C:
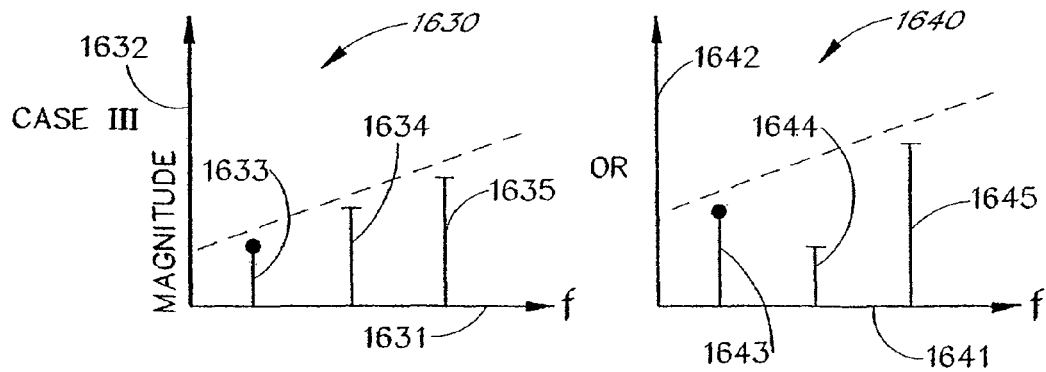

In accordance with one aspect of the present invention, the pulserate can be determined in the presence of FM and AM distortions by classifying the spectrum as one of five categories grouped into three cases. The five categories are illustrated as idealized graphs in: FIG. 16A, illustrating Case I; FIG. 16B, illustrating Case II; and FIG. 16C, illustrating Case III.

FIG. 16A shows a plot 1600 having an x axis 1601 corresponding to frequency and a y axis 1602 corresponding to the magnitude of the spectrum. FIG. 16A also shows a first spectral line 1603, a second spectral line 1604 and a third spectral line 1605. The three spectral lines 1603, 1604, and 1605 show a monotonically decreasing amplitude where the decrease is approximately linear.

FIG. 16B shows a first plot 1610 having an x axis 1611 corresponding to frequency and a y axis 1612 corresponding to the magnitude of the spectrum. The first plot 1610 also shows a first spectral line 1613, a second spectral line 1614 and a third spectral line 1615. The third spectral line 1615 has the smallest amplitude of the three lines. The second spectral line 1614 has the largest amplitude of the three lines, and its amplitude rises significantly above a line drawn from the first spectral line 1613 to the third spectral line 1615.

FIG. 16B also shows a second plot 1620 having an x axis 1621 corresponding to frequency and a y axis 1622 corresponding to the magnitude of the spectrum. The second plot 1620 also shows a first spectral line 1623, a second spectral line 1624 and a third spectral line 1625. The first spectral line 1623 has the smallest amplitude of the three lines. The second spectral line 1624 has the largest amplitude of the three lines, and its amplitude rises significantly above a line drawn from the first spectral line 1623 to the third spectral line 1625.

FIG. 16C shows a first plot 1630 having an x axis 1631 corresponding to frequency and a y axis 1632 corresponding to the magnitude of the spectrum. The first plot 1630 also shows a first spectral line 1633, a second spectral line 1634 and a third spectral line 1635. The amplitudes of the three spectral lines are monotonically increasing, and the increase is approximately linear.

FIG. 16C also shows a second plot 1640 having an x axis 1641 corresponding to frequency and a y axis 1642 corresponding to the magnitude of the spectrum. The second plot 1640 also shows a first spectral line 1643, a second spectral line 1644 and a third spectral line 1645. The third spectral line 1645 has the smallest amplitude of the three lines. The second spectral line 1644 has the largest amplitude of the three lines, and its amplitude is significantly below a line drawn from the first spectral line 1643 to the second spectral line 1645.

In accordance with one aspect of the present invention, the pulserate is determined by identifying the largest three spectral lines, then matching the spectrum to one of the idealized spectra shown by the plots 1600, 1610, 1620, 1630, or 1640, and then applying one of a set of rules to determine the pulserate. It will be understood by one skilled in the art that, although the frequencies of the spectral shown in the plots 1600, 1610, 1620, 1630, or 1640 appear to be harmonically related. In practice the spectral lines may not correspond to frequencies which are harmonics.

Figure 18B:
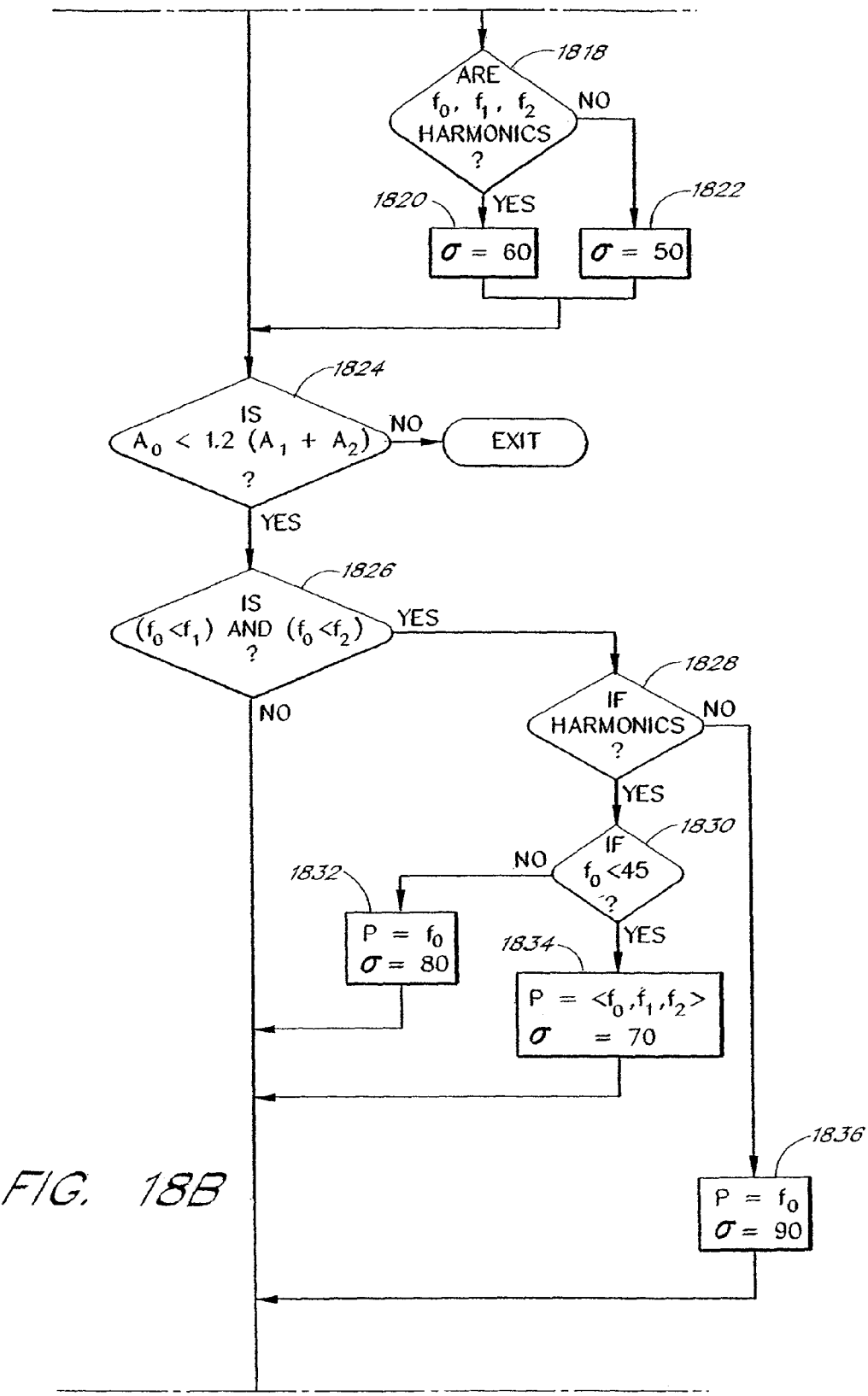
Figure 18C:
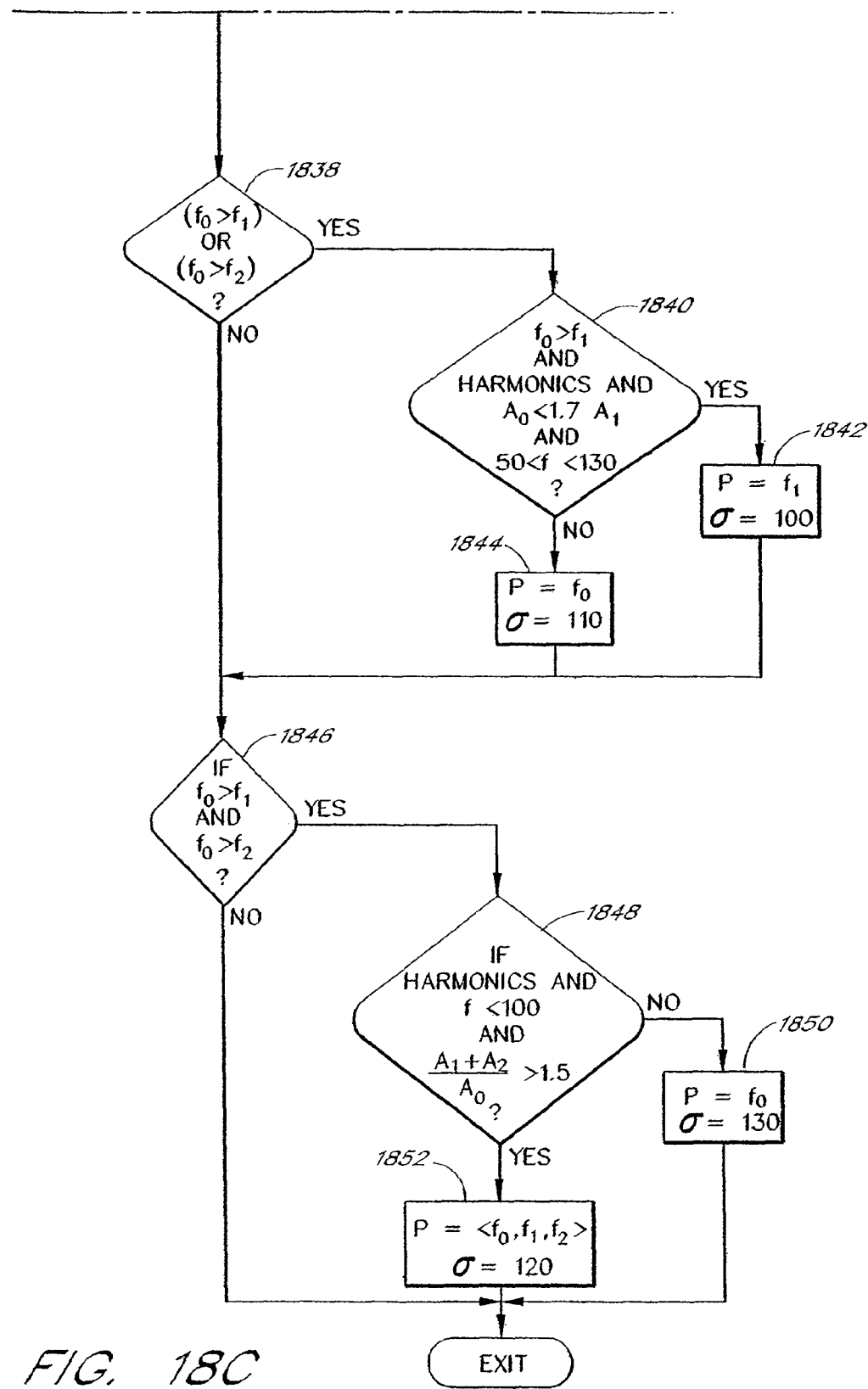

The details of the rule based process are shown in the flowchart of FIG. 18. FIG. 18 begins at a start block 1802 and proceeds to an initialization process block 1804. In the block 1804, the values of the pulserate, p, and confidence factor, s, are set to zero. When the process reaches an exit block, p will contain the pulserate (or zero if no pulserate was found), and σ will contain a confidence factor indicating related to the pulserate (or zero if no pulserate was found). After completing the initialization block 1804, the process advances to a search process block 1805 where the spectrum |F(ω)| is searched for the first three spectral peaks. After finding the peaks, the process advances to a decision block 1806 where the process checks the number of spectral peaks actually found. If, in the decision block 1806, the number of peaks is less than three, then the process advances to a decision block 1808; otherwise, the process jumps forward to a process block 1812. If, in the process block 1808, the number of peaks is greater than zero, then the process advances to a process block 1810; otherwise, the process jumps to an exit block. In the process block 1810, the value of p is set to the frequency corresponding to the largest of the spectral peaks, the confidence value is set to 10, and the process then advances to the exit block.

In the process block 1812, the first three spectral peaks are sorted by magnitude, and the values assigned to variables $A_0$, $A_1$, and $A_2$ such that $A_0$ is the magnitude of the largest peak, $A_1$ is the magnitude of the middle peak, and A is the magnitude of the smallest peak. Also, in the process block 1812, variables $f_0$, $f_1$, and $f_2$, representing the frequencies corresponding to $A_0$, $A_1$ and $A_2$ respectively, are set. Upon completion of the process block 1812, the process advances to a decision block 1814. In the decision block 1814, if $A_0$ is greater than or equal to $1.2*(A_1+A_2)$ and $f_0$ is less than 250, then the process advances to a process block 1816; otherwise the process jumps to a decision block 1824. In the process block 1816, the value of p is set to $p=f_0$, and the process then advances to a decision block 1818. In the decision block 1818, the values of $f_0$, $f_1$, and $f_2$ are checked to see if they are harmonics of one another. In a preferred embodiment, this is done by checking to see whether a frequency $f_i$ is within ten beats per minute of being a integer multiple of another frequency $f_j$ (where i,j=0, 1, or 2). If the decision block 1818 detects that the frequencies are harmonics, then the process advances to a process block 1820; otherwise, the process advances to a process block 1822. In the process block 1820, the value of σ is set to 60, and the process then advances to the decision block 1824. In the process block 1822, the value of σ is set to 50 and the process then advances to the decision block 1824.

In the decision block 1824, if $A_0<1.2*(A_1+A_2)$, then the process advances to a decision block 1826, otherwise the process advances to the exit block. In the decision block 1826, if $(f_0<f_1)$ and $(f_0<f_2)$, then the process advances to a decision block 1828; otherwise the process advances to a decision block 1938. In the decision block 1828, if the frequencies $f_0$, $f_1$, and $f_2$ are harmonics, then the process advances to a decision block; otherwise, the process advances to a process block 1836. In the process block 1836, the value of p is set to $p=f_0$, the value of a is set to 90, and the process then advances to the decision block 1838. In the decision block 1830, if $f_0$ is less than 45 beats per minute, then the process advances to a process block 1834; otherwise, the process advances to a process block 1832. In the process block 1832, the value of p is set to $p=f_0$, the value of a is set to σ=80, and the process then advances to the decision block 1838. In the process block 1834, the value of σ is set to $p=(f_0+f_1+f_2)/3$, the value of σ is set to σ=70, and the process then advances to the decision block 1838.

In the decision block 1838, if $f_0>f_1$ or $f_0>f_2$, then the process advances to a decision block 1840; otherwise, the process advances to a decision block 1846. In the decision block 1840, if $(f_0>f_1)$ and $(f_0, f_1$ and $f_2$ are harmonics) and $(A_0<1.7A_1)$ and $(30<f_1<130)$ then the process advances to a decision block 1842; otherwise, the process advances to a process block 1844. In the process block 1842, the value of p is set to $p=f_1$ the value of σ is set to σ=100, and the process then advances to the decision block 1848. In the process block 1844, the value of p is set to $p=f_0$, the value of σ is set to σ=110, and the process then advances to the decision block 1848.

In the decision block 1848, if $(f_0, f_1$ and $f_2$, are harmonics) and $f_0<100$ and $(A_1+A_2)/A_0>1.5)$, then the process advances to a process block 1852; otherwise, the process advances to a process block 1850. In the process block 1852, the value of p is set to $p=(f_0+f_1+f_2)/3$, the value of σ is set to σ=120, and the process then advances to the exit block. In the process block 1852, the value of p is set to $p=f_0$, the value of σ is set to σ=130, and the process then advances to the exit block.

As stated previously, when the process shown in FIG. 18 reaches the exit block, p contains the pulserate, and σ contains the confidence factor. The confidence factor is a number indicating the likelihood that the value of p accurately represents the actual pulserate of the patient.

Transform Based Pulserate Detection

Figure 17:
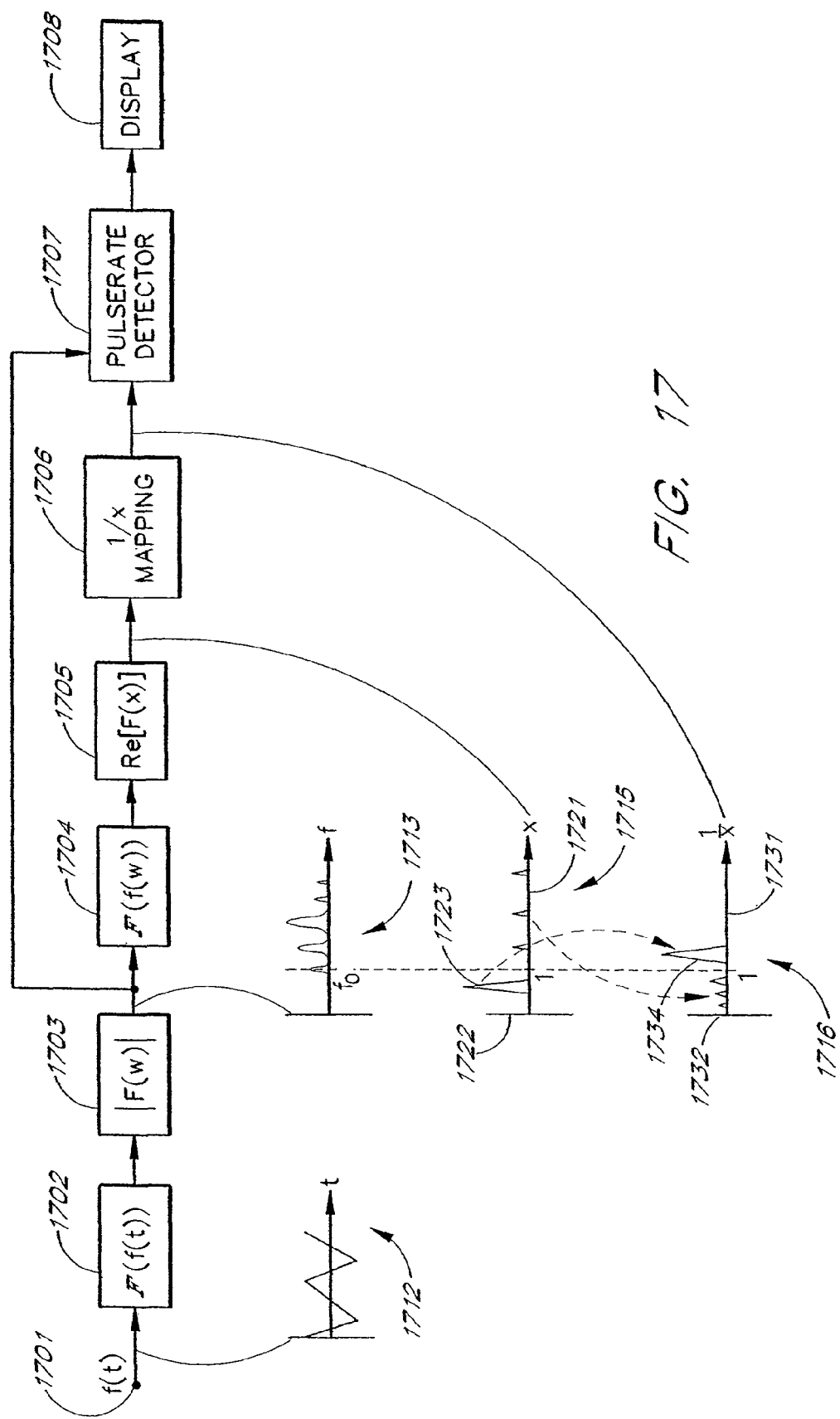
FIG. 17 is a block diagram which illustrates the signal processing used to determine pulse rate by the pleth to pulserate transform method (PPRT) in accordance with one aspect of the present invention.

In accordance with another aspect of this invention, the pulserate can be determined in the presence of FM and AM distortions by using a pleth to pulserate transform (PPRT). FIG. 17 shows a schematic of a signal processing system that implements a PPRT. In FIG. 17, a time domain plethysmographic waveform f(t) is fed into an input 1701. The signal at the input 1701 is fed into a Fourier transform block 1702 which forward transforms f(t) into the frequency domain. An output of the block 1702 is expressed mathematically as $F(\omega)=\mathcal{F}[f(t)]$. The output of the block 1702 is fed into a magnitude block 1703 which finds the magnitude of the signal F(ω). An output of the magnitude block 1703, shown as a plot 1713, is fed into a second forward Fourier transform block 1704 which transforms the signal |F(ω)| into a signal G(x) where $G(x)=\mathcal{F}[|F(\omega)|]$ and G(x) is a complex number. The output of the block 1704 is fed into a block 1705 which extracts the real portion of G(x). The real portion of G(x) is then fed into a 1/x mapping block 1706. An output of the mapping block 1706 is fed into a pulserate detector block 1707. A pulserate output from the detector block 1706 is sent to a display 1708.

In an alternate embodiment, the magnitude block could be replaced by a block which extracts the real portion of the waveform. Likewise, the block 1705 which extracts the real portion of G(x) could be replaced by a magnitude block which extracts |G(x)|.

One skilled in the art will recognize that the output of the magnitude block 1703 is merely the absolute value of the Fourier transform of the plethysmographic wave f(t) on a point by point basis. The graph 1713 shows this signal as a series of spectral lines of varying amplitudes. In many cases, this spectrum will be similar to that shown in FIG. 1413, and has a fundamental frequency $f_0$, and a series of harmonics $f_1$ and $f_2$ of various amplitudes. As shown in FIG. 14B, any attempt at determining pulserate merely by finding the largest spectral line will lead to erroneous results. Further, the clean waveform of FIG. 14B, showing a series of spectral peaks, will often be contaminated by AM sidebands as shown in FIG. 15. Thus the fundamental periodic nature of the heartbeat is not always readily apparent in the spectrum of plot 1713. This is the reason for the second Fourier transform in process block 1704.

The nature of the Fourier transform is to identify and quantify the periodic nature of a function. If the waveform shown in the plot 1713 were in the time domain, rather than the frequency domain, then the series of pulses (the spectral lines of the plot 1713) would correspond to a periodic train of pulses, having a fundamental frequency given by the pulse repetition frequency and modulated by the spectrum of the individual pulses. Mathematically, it does not matter that the waveform of the plot 1713 is not in the time domain. The Fourier transform can still be applied, and it will still produce a very strong spectral line corresponding to the inherent periodicity, and corresponding component strength, of the waveform.

Thus, the operation of the block 1704, in performing a forward Fourier transform on a frequency domain waveform is mathematically viable, and yields the desired data. The only unique ramification of the fact that the transformed data is already in the frequency domain rather than the time domain is the effect on the x axis. It is well known to those skilled in the art, that the forward Fourier transform maps the x axis into 1/x. This is most easily explained by noting that, normally, one would transform f(t) into F($\omega$). Since t=1/w (to within a constant factor of $2\pi$) it is clear that a 1/x mapping has occurred. In the present context, the 1/x mapping is undesirable because the data was already in the frequency domain. Thus the mapping must be undone by the process block 1706.

Once the waveform has been remapped in the process block 1707, it is a simple matter to find the desired pulserate in the process block 1707, because the pulserate will correspond to the largest spectral peak. Again, this occurs because the second Fourier transform "identifies" the dominant periodicity (e.g., the dominant string of harmonics) and collapses that periodicity into a single spectral line. The pulserate detector 1707 merely searches for the largest spectral peak and sends, to the display 1708, the frequency that corresponds to the largest peak.

In yet another embodiment, the process block 1707 looks for the existence of a spectral peak below 120 beats per minute. If a spectral peak below 120 beats per minute is found, then the frequency corresponding that peak is the pulserate. Of, on the other hand, no spectral peak below 120 beats per minute is found, then the process block 1707 finds the largest spectral peak in the original fourier spectrum that exists at the output of the Fourier transform block 1702. The pulserate is then the frequency corresponding to the largest spectral peak at the output of the Fourier transform block 1702.

In yet another embodiment, the ratio of the largest two peaks in the PPRT waveform 1716 can be used to generate a confidence factor that provides some indication of the accuracy of the computed pulserate. In a preferred embodiment, a contrast ratio is computed by dividing the magnitude of the largest peak in the PPRT waveform 1716 by the magnitude of the second largest peak in the PPRT waveform 1716. A large contrast ratio corresponds to high confidence that the computed pulserate is accurate. A contrast ratio near unity corresponds to low confidence that the computed pulserate is accurate.

Neural Network Embodiments

In yet another embodiment, much of the signal processing can be accomplished by a neural network. One skilled in the art will recognize that the signal processing associated with the removal of motion artifacts involves non-linear and linear processes. The frequency domain waveform scrubber 1260 and the time domain waveform scrubber 1242 are both linear processes. However, the calculation of a in FIG. 12 is a non-linear process, in part because it includes the ratio operation represented by the process block 1230. The calculation of pulserate, either by the rule based method, or the PPRT method both involve ratios and are thus non-linear processes as well.

Figure 19:
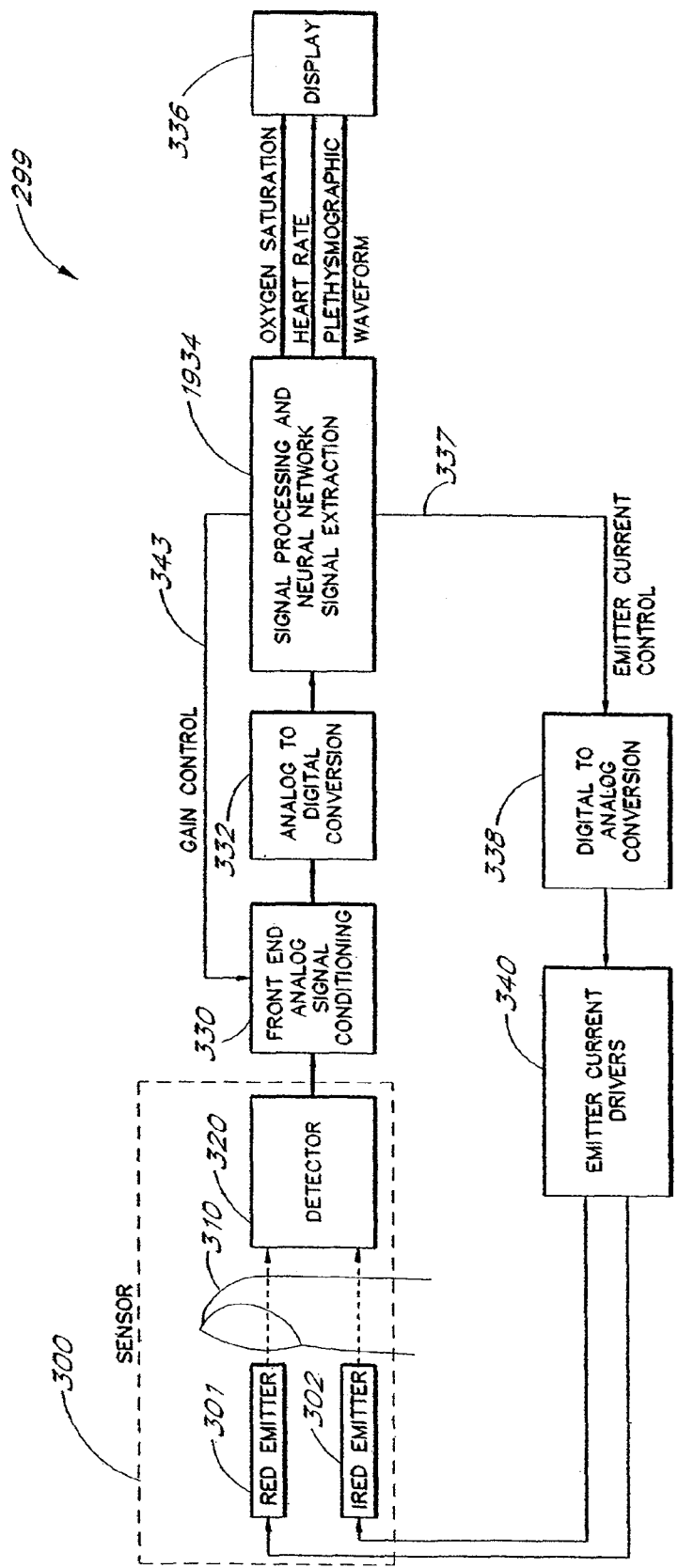
FIG. 19 illustrates a schematic diagram of a physiological monitor that uses a neural network in accordance with the teachings of one aspect of the present invention.

One skilled in the art will appreciate that other non-linear filtering processes can be used. In particular, any of these non-linear processes can be performed by a neural network as shown in FIG. 19. FIG. 19 depicts a general hardware block diagram of a pulse oximeter 299 that employs neural network processing. A sensor 300 has two light emitters 301 and 302, such as LED's. One LED 301 emitting light of red wavelengths and another LED 302 emitting light of infrared wavelengths are placed adjacent a finger 310. A photodetector 320, which produces an electrical signal corresponding to the attenuated visible and infrared light energy signals is, located near the LED's 301 and 302. The photodetector 320 is connected to front end analog signal conditioning circuitry 330.

The front end analog signal conditioning circuit 330 has outputs coupled to an analog to digital conversion circuit 332. The analog to digital conversion circuit 332 has outputs coupled to a digital signal processing and neural network signal extraction system 1934. The signal processing system 1934 provides the desired parameters as outputs for a display 336. Outputs for display are, for example, blood oxygen saturation, heart rate, and a clean plethysmographic waveform.

The signal processing system also provides an emitter current control output 337 to a digital-to-analog converter circuit 338 which provides control information for a set of light emitter drivers 340. The light emitter drivers 340 couple to the light emitters 301, 302. The signal processing system 1934 also provides a gain control output 343 for the front end analog signal conditioning circuitry 330.

Additional Embodiments

While one embodiment of a physiological monitor incorporating a processor of the present invention for determining a reference signal for use in a waveform scrubber, to remove or derive primary and secondary components from a physiological measurement has been described in the form of a pulse oximeter, it will be obvious to one skilled in the art that other types of physiological monitors may also employ the above described techniques.

In particular, one skilled in the art will recognize that in all cases, the Fourier transform disclosed above can be replaced by a Fast Fourier Transform (FFT), a Chirp-Z Transform, a wavelet transform, a discrete Fourier transform, or any other operation that produces the same or similar result.

Furthermore, the signal processing techniques described in the present invention may be used to compute the arterial and venous blood oxygen saturations of a physiological system on a continuous or nearly continuous time basis. These calculations may be performed, regardless of whether or not the physiological system undergoes voluntary motion.

Furthermore, it will be understood that transformations of measured signals other than logarithmic conversion and that the determination of a proportionality factor which allows removal or derivation of the primary or secondary signal portions for determination of a reference signal are possible. Additionally, although the proportionality factor r has been described herein as a ratio of a portion of a first signal to a portion of a second signal, a similar proportionality constant determined as a ratio of a portion of a second signal to a portion of a first signal could equally well be utilized in the processor of the present invention. In the latter case, a secondary reference signal would generally resemble $n'(t)=n_b(t)-rn_a(t)$.

One skilled in the art will realize that many different types of physiological monitors may employ the teachings of the present invention. Other types of physiological monitors include, but are in not limited to, electro-cardiographs, blood pressure monitors, blood constituent monitors (other than oxygen saturation) monitors, capnographs, heart rate monitors, respiration monitors, or depth of anesthesia monitors. Additionally, monitors which measure the pressure and quantity of a substance within the body such as a breathalyzer, a drug monitor, a cholesterol monitor, a glucose monitor, a carbon dioxide monitor, a glucose monitor, or a carbon monoxide monitor may also employ the above described techniques.

Furthermore, one skilled in the art will recognize that many of the signal processing techniques, and many of the filters disclosed herein are classification techniques. Many of the classification mechanisms herein involve classification of spectral lines and ratios of various spectral lines. Other classification schemes are possible within the spirit and scope of the invention.

Furthermore, one skilled in the art will realize that the above described techniques of primary or secondary signal removal or derivation from a composite signal including both primary and secondary components can also be performed on electrocardiography (ECG) signals which are derived from positions on the body which are close and highly correlated to each other.

Furthermore, one skilled in the art will realize that the above described techniques can also be performed on signals made up of reflected energy, rather than transmitted energy. One skilled in the art will also realize that a primary or secondary portion of a measured signal of any type of energy, including but not limited to sound energy, X-ray energy, gamma ray energy, or light energy can be estimated by the techniques described above. Thus, one skilled in the art will realize that the techniques of the present invention can be applied in such monitors as those using ultrasound where a signal is transmitted through a portion of the body and reflected back from within the body back through this portion of the body. Additionally, monitors such as echo-cardiographs may also utilize the techniques of the present invention since they too rely on transmission and reflection.

While the present invention has been described in terms of a physiological monitor, one skilled in the art will realize that the signal processing techniques of the present invention can be applied in many areas, including but not limited to the processing of a physiological signal. The present invention may be applied in any situation where a signal processor comprising a detector receives a first signal which includes a first primary signal portion and a first secondary signal portion and a second signal which includes a second primary signal portion and a second secondary signal portion. Thus, the signal processor of the present invention is readily applicable to numerous signal processing areas.

What is claimed is:

1. A pulse oximetry system for the determination of a physiological parameter wherein said pulse oximetry system is configured to remove motion artifacts from physiological signals, comprising:
   an optical sensor for providing said pulse oximetry system with photo-plethysmographic data, wherein said sensor comprises a light emitting diode for emitting light and a photo-detector for detecting said light, wherein said detected light contains information on the photo-plethysmographic data; and
   a processor for processing the photo-plethysmographic data, wherein said processor is configured to:
   (a) acquire said photo-plethysmographic data;
   (b) transform the photo-plethysmographic data into frequency domain data;
   (c) analyze the frequency domain data to determine a result;
   (d) determine a time domain data photo-plethysmographic signal using said result of said analysis of said frequency domain data;
   (e) analyze a mathematical transformation of the time domain photo-plethysmographic signal to identify parameters;
   (f) use said parameters to determine whether an artifact is present and to identify a physiological signal; and
   (g) determine a physiological parameter from said physiological signal.

2. The system of claim 1 wherein the physiological parameter comprises pulse rate.

3. The system of claim 1 wherein the mathematical transformation comprises a frequency domain transform.

4. The system of claim 1 wherein analyzing the mathematical transformation of the time domain photo-plethysmographic signal comprises identifying peaks.

5. The system of claim 1 wherein the processor is configured to condition the photo-plethysmographic data prior to transforming the data into the frequency domain.

6. The system of claim 1 wherein the processor is configured to analyze the frequency domain data to locate candidate spectral peaks before determining the time domain photo-plethysmographic signal, wherein analyzing said transformed data to locate candidate spectral peaks comprises the steps of assigning a largest power amplitude from said data as a primary candidate spectral peak and assigning a power amplitude that is not a harmonic of said primary candidate spectral peak as a secondary candidate spectral peak.

7. The system of claim 1 wherein analyzing said mathematical transformation of the photo-plethysmographic signal comprises categorizing the signal as corresponding to a predetermined cardiac signal.

8. The system of claim 7 wherein categorizing the signal comprises determining at least one height of a component of the signal.

9. The system of claim 1 wherein analyzing said mathematical transformation of the photo-plethysmographic signal comprises the steps of: determining a plurality of components of the signal, calculating a plurality of heights of said components, and applying a criterion for detecting a predefined set of components.

10. The system of claim 1 wherein using said parameters to identify a physiological signal comprises determining a score indicative of a likelihood that said parameters correspond to said physiological signal.

11. A pulse oximetry system for the determination of a physiological parameter wherein said pulse oximetry system is configured to remove motion artifacts from physiological signals, comprising:
   an optical sensor for providing said pulse oximetry system with photo-plethysmographic data, wherein said sensor comprises a light emitting diode for emitting light and a photo-detector for detecting said light, wherein said detected light contains information on the photo-plethysmographic data; and
   a processor for processing the photo-plethysmographic data, wherein said processor is configured to:
   (a) analyze frequency domain data derived from said photo-plethysmographic data to determine a result,
   (b) determine a time domain photo-plethysmographic signal using said result of said analysis of said frequency domain data;

(c) analyze a mathematical transformation of the time domain photo-plethysmographic signal to identify parameters; and (d) use the identified parameters to determine whether an artifact is present and to identify a physiological signal.

12. A pulse oximetry system for the determination of a physiological parameter wherein said pulse oximetry system is configured to remove motion artifacts from physiological signals, comprising:

a sensor for providing said pulse oximetry system with plethysmographic data, wherein said sensor comprises a light emitter for emitting light and a photo-detector for detecting said light, wherein said detected light contains information on the plethysmographic data; and a processor for processing the plethysmographic data, wherein said processor is configured to:

(a) acquire said plethysmographic data;

(b) transform the plethysmographic data into frequency domain data;

(c) analyze the frequency domain data to determine a result;

(d) determine a time domain data plethysmographic signal using said result of said analysis of said frequency domain data;

(e) analyze the time domain plethysmographic signal to identify parameters;

(f) use said parameters to discriminate a physiological signal from a distortion; and (g) determine a physiological parameter from said physiological signal.

13. The system of claim 12 wherein the physiological parameter comprises pulse rate.

14. The system of claim 12 wherein analyzing the time domain plethysmographic signal comprises determining and analyzing a frequency domain transform.

15. The system of claim 14 wherein analyzing the frequency domain transform of the time domain plethysmographic signal comprises identifying peaks.

16. The system of claim 12 wherein the processor is configured to filter the plethysmographic data prior to transforming the data into the frequency domain.

17. The system of claim 6 wherein filtering said plethysmographic data comprises band pass filtering.

18. The system of claim 12 wherein the processor is configured to analyze the frequency domain data to locate candidate spectral peaks before determining time domain plethysmographic signal data, wherein analyzing said frequency domain data to locate candidate spectral peaks comprises determining power amplitudes of a candidate spectral peak and a spectral peak that is not a harmonic of said candidate spectral peak.

19. The system of claim 12 wherein the processor is configured to analyze the frequency domain data to locate candidate spectral peaks before determining time domain plethysmographic signal data using the frequency domain data.

20. The system of claim 12 wherein the processor is configured to identify peaks after determining the time domain data plethysmographic signal.

21. The system of claim 20 wherein a frequency domain transformation of the time domain plethysmographic signal is analyzed to determine a cardiac physiologic signal characteristic.

22. The system of claim 21 wherein analyzing the frequency domain transformation of the time domain plethysmographic signal comprises categorizing a cardiac spectrum, wherein said cardiac spectrum consists of a plurality of spectral lines.

23. The system of claim 22 wherein analyzing the frequency domain transformation of the time domain plethysmographic signal further comprises the step of determining at least one height of said spectral lines.

24. The system of claim 21 wherein analyzing the frequency domain transformation of the time domain plethysmographic signal comprises the steps of: determining a plurality of spectral lines, calculating a plurality of heights of said spectral lines, and applying a criterion for detecting a predefined category of a set of spectral lines.

25. The system of claim 12 wherein using said parameters to discriminate a physiological signal from a distortion comprises classifying a harmonic set with a score.

26. A pulse oximetry system for the determination of a physiological parameter wherein said pulse oximetry system is configured to remove motion artifacts from physiological signals, comprising:

a sensor for providing said pulse oximetry system with plethysmographic data, wherein said sensor comprises a light emitter for emitting light and a photo-detector for detecting said light, wherein said detected light contains information on the plethysmographic data; and a processor for processing the plethysmographic data, wherein said processor is configured to:

(a) analyze frequency domain data derived from said plethysmographic data to determine a result, (b) determine a time domain plethysmographic signal using said result of said analysis of the frequency domain data;

(c) analyze the time domain plethysmographic signal to identify parameters; and (d) use the identified parameters to discriminate a physiological signal from a distortion.

* * * * *